(12) United States Patent
Rossi et al.

(10) Patent No.: US 8,829,175 B2
(45) Date of Patent: Sep. 9, 2014

(54) NUCLEIC ACIDS ENCODING POLYVALENT PROTEIN COMPLEXES

(75) Inventors: Edmund A. Rossi, Nutley, NJ (US); Chien Hsing Chang, Downingtown, PA (US); William John McBride, Boonton, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 1056 days.

(21) Appl. No.: 11/830,413

(22) Filed: Jul. 30, 2007

(65) Prior Publication Data

US 2008/0171855 A1    Jul. 17, 2008

Related U.S. Application Data

(62) Division of application No. 10/829,388, filed on Apr. 22, 2004, now abandoned.

(60) Provisional application No. 60/464,532, filed on Apr. 22, 2003, provisional application No. 60/525,391, filed on Nov. 24, 2003.

(51) Int. Cl.
    *C07H 21/04*    (2006.01)

(52) U.S. Cl.
    USPC ...................................................... 536/23.53

(58) Field of Classification Search
    USPC ...................................................... 536/23.53
    See application file for complete search history.

(56) References Cited

U.S. PATENT DOCUMENTS

| | | | |
|---|---|---|---|
| 4,642,334 A | 2/1987 | Moore et al. | |
| 4,946,778 A | 8/1990 | Ladner et al. | |
| 5,132,405 A | 7/1992 | Huston et al. | |
| 5,256,395 A * | 10/1993 | Barbet et al. | 424/1.57 |
| 5,837,242 A | 11/1998 | Holliger et al. | |
| 5,844,094 A | 12/1998 | Hudson et al. | |
| 5,916,772 A * | 6/1999 | Lappi et al. | 435/69.7 |
| 5,989,830 A | 11/1999 | Davis et al. | |
| 6,121,424 A | 9/2000 | Whitlow et al. | |
| 6,239,259 B1 | 5/2001 | Davis et al. | |
| 6,300,065 B1 * | 10/2001 | Kieke et al. | 435/6.14 |
| 6,962,702 B2 | 11/2005 | Hansen et al. | |
| 2003/0113333 A1 * | 6/2003 | Rossi et al. | |
| 2003/0162709 A1 * | 8/2003 | Rossi et al. | |

FOREIGN PATENT DOCUMENTS

| | | |
|---|---|---|
| WO | 98/44001 | 10/1998 |
| WO | 02/082041 | 10/2002 |
| WO | WO 03033654 A2 * | 4/2003 |
| WO | WO 03057829 A2 * | 7/2003 |

OTHER PUBLICATIONS

Rossi et al. Clinical Cancer Research 11(19 Suppl):7122s-7129s, Oct. 1, 2005.*

Byers et al. The Journal of Immunology, 140(11):4050-4055, Jun. 1, 1988.*
Goel et al. Cancer Research, 60:6964-6971, Dec. 15, 2000.*
Losman et al. Cancer, 80(12 Suppl):2660-2666, 1997.*
Karacay et al. Bioconjugate Chemistry, 77:842-854, 2000.*
Hillairet de Boisferon et al. Bioconjugate Chemistry, 11(4):452-460, Jul.-Aug. 2000.*
Rossi et al. Ninth Conference on Cancer Therapy with Antibodies and Immunoconjugates, pp. 467-492, Oct. 24-26, 2002.*
Rossi et al. Clinical Cancer Research 9(Suppl):3886s-3896s, Sep. 1, 2003.*
Cochlovius et al. Cancer Research, 60:4336-4341, Aug. 15, 2000.*
Nakamura et al. Cancer, 80(12 Suppl):2650-2655, Dec. 15, 1997.*
Bhatia et al. International Journal of Cancer, 85:571-577, 2000.*
Robert et al (IJC, 81:285-291, 1999).*
Atwell et al., "Design and expression of a stable bispecific scFv dimer with affinity for both glycophorin and N9 neuraminidase", Mol. Immunol. 33(17-18):1301-12 (1996).
Bird et al., "Single-chain antigen-binding proteins", Science 242(4877):423-6 (1988).
Ghetie et al., "Homodimers but not monomers of Rituxan (chimeric anti-CD20) induce apoptosis in human B-lymphoma cells and synergize with a chemotherapeutic agent and an immunotoxin" Blood 97(5):1392-8 (2001).
Goel et al., "Single-Dose versus fractionated radioimmunotherapy of human colon carcinoma xenografts using 131I—labeled multivalent CC49 single-chain fvs" Clin. Cancer Res. 7(1):175-84 (2001).
Helfrich et al., "Construction and characterization of a bispecific diabody for retargeting T cells to human carcinomas" Int. J. Cancer 76(2):232-9 (1998).
Holliger et al., "Carcinoembryonic antigen (CEA)-specific T-cell activation in colon carcinoma induced by anti-CD3 x anti-CEA bispecific diabodies and B7 x anti-CEA bispecific fusion proteins", Cancer Res. 59(12):2909-16 (1999).
Holliger et al., "Retargeting serum immunoglobulin with bispecific diabodies", Nat. Biotechnol. 15(7):632-6 (1997).
Holliger et al., "Diabodies: small bivalent and bispecific antibody fragments", Proc. Natl. Acad. Sci. USA 90 (14):6444-8 (1993).
Huston et al., "Protein engineering of antibody binding sites: recovery of specific activity in an anti-digoxin single-chain Fv analogue produced in *Escherichia coli*", Proc. Natl. Acad. Sci. USA 85(16):5879-83 (1988).
Karacay et al., "Pretargeting for cancer radioimmunotherapy with bispecific antibodies: role of the bispecific antibody's valency for the tumor target antigen", Bioconjug. Chem. 13(5):1054-70 (2002).
Karacay et al., "Therapeutic Advantage of Pretargeted Radioimmunotherapy Using a Recombinant Bispecific Antibody in a Human Colon Cancer Xenograft", Clin. Cancer Res. 11(21):7879-85 (2005).

(Continued)

*Primary Examiner* — Brad Duffy
(74) *Attorney, Agent, or Firm* — Richard A. Nakashima

(57) ABSTRACT

The invention provides for a polyvalent protein complex (PPC) comprising two polypeptide chains generally arranged laterally to one another. Each polypeptide chain typically comprises 3 or 4 "v-regions", which comprise amino acid sequences capable of forming an antigen binding site when matched with a corresponding v-region on the opposite polypeptide chain. Up to about 6 "v-regions" can be used on each polypeptide chain. The v-regions of each polypeptide chain are connected linearly to one another and may be connected by interspersed linking regions. When arranged in the form of the PPC, the v-regions on each polypeptide chain form individual antigen binding sites.

19 Claims, 29 Drawing Sheets

(56) References Cited

OTHER PUBLICATIONS

Kipriyanov et al., "Bispecific tandem diabody for tumor therapy with improved antigen binding and pharmacokinetics", J. Mol. Biol. 293(1):41-56 (1999).

Kipriyanov et al., "Bispecific CD3 X CD19 diabody for T cell-mediated lysis of malignant human B cells", Int. J. Cancer 77:763-772 (1998).

McBride et al., Bispecific antibody pretargeting PET (immunoPET) with an 124l-labeled hapten-peptide, J. Nucl. Med. 47(10):1678-88 (2006).

Morel et al., "Recognition of imidazole and histamine derivatives by monoclonal antibodies", Mol. Immunol. 27 (10):995-1000 (1990).

Pei et al., "The 2.0-Å resolution crystal structure of a trimeric antibody fragment with noncognate VH-VL domain pairs shows a rearrangement of VH CDR3", Proc. Natl. Acad. Sci. USA 94:9637-9642 (1997).

Pluckthun et al., "New protein engineering approaches to multivalent and bispecific antibody fragments", Immunotechnology 3(2):83-105 (1997).

Sharkey et al., "Signal amplification in molecular imaging by pretargeting a multivalent, bispecific antibody", Nat Med. 11(11):1250-5 (2005).

Yarden, Y., "Agonistic antibodies stimulate the kinase encoded by the neu protooncogene in living cells but the oncogenic mutant is constitutively active" Proc. Natl. Acad. Sci. USA 87:2569-2573 (1990).

* cited by examiner

A.
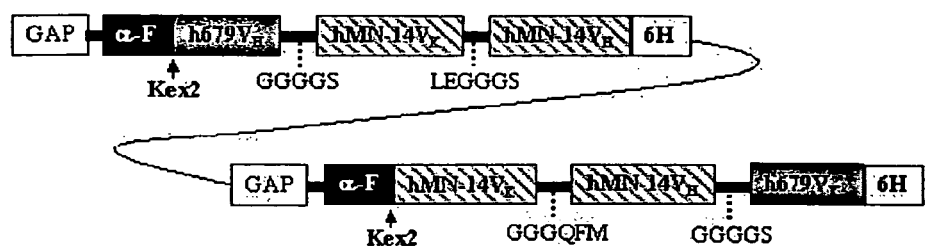
B.
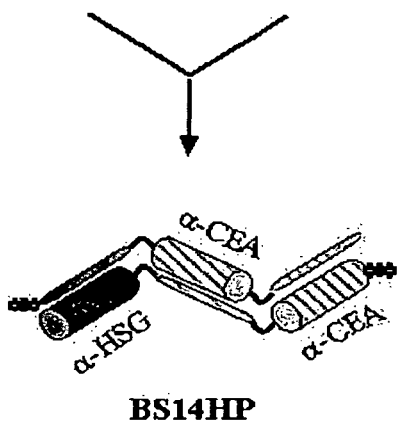
Figure 1

FIG. 1D

1) Amino acid sequence of Polypeptide 1.
EAEAEFM-h679VH-GGGGS-hMN-14VK-LEGGGS-hMN-14VH-VD6His.

EAEAEFMEVQ LVESGGDLVK PGGSLKLSCA ASGFTFSIYT MSWLRQTPGK
                                              CDR1h679VH

GLEWVATLSG DGDDIYYPDS VKGRFTISRD NAKNSLYLQM NSLRAEDTAL
       CDR2h679VH

YYCARVRLGD WDFDVWGQGT TVSVSSGGGG SDIQLTQSPS SLSASVGDRV
      CDR3h679VH                  linker TITCKASQDV GTSVAWYQQK PGKAPKLLIY WTSTRHTGVP SRFSGSGSGT
     CDR1hMN14VK                    CDR2hMN14VK DFTFTISSLQ PEDIATYYCQ QYSLYRSFGQ GTKVEIKRLE GGGSEVQLVE
                 CDR3hMN14VK                linker SGGGVVQPGR SLRLSCSASG FDFTTYWMSW VRQAPGKGLE WIGEIHPDSS
                          CDR1hMN14VH                CDR2hMN14VH

TINYAPSLKD RFTISRDNAK NTLFLQMDSL RPEDTGVYFC ASLYFGFPWF
CDR2hMN14VH                                         CDR3hMN14VH

AYWGQGTPVTVSVDHHHHHH
CDR3hMN14VH    6His

Nucleic acid sequence of BS14HP polypeptide 1

GAGGCTGAAG CTGAATTCAT GGAAGTGCAG CTGGTGGAGT CAGGGGGAGA
CTTAGTGAAG CCTGGAGGGT CCCTGAAACT CTCCTGTGCA GCCTCTGGAT
TCACTTTCAG TATTTACACC ATGTCTTGGC TTCGCCAGAC TCCGGGAAAG
GGGCTGGAGT GGGTCGCAAC CCTGAGTGGT GATGGTGATG ACATCTACTA
TCCAGACAGT GTGAAGGGTC GATTCACCAT CTCCAGAGAC AATGCCAAGA
ACAGCCTATA TCTGCAGATG AACAGTCTAA GGGCTGAGGA CACGGCCTTG
TATTACTGTG CAAGGGTGCG ACTTGGGGAC TGGGACTTCG ATGTCTGGGG
CCAAGGGACC ACGGTCTCCG TCTCCTCAGG AGGTGGCGGA TCCGACATCC
AGCTGACCCA GAGCCCAAGC AGCCTGAGCG CCAGCGTGGG TGACAGAGTG
ACCATCACCT GTAAGGCCAG TCAGGATGTG GGTACTTCTG TAGCTTGGTA
CCAGCAGAAG CCAGGTAAGG CTCCAAAGCT GCTGATCTAC TGGACATCCA
CCCGGCACAC TGGTGTGCCA AGCAGATTCA GCGGTAGCGG TAGCGGTACC
GACTTCACCT TCACCATCAG CAGCCTCCAG CCAGAGGACA TCGCCACCTA
CTACTGCCAG CAATATAGCC TCTATCGGTC GTTCGGCCAA GGGACCAAGG
TGGAAATCAA ACGTCTCGAG GGCGGAGGTA GCGAGGTCCA ACTGGTGGAG
AGCGGTGGAG GTGTTGTGCA ACCTGGCCGG TCCCTGCGCC TGTCCTGCTC
CGCATCTGGC TTCGATTTCA CCACATATTG GATGAGTTGG GTGAGACAGG
CACCTGGAAA AGGTCTTGAG TGGATTGGAG AAATTCATCC AGATAGCAGT
ACGATTAACT ATGCGCCGTC TCTAAAGGAT AGATTTACAA TATCGCGAGA
CAACGCCAAG AACACATTGT TCCTGCAAAT GGACAGCCTG AGACCCGAAG
ACACCGGGGT CTATTTTTGT GCAAGCCTTT ACTTCGGCTT CCCCTGGTTT
GCTTATTGGG GCCAAGGGAC CCCGGTCACC GTCTCCGTCG ACCATCATCA
TCATCATCAT

FIG. 1E

3) Amino acid sequence of polypeptide 2.
EAEAEF-hMN-14VK-GGGQFM-hMN-14VH-GGGGS-h679VK-LD6His.

EAEAEFDIQL TQSPSSLSAS VGDRVTITCK ASQDVGTSVA WYQQKPGKAP
                                     CDR1hMN14VK

KLLIYWTSTR HTGVPSRFSG SGSGTDFTFT ISSLQPEDIA TYYCQQYSLY
    CDR2hMN14VK                                            CDR3hMN14VK

RSFGQGTKVE IKRGGGQFME VQLVESGGGV VQPGRSLRLS CSASGFDFTT
CDR3hMN14VK    linker                                        CDR1hMN14VH

YWMSWVRQAP GKGLEWIGEI HPDSSTINYA PSLKDRFTIS RDNAKNTLFL
CDR1hMN14VH           CDR2hMN14VH

QMDSLRPEDT GVYFCASLYF GFPWFAYWGQ GTPVTVSGGG GSDIVMTQSP
                     CDR3hMN14VH                         linker SSLAVSPGER VTLTCKSSQS LFNSRTRKNY LGWYQQKPGQ SPKLLIYWAST
               CDR1h679VK                                      CDR2h679VK

RESGVPDRFS GSGSGTDFTL TINSLQAEDV AVYYCTQVYY LCTFGAGTKLE
CDR2h679VK                                               CDR3h679VK

LKRLDHHHHH H
    6His

Nucleic acid sequence of BS14HP polypeptide 2

GAGGCTGAAG CTGAATTCGA CATCCAGCTG ACCCAGAGCC CAAGCAGCCT
GAGCGCCAGC GTGGGTGACA GAGTGACCAT CACCTGTAAG GCCAGTCAGG
ATGTGGGTAC TTCTGTAGCT TGGTACCAGC AGAAGCCAGG TAAGGCTCCA
AAGCTGCTGA TCTACTGGAC ATCCACCCGG CACACTGGTG TGCCAAGCAG
ATTCAGCGGT AGCGGTAGCG GTACCGACTT CACCTTCACC ATCAGCAGCC
TCCAGCCAGA GGACATCGCC ACCTACTACT GCCAGCAATA TAGCCTCTAT
CGGTCGTTCG GCCAAGGGAC CAAGGTGGAA ATCAAACGTG GAGGTGGCCA
ATTCATGGAG GTCCAACTGG TGGAGAGCGG TGGAGGTGTT GTGCAACCTG
GCCGGTCCCT GCGCCTGTCC TGCTCCGCAT CTGGCTTCGA TTTCACCACA
TATTGGATGA GTTGGGTGAG ACAGGCACCT GGAAAAGGTC TTGAGTGGAT
TGGAGAAATT CATCCAGATA GCAGTACGAT TAACTATGCG CCGTCTCTAA
AGGATAGATT TACAATATCG CGAGACAACG CCAAGAACAC ATTGTTCCTG
CAAATGGACA GCCTGAGACC CGAAGACACC GGGGTCTATT TTTGTGCAAG
CCTTTACTTC GGCTTCCCCT GGTTTGCTTA TTGGGGCCAA GGGACCCCGG
TCACCGTCTC CGGAGGCGGT GGATCCGACA TTGTGATGAC ACAATCTCCA
TCCTCCCTGG CTGTGTCACC CGGGGAGAGG GTCACTCTGA CCTGCAAATC
CAGTCAGAGT CTGTTCAACA GTAGAACCCG AAAGAACTAC TTGGGTTGGT
ACCAGCAGAA ACCAGGGCAG TCTCCTAAAC TTCTGATCTA CTGGGCATCT
ACTCGGGAAT CTGGGGTCCC TGATCGCTTC TCAGGCAGTG GATCCGGAAC
AGATTTCACT CTCACCATCA ACAGTCTGCA GGCTGAAGAC GTGGCAGTTT
ATTACTGCAC TCAAGTTTAT TATCTGTGCA CGTTCGGTGC TGGGACCAAG
CTGGAGCTGA AACGGCTCGA CCATCATCAT CATCATCAT

BIAcore analysis of BS14HP

Competitive ELISA assay for CEA binding

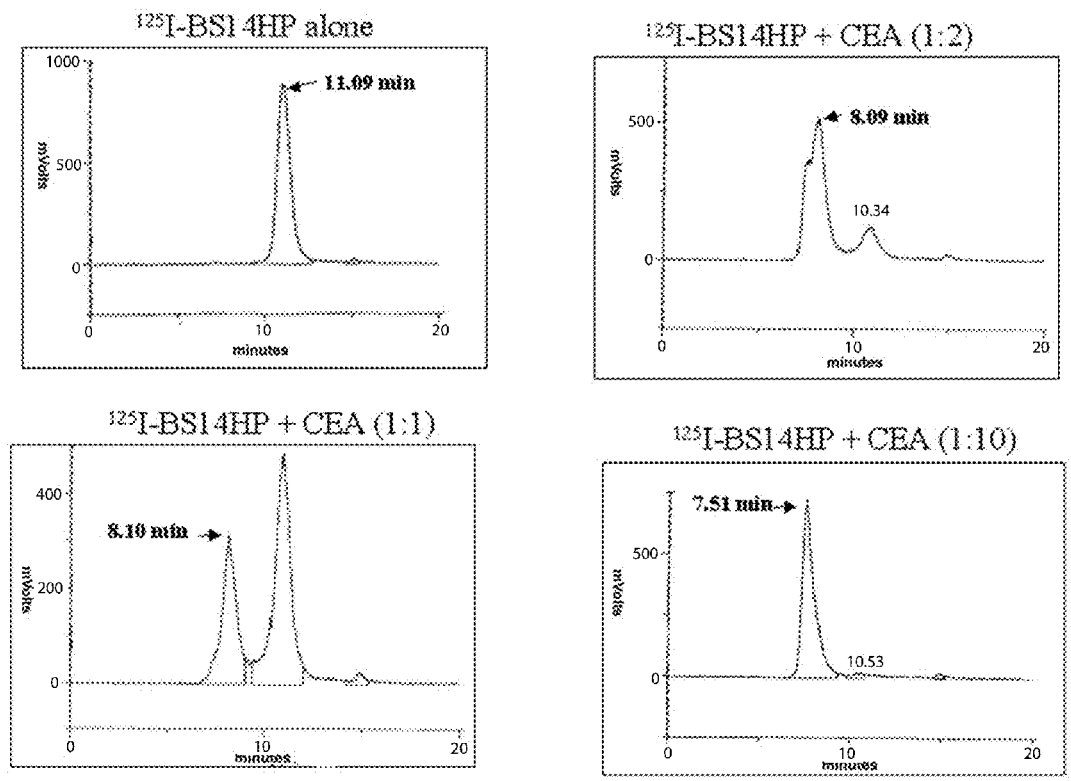
Figure 6B SE-HPLC Analysis of BS14HP immunoreactivity with CEA

A. Biodistribution of 111In-IMP241 in mice pretargeted with BS14HP, BS1.5H or hMN-14 x 679 Fab' x Fab'

B. Tumor/non-tumor ratios of 111In-IMP241 in mice pretargeted with BS14HP, BS1.5H or hMN-14 x 679 Fab' x Fab'

|               | BS14HP         | hMN-14 x 679   | BS1.5H         |
|---------------|----------------|----------------|----------------|
| Liver         | 36.19 (±18.8)  | 22.2 (±6.3)    | 120.00 (±36.0) |
| Spleen        | 57.39 (±46.0)  | 27.8 (±5.9)    | 181.00 (±58.0) |
| Kidney        | 6.7 (0.7±)     | 2.50 (±0.5)    | 2.98 (±1.1)    |
| Lungs         | 29.94 (±15.6)  | 14.10 (±2.8)   | 48.60 (±19.3)  |
| Blood         | 20.32 (±34.7)  | 8.10 (±2.1)    | 284.00 (±50.6) |
| Stomach       | 123.12 (±242.0)| 103.00 (±15.2) | 530.00 (±291.7)|
| Sm. Intestine | 78.95 (±55.0)  | 53.40 (±14.4)  | 235.00 (±138.7)|
| Lg. Intestine | 80.94 (±26.7)  | 37.40 (±9.2)   | 61.20 (±33.2)  |

IMP 281

Functional features of the SV3 shuttle vector.

| HindIII—XhoI—XbaI—Leader peptide—NcoI—SalI—6His—Stop—Stop—BglII—EagI—EcoRI |
|---|

Figure 10 A

Features of the ORF/Polypeptide 1, and ORF/Polypeptide 2

| ORF1/Polypeptide 1<br>Ldr Pep—h679V$_H$—GGGGS—hMN-14V$_K$—LEGGGS—hMN-14V$_H$—HHHHHH |
|---|
| ORF2/Polypeptide 2<br>Ldr Pep—hMN-14V$_K$—GGGQFM—hMN-14V$_H$—GGGGS— h679V$_k$—HHHHHH |

Figure 10B

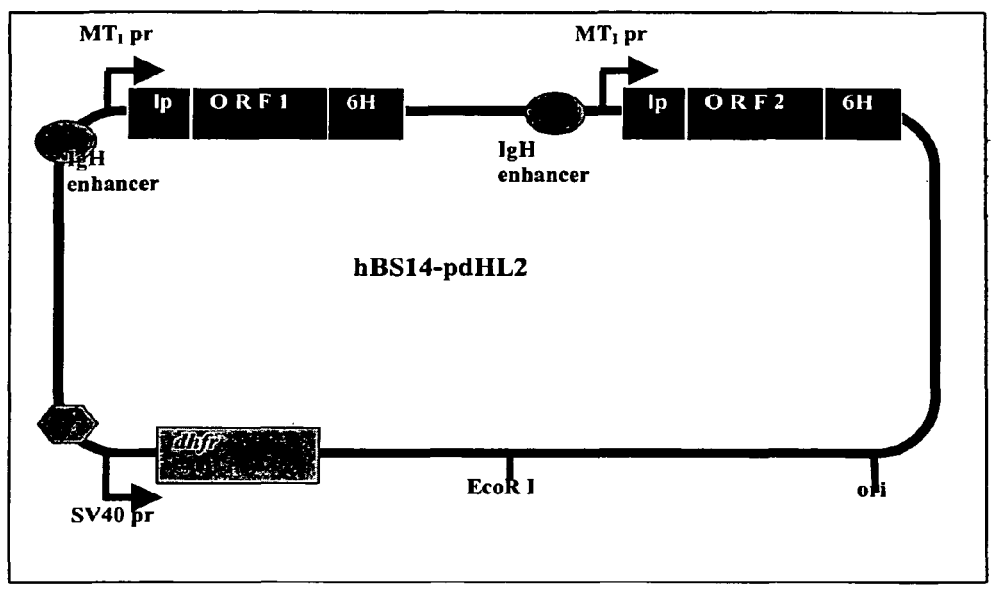
Figure 11. Schematic representation of hBS14-pDHL2 expression vector.

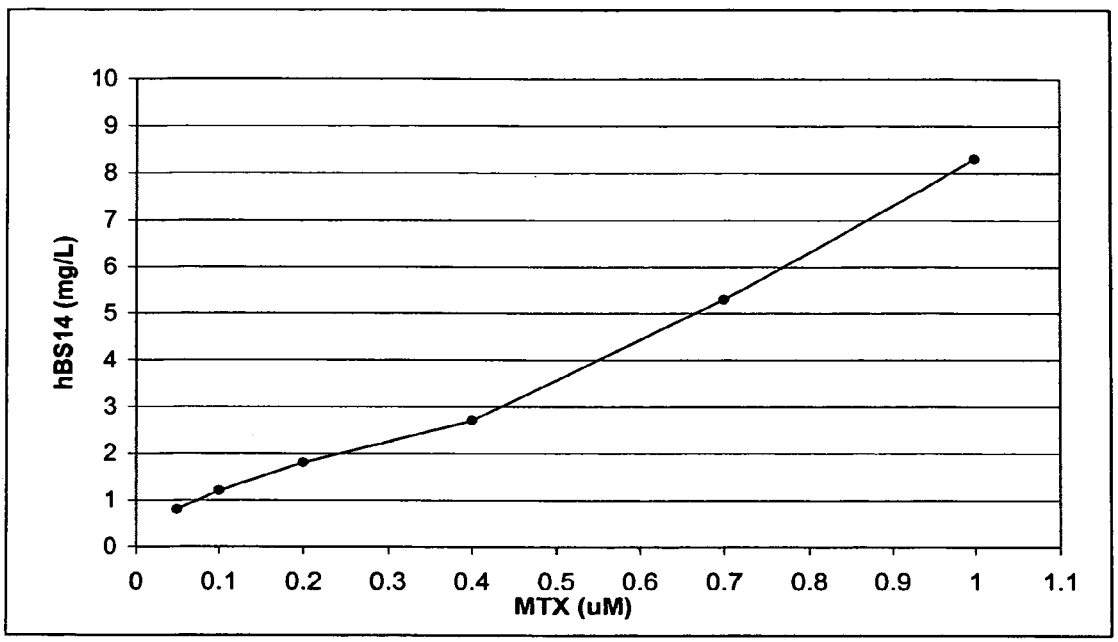
Figure 12. MTX amplification of hBS14 SP2/0 clone 1H6

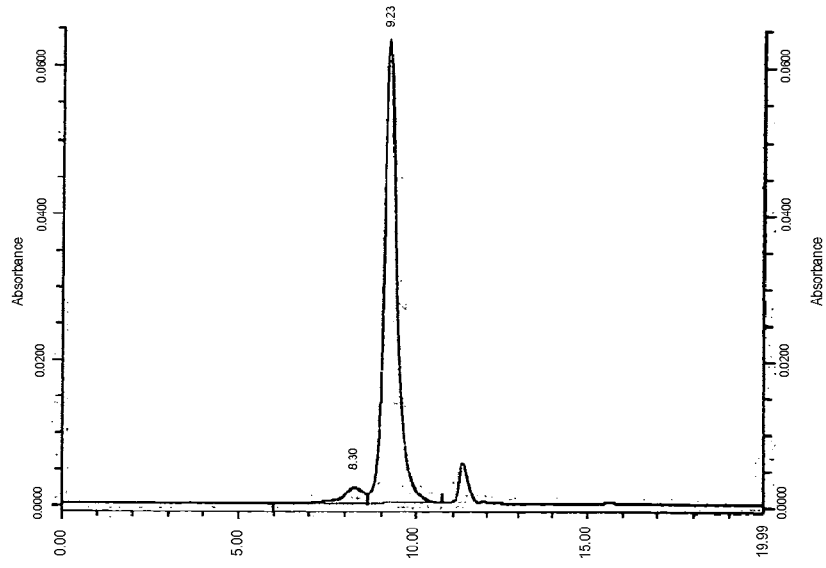
hBS14 102003
YB2/0
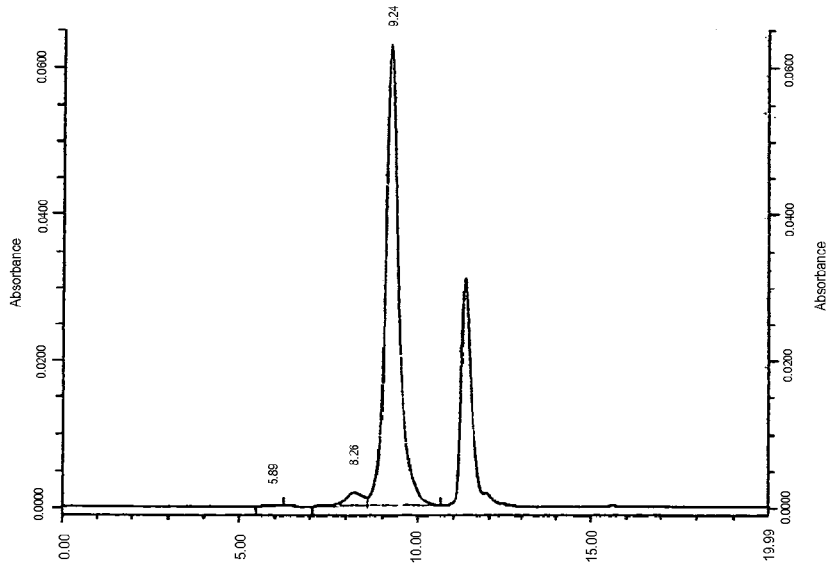
hBS14 100103
SP2/0
Figure 13. SE-HPLC analysis of purified hBS14

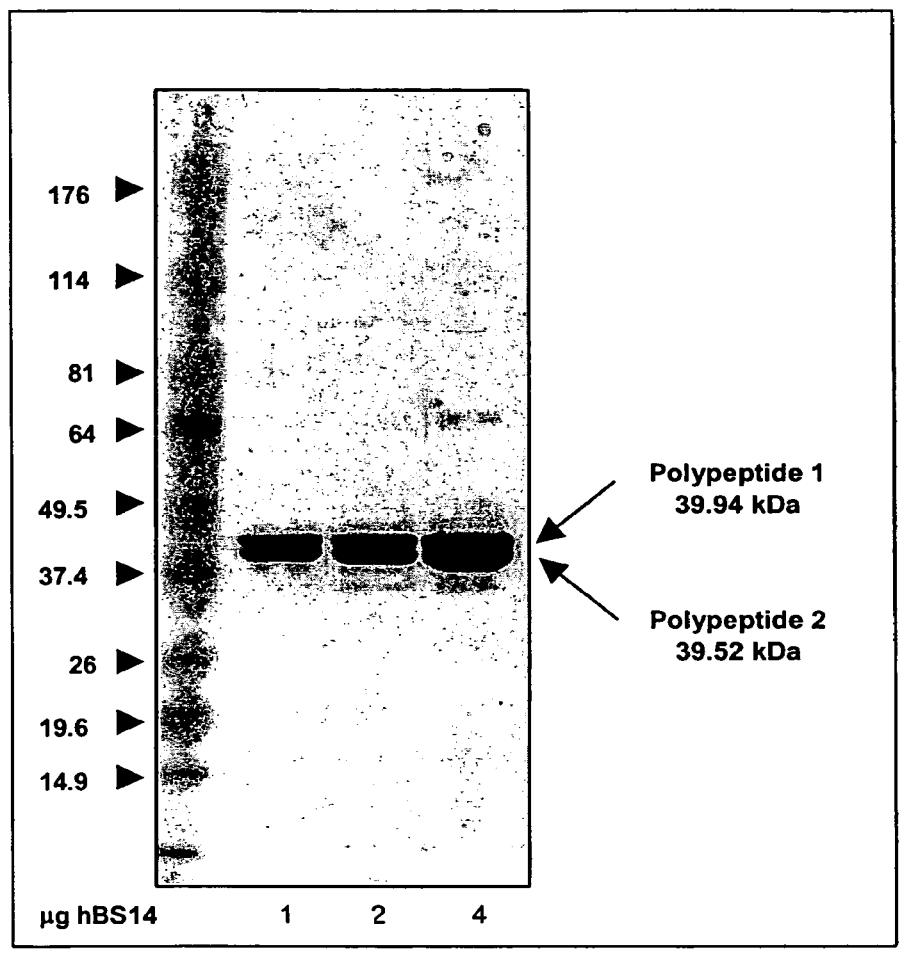
Figure 14. SDS-PAGE analysis of purified hBS14

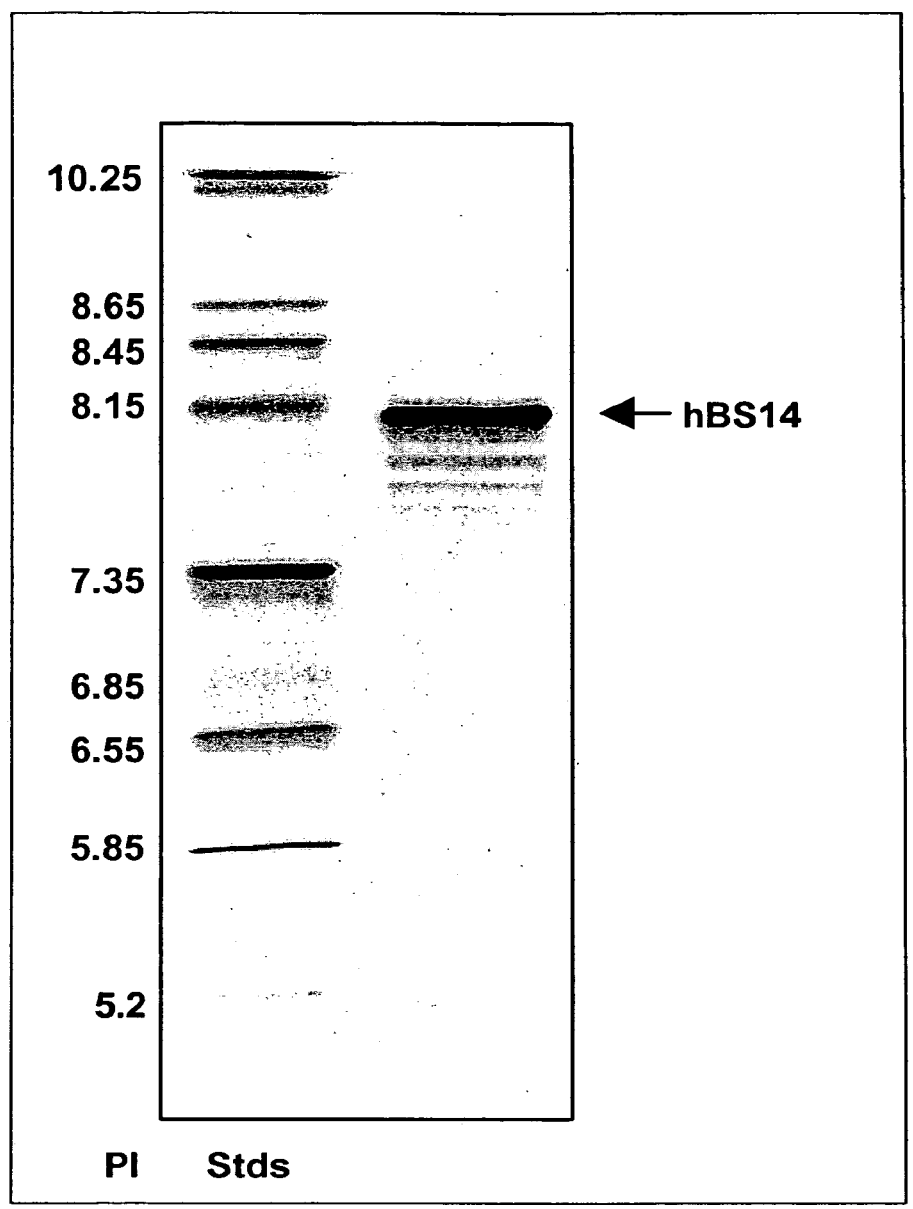
Figure 15. IEF analysis of purified hBS14

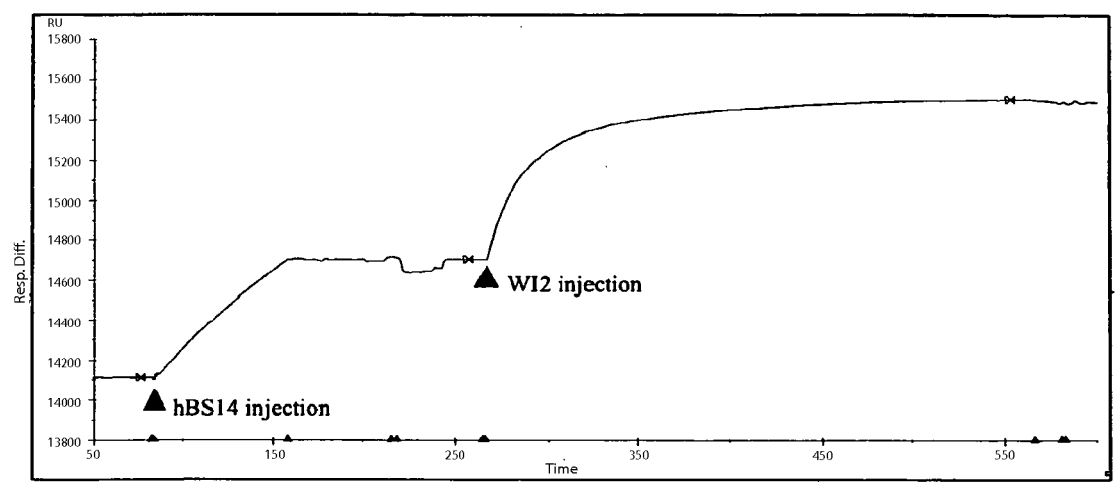
Figure 16. BIAcore analysis of hBS14

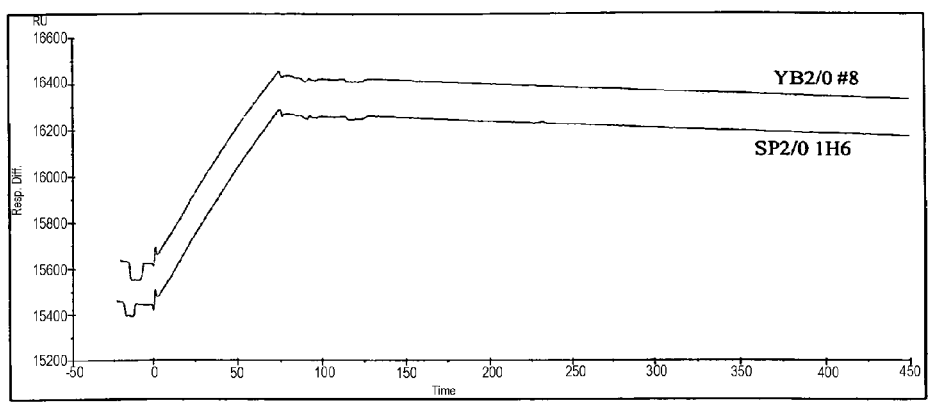
Figure 17. BIAcore analysis of HSG binding of hBS14 produced in either SP2/0 or YB2/0 cells IMP 291  Ac-Lys(HSG-iAsp-)-Cys-NH₂  MH⁺ 656

IMP 245 DOTA-Phe-Lys(HSG)-D-Tyr-Lys(HSG)-Lys(Tscg-Cys-)-NH₂  MH⁺ 1832

Figure 20
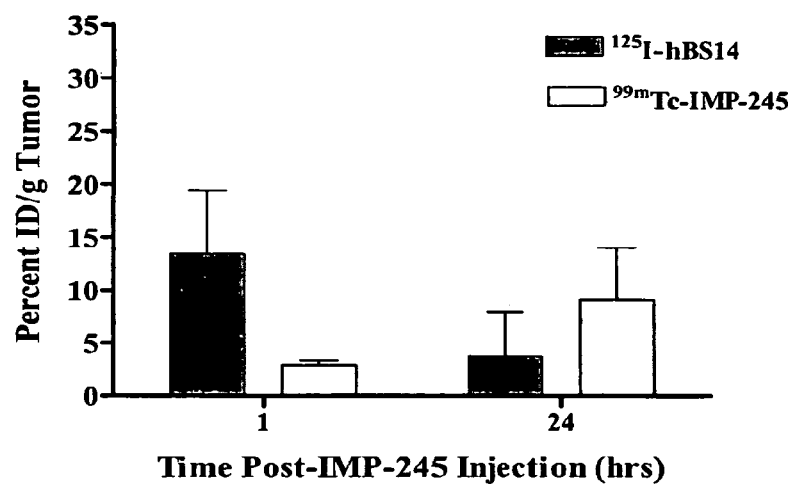
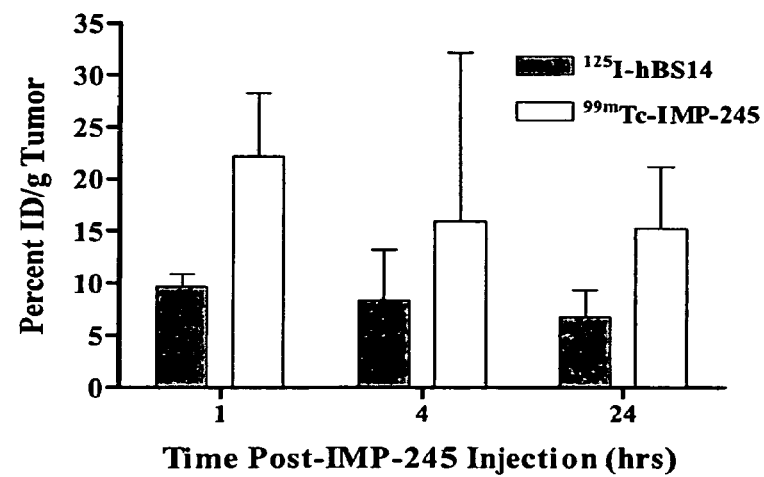

Figure 21
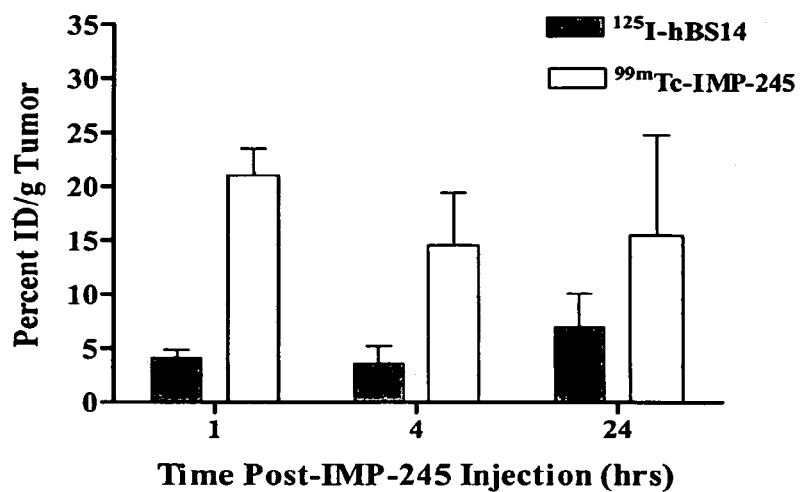
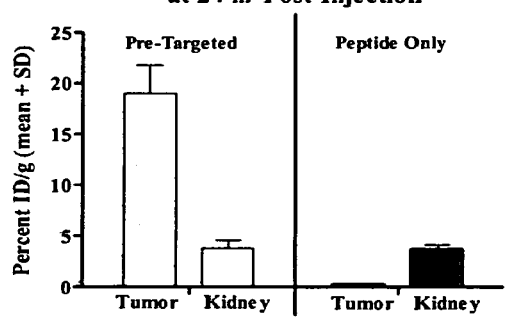

Figure 22

Percent ID/g and Tumor Non-Tumor Ratios of $^{99m}$Tc-IMP-245 at 1 hr Post-Injection.

| Tissue | 4 hrs hBS14 Clearance | | 24 hrs hBS14 Clearance | | 48 hr hBS14 Clearance | |
|---|---|---|---|---|---|---|
| | %ID/g ± (SD) | T:NT Ratio ± (SD) | %ID/g ± (SD) | T:NT Ratio ± (SD) | %ID/g ± (SD) | T:NT Ratio ± (SD) |
| GW-39 | 2.9 ± 0.5 | --- | 22.2 ± 6.1 | --- | 21.0 ± 2.5 | --- |
| Liver | 8.3 ± 0.6 | 0.4 ± 0.07 | 1.5 ± 0.8 | 17.5 ± 6.5 | 1.1 ± 0.2 | 19.7 ± 3.6 |
| Spleen | 7.5 ± 1.9 | 0.4 ± 0.08 | 0.9 ± 0.3 | 27.7 ± 9.4 | 0.5 ± 0.1 | 41.3 ± 9.7 |
| Kidney | 13.4 ± 1.1 | 0.2 ± 0.03 | 5.3 ± 0.8 | 4.1 ± 0.7 | 7.9 ± 0.8 | 2.7 ± 0.5 |
| Lungs | 10.7 ± 3.1 | 0.3 ± 0.10 | 1.7 ± 0.7 | 14.1 ± 4.8 | 1.0 ± 0.4 | 23.0 ± 6.8 |
| Blood | 36.9 ± 6.4 | 0.1 ± 0.01 | 7.1 ± 8.7 | 5.7 ± 3.4 | 1.6 ± 0.3 | 13.6 ± 2.3 |
| Stomach | 1.3 ± 0.4 | 2.4 ± 0.67 | 4.0 ± 7.6 | 29.4 ± 18.8 | 3.5 ± 0.9 | 6.4 ± 2.0 |
| Small Int. | 3.7 ± 0.3 | 0.8 ± 0.07 | 3.9 ± 5.3 | 11.8 ± 6.4 | 2.4 ± 0.5 | 8.8 ± 1.5 |
| Large Int. | 2.2 ± 1.7 | 1.8 ± 0.98 | 0.4 ± 0.2 | 69.4 ± 31.2 | 0.4 ± 0.1 | 56.0 ± 11.5 |
| Muscle | 1.2 ± 0.2 | 2.4 ± 0.32 | 4.8 ± 6.4 | 19.1 ± 26.3 | 4.1 ± 5.0 | 18.4 ± 25.6 |
| Tumor Weight (grams) | 0.309 ± 0.139 | | 0.309 ± 0.136 | | 0.972 ± 0.640 | |

NUCLEIC ACIDS ENCODING POLYVALENT PROTEIN COMPLEXES

This application is a divisional application of U.S. patent application Ser. No. 10/829,388 (now abandoned), filed Apr. 22, 2004, which claims priority to U.S. Provisional Application Nos. 60/464,532, filed Apr. 22, 2003, and 60/525,391, filed Nov. 24, 2003, the contents of which are hereby incorporated by reference in their entirety.

FIELD OF THE INVENTION

The present invention relates to polyvalent protein complexes, including trivalent bispecific proteins, useful for the treatment and diagnosis of diseases, and to methods of producing such proteins.

BACKGROUND OF THE INVENTION

Throughout this specification, various patents, published applications and scientific references are cited to describe the state and content of the art. Those disclosures, in their entireties, are hereby incorporated into the present specification by reference.

The present invention is directed to a novel protein structures, termed a "polyvalent protein complex" or PPC, that comprise three or four antigen binding sites (ABS). These PPC comprise novel properties, such as trivalence and tetravalence, when compared to immunoglobulins and can substitute for immunoglobulins or other engineered antibodies in applications such as diagnosis, detection, and therapy of normal (ectopic) or diseased tissues. These diseased tissues include cancers, infections, autoimmune diseases, cardiovascular diseases, and neurological diseases. Normal tissues can be detected and/or ablated, such as when they are ectopic (misplaced, such as parathyroid, thymus, endometrium) or if they need to be ablated as a therapy measure (e.g., bone marrow ablation in cancer therapies).

Discrete $V_H$ and $V_L$ domains of antibodies produced by recombinant DNA technology may pair with each other to form a heterodimer (recombinant Fv fragment) with binding capability (U.S. Pat. No. 4,642,334). However, such non-covalently associated molecules are not sufficiently stable under physiological conditions to have any practical use. Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains joined with linkers between 3 and 12 amino acid residues form predominantly dimers (termed diabodies). With linkers between 0 and 2 amino acid residues, trimers (termed triabody) and tetramers (termed tetrabody) are in favor, but the exact patterns of oligomerization appear to depend on the composition as well as the orientation of V-domains ($V_H$-linker-$V_L$ or $V_L$-linker-$V_H$), in addition to the linker length. Monospecific diabodies, triabodies, and tetrabodies with multiple valencies have been obtained using peptide linkers consisting of 5 amino acid residues or less. Bispecific diabodies, which are heterodimers of two different polypeptides, each polypeptide consisting of the $V_H$ domain from one antibody connected by a short peptide linker to the $V_L$ domain of another antibody, have also been made using a dicistronic expression vector that contains in one cistron a recombinant gene construct comprising $V_{H1}$-linker-$V_{L2}$ and in the other cistron a second recombinant gene construct comprising $V_{H2}$-linker-$V_{L1}$. (Holliger et al., Proc. Natl. Acad. Sci. USA (1993) 90: 6444-6448; Atwell et al., Molecular Immunology (1996) 33: 1301-1302; Holliger et al., Nature Biotechnology (1997) 15: 632-631; Helfrich et al., Int. J. Cancer (1998) 76: 232-239; Kipriyanov et al., Int. J. Cancer (1998) 77: 763-772; Holiger et al., Cancer Research (1999) 59: 2909-2916]. More recently, a tetravalent tandem diabody (termed tandab) with dual specificity has also been reported (Cochlovius et al., Cancer Research (2000) 60: 43364341]. The bispecific tandab is a dimer of two homologous polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

Methods of manufacturing monospecific diabodies, monospecific triabodies, monospecific tetrabodies and bispecific diabodies by varying the length of the peptide linker as described above are disclosed in U.S. Pat. No. 5,844,094, U.S. Pat. No. 5,837,242, and WO 98/44001.

Alternative methods of manufacturing multispecific and multivalent antigen-binding proteins from $V_H$ and $V_L$ domains are disclosed in U.S. Pat. No. 5,989,830 and U.S. Pat. No. 6,239,259. Such multivalent and multispecific antigen-binding proteins are obtained by expressing a dicistronic vector which encodes two polypeptide chains, with one polypeptide chain consisting of two or more $V_H$ domains (from the same or different antibodies) connected in series by a peptide linker and the other polypeptide chain consisting of complementary $V_L$ domains connected in series by a peptide linker.

Increasing the valency of a binding protein is of interest as it enhances the functional affinity of that protein due to the avidity effect. The increased affinity enables the resulting protein to bind more strongly to target cells. Furthermore, the multivalency may, via crosslinking, induce growth inhibition of target cells (Ghetie, et al, Blood, 97: 1392-8, 2001) or facilitate internalization (Yarden, Proc. Natl. Acad. Sci., USA, 94: 9637, 1990), either property is desirable for an anti-tumor agent. The present invention addresses the continuous need to develop multivalent, multispecific agents for use in therapeutic and diagnostic applications.

Another area of the present invention is in the field of bio-assays. Virtually every area of biomedical sciences is in need of a system to assay chemical and biochemical reactions and determine the presence and quantity of particular analytes. This need ranges from the basic science research lab, where biochemical pathways are being mapped out and their functions correlated to disease processes, to clinical diagnostics, where patients are routinely monitored for levels of clinically relevant analytes. Other areas include pharmaceutical research, military applications, veterinary, food, and environmental applications. In all of these cases, the presence and quantity of a specific analyte or group of analytes, needs to be determined.

For analysis in the fields of chemistry, biochemistry, biotechnology, molecular biology and numerous others, it is often useful to detect the presence of one or more molecular structures and measure binding between structures. The molecular structures of interest typically include, but are not limited to, cells, antibodies, antigens, metabolites, proteins, drugs, small molecules, proteins, enzymes, nucleic acids, and other ligands and analytes. In medicine, for example, it is very useful to determine the existence of a cellular constituents such as receptors or cytokines, or antibodies and antigens which serve as markers for various disease processes, which exists naturally in physiological fluids or which has been introduced into the system. Additionally, DNA and RNA analysis is very useful in diagnostics, genetic testing and research, agriculture, and pharmaceutical development. Because of the rapidly advancing state of molecular cell biology and understanding of normal and diseased systems, there exists an increasing need for methods of detection, which do not require labels such as fluorophores or radioisotopes, are quantitative and qualitative, specific to the molecule of interest, highly sensitive and relatively simple to implement.

Numerous methodologies have been developed over the years to meet the demands of these fields, such as Enzyme-Linked Immunosorbent Assays (ELISA), Radio-Immunoassays (RIA), numerous fluorescence assays, mass spectroscopy, colorimetric assays, gel electrophoresis, as well as a host of more specialized assays. Most of these assay techniques require specialized preparations, especially attaching a label or greatly purifying and amplifying the sample to be tested. To detect a binding event between a ligand and an antiligand, a detectable signal is required which relates to the existence or extension of binding. Usually the signal is provided by a label that is conjugated to either the ligand or antiligand of interest. Physical or chemical effects which produce detectable signals, and for which suitable labels exist, include radioactivity, fluorescence, chemiluminescence, phosphorescence and enzymatic activity to name a few. The label can then be detected by spectrophotometric, radiometric, or optical tracking methods.

SUMMARY OF THE INVENTION

This invention provides a polyvalent protein complex (PPC), a dimer, comprising at least three antigen binding sites (ABS) in a linear array. The invention also provides a fusion PPC, which is a PPC chemically bonded to a second molecule such as a conjugate. It is understood that "fusion PPC" is a subset of all PPC and that references to PPC in this disclosure is also meant to refer to "fusion PPC."

The invention also provides a nucleic acid that encodes at least one polypeptide of a PPC. A host cell that comprise the polypeptide is also an embodiment of the invention.

In addition, the invention also provides a method for reducing a symptom of a disorder, such as a cancer, an infection, a cardiological disorder or an autoimmune disorder by administering a PPC or fusion PPC to a patient.

Specifically, there is provided a polyvalent protein complex (PPC) containing a first and a second polypeptide chain, where the first polypeptide chain contains a polypeptide sequence represented, by the formula $a_1$-$l_1$-$a_2$-$l_2$-$a_3$, where $a_1$, $a_2$, and $a_3$ are immunoglobulin variable domains and $l_1$ and $l_2$ are peptide linkers, and $a_1$ is N-terminal of $a_2$, which in turn is N-terminal of $a_3$, where the second polypeptide chain contains a polypeptide sequence represented by the formula $b_1$-$l_3$-$b_2$-$l_4$-$b_3$, where $b_1$, $b_2$, and $b_3$ are immunoglobulin variable domains and $l_3$ and $l_4$ are peptide linkers, and $b_3$ is N-terminal of $b_2$, which in turn is N-terminal of $b_1$, where the first and second polypeptide chain together form a complex containing at least three antigen binding sites, where each of the antigen binding sites contains a variable domain from the first polypeptide chain and a variable domain from the second polypeptide chain, and where each binding site contains an immunoglobulin heavy chain variable domain and an immunoglobulin light chain variable domain.

Each polypeptide chain may further contain 1-3 additional immunoglobulin variable domains, where each domain is linked via a peptide linker, where the first and second polypeptide chain together form a complex containing 4-6 antigen binding sites, and where each of the antigen binding sites contains a variable domain from the first polypeptide chain and a variable domain from the second polypeptide chain. At least one of the polypeptide chains may further contain an amino acid sequence selected from the group consisting of a toxin, a cytokine, a lymphokine, a enzyme, a growth factor, and an affinity purification tag.

The complex may contain any of the possible combinations of binding affinities, for example, at least two of the antigen binding sites may have the same binding specificity, each of the antigen binding sites may have a different or the same binding specificity, the antigen binding sites may have at least two different binding specificities, at least 3 of the antigen binding sites may have different binding specificities, at least 4 of the antigen binding sites may have different binding specificities, the complex may contain at least 5 antigen binding sites where at least 5 of the binding sites have different binding specificities, or the complex may contain 6 antigen binding sites each having a different binding specificity. In another example two of the antigen binding sites are specific for epitopes of tumor associated antigens, and the third antigen binding sites is reactive with a targetable construct. In another example, two antigen binding sites are specific for epitopes of tumor associated antigens, and the third antigen binding sites is reactive with a targetable construct, where the epitope on the targetable construct is a hapten. In still another complex, the complex is bound to a first hapten on the construct and the construct further contains a second hapten capable of binding simultaneously to a second polyvalent protein complex.

In each of these examples, the complex may bind tumor associated antigen, or antigens are selected from the group consisting of antigens associated with carcinomas, melanomas, sarcomas, gliomas, leukemias and lymphomas, such as α-fetoprotein, A3, CA125, carcinoembryonic antigen (CEA), CD19, CD20, CD21, CD22, CD23, CD30, CD33, CD45, CD74, CD80, colon-specific antigen-p (CSAp), EGFR, EGP-1, EGP-2, folate receptor, HER2/neu, HLA-DR, human chorionic gonadrotropin, Ia, IL-2, IL-6, insulin-like growth factor, KS-1, Le(y), MAGE, MUC1, MUC2, MUC3, MUC4, NCA66, necrosis antigens, PAM4, placental growth factor, prostatic acid phosphatase PSA, PSMA, S100, T101, TAC, TAG-72, tenascin and/or VEGF.

In another example, the complex contains at least two tumor antigen binding sites, where both tumor antigen binding sites are specific for CEA and where the third binding site is specific for the hapten, histamine-succinyl-glycine (HSG).

The polyvalent protein may be BS14HP, or hBS14, which may be bound to IMP 241, or IMP 245

In another embodiment, any of the complexes described above may be used in a pretargeting method of treating or diagnosing or treating and diagnosing a neoplastic condition by (a) administering to the subject a complex as above, where two antigen binding sites are directed to a tumor associated antigen, and one antigen binding sites is directed to a targetable construct containing a bivalent hapten; (b) optionally, administering to the subject a clearing composition, and allowing the composition to clear the polyvalent complex from circulation; and (c) administering to the subject the targetable construct containing a bivalent hapten, where the targetable construct further contains one or more chelated or chemically bound therapeutic or diagnostic agents.

The diagnostic agent may be a radionuclide selected from the group consisting of $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154\text{-}158}$Gd, $^{177}$Lu, $^{32}$P, $^{188}$Re, and $^{90}$Y or a combination thereof, which may be detected, for example, by computed tomography (CT), single photon emission computed tomography (SPECT), or positron emission tomography (PET). The application may be for intraoperative diagnosis to identify occult neoplastic tumors. The targetable construct may contain one or more image enhancing agents for use in magnetic resonance imaging (MRI), such as a metal selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). The targetable construct may contains one or more image enhancing agents for use in ultrasound imaging.

The targetable construct may be a liposome with a bivalent HSG-peptide covalently attached to the outside surface of the liposome lipid membrane. The liposome may be gas filled.

The targetable construct may contain one or more radioactive isotopes useful for killing neoplastic cells, such as $^{32}$P, $^{33}$P, $^{47}$SC, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac or a combination thereof.

The pretargeted therapy may be administered prior to, with or after one or more therapeutic agents. The therapeutic agent may be a cytokine or a chemotherapeutic agent, or a colony-stimulating growth factor. The therapeutic agent may be a chemotherapeutic agent selected from the group consisting of taxanes, nitrogen mustards, ethylenimine derivatives, alkyl sulfonates, nitrosoureas, triazenes; folic acid analogs, pyrimidine analogs, purine analogs, vinca alkaloids, antibiotics, enzymes, platinum coordination complexes, substituted urea, methyl hydrazine derivatives, adrenocortical suppressants, and antagonists, or may be selected from the group consisting of steroids, progestins, estrogens, antiestrogens, and androgens. The therapeutic agent may be a chemotherapeutic agent selected from the group consisting of azaribine, bleomycin, bryostatin-1, busulfan, carmustine, chlorambucil, cisplatin, CPT-11, cyclophosphamide, cytarabine, dacarbazine, dactinomycin, daunorubicin, dexamethasone, diethylstilbestrol, doxorubicin, ethinyl estradiol, etoposide, fluorouracil, fluoxymesterone, gemcitabine, hydroxyprogesterone caproate, hydroxyurea, L-asparaginase, leucovorin, lomustine, mechlorethamine, medroprogesterone acetate, megestrol acetate, melphalan, mercaptopurine, methotrexate, methotrexate, mithramycin, mitomycin, mitotane, phenyl butyrate, prednisone, procarbazine, semustine streptozocin, tamoxifen, taxanes, taxol, testosterone propionate, thalidomide, thioguanine, thiotepa, uracil mustard, vinblastine, and vincristine. The therapeutic agent may be a cytokine selected from the group consisting of interleukin-1 (IL-1), IL-2, IL-3, IL-6, IL-10, IL-12, interferon-alpha, interferon-beta, and interferon-gamma, or may be a colony-stimulating growth factor selected from the group consisting of granulocyte-colony stimulating factor (G-CSF), granulocyte macrophage-colony stimulating factor (GM-CSF), erthropoietin and thrombopoietin.

Also provided is a method of treating a neoplastic disorder in a subject, by administering to the subject a "naked" polyvalent protein complex as described above, where at least one of the antigen binding sites binds to an antigen selected from the group consisting of alpha fetoprotein, A3, CA125, carcinoembryonic antigen (CEA), CD19, CD20, CD21, CD22, CD23, CD30, CD33, CD45, CD74, CD80, colon-specific antigen-p (CSAp), EGFR, EGP-1, EGP-2, folate receptor, HER2/neu, HLA-DR, human chorionic gonadrotropin, Ia, IL-2, IL-6, insulin-like growth factor, KS-1, Le(y), MAGE, MUC1, MUC2, MUC3, MUC4, NCA66, necrosis antigens, PAM-4, placental growth factor, prostatic acid phosphatase PSA, PSMA, S100, T101, TAC, TAG-72, tenascin and VEGF.

The neoplastic disorder may be selected from the group consisting of carcinomas, sarcomas, gliomas, lymphomas, leukemias, and melanomas.

Also provided is a method for treating a B-cell malignancy, or B-cell immune or autoimmune disorder in a subject, containing administering to the subject one or more dosages of a therapeutic composition containing a polyvalent protein complex as described above and a pharmaceutically acceptable carrier.

Also provided is a method for treating a B-cell malignancy, or B-cell immune or autoimmune disorder in a subject, by administering to the subject one or more dosages of a therapeutic composition containing a polyvalent protein complex and a pharmaceutically acceptable carrier, where each antigen binding site binds a distinct epitope of CD19, CD20 or CD22. The complex may be parenterally administered in a dosage of 20 to 1500 milligrams protein per dose, or 20 to 500 milligrams protein per dose, or 20 to 100 milligrams protein per dose. The subject may receive repeated parenteral dosages of 20 to 100 milligrams protein per dose, or repeated parenteral dosages of 20 to 1500 milligrams protein per dose. In these methods, a sub-fraction of the polyvalent protein complex is labeled with a radioactive isotope, such as $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{161}$Tb, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac or a combination thereof.

Also provided is a method for detecting or diagnosing a B-cell malignancy, or B-cell immune or autoimmune disorder in a subject, by administering to the subject a diagnostic composition containing a polyvalent protein complex as above and a pharmaceutically acceptable carrier, where each antigen binding site binds a distinct epitope of CD19, CD20 or CD22, and where the complex is radiolabeled with a radionuclide selected from the group consisting of $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154\text{-}158}$Gd, $^{177}$Lu, $^{32}$P, 188Re, and $^{90}$Y or a combination thereof. Detection may be as described above. The application may be for intraoperative diagnosis to identify occult neoplastic tumors.

Also provided is a method for detecting or diagnosing a B-cell malignancy, or B-cell immune or autoimmune disorder in a subject, containing administering to the subject a diagnostic composition containing a polyvalent protein complex as above and a pharmaceutically acceptable carrier, where each antigen binding site binds a distinct epitope of CD19, CD20 or CD22, and where the complex is labeled with one or more image enhancing agents for use in magnetic resonance imaging (MRI). The image enhancing agent may be as described above Also provided is a method of diagnosing a non-neoplastic disease or disorder, by administering to a subject suffering from the disease or disorder a complex as above, where a detectable label is attached to the complex, and where one or more of the antigen binding sites is specific for a marker substance of the disease or disorder. The disease or disorder may be caused by a fungus, such as *Microsporum, Trichophyton, Epidermophyton, Sporothrix schenckii, Cryptococcus neoformans, Coccidioides immitis, Histoplasma capsulatum, Blastomyces dermatitidis,* and *Candida albican,* or a virus, such as human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia-viruses, Epstein-Barr virus, murine leukemia virus, mumps virus, vesicular stomatitis virus, Sindbis virus, lymphocytic choriomeningitis virus, wart virus and blue tongue virus. The disease or disorder may be caused by a bacterium, such as *Anthrax bacillus, Streptococcus agalactiae, Legionella pneumophilia, Streptococcus pyogenes, Escherichia coli, Neisseria gonorrhoeae, Neisseria meningitidis, Pneumococcus, Hemophilis influenzae* B, *Treponema pallidum*, Lyme disease spirochetes, *Pseudomonas aeruginosa, Mycobacterium leprae, Brucella abortus*, and *Mycobacterium tuberculosis*, or a *Mycoplasma*. The disease or disorder may be caused by a parasite, such as malaria. The disease or disorder may be an autoimmune disease, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis. The disease or disorder may be myocardial infarction, ischemic heart disease, or atherosclerotic plaques, or graft rejection, or Alzheimer's disease, or caused by atopic tissue. The disease or disorder may be inflammation caused by accretion of activated granulocytes, monocytes, lymphoid cells or macrophages at the site of inflammation, and where the inflammation is caused by an infectious agent.

Also provided is a pretargeting method of treating or diagnosing a non-neoplastic disease or disorder in a subject by (a) administering to the subject the polyvalent protein complex of claim 1, where two antigen binding sites are directed to a marker substance, or marker substances specific for the disorder, and one antigen binding sites is directed to a targetable construct containing a bivalent hapten; (b) optionally administering to the subject a clearing composition, and allowing the composition to clear the polyvalent complex from circulation; and (c) administering to the subject the targetable construct containing a bivalent hapten, where the targetable construct further contains one or more chelated or chemically bound therapeutic or diagnostic agents. The disease or disorder may be as described above.

Also provided is a method of antibody dependent enzyme prodrug therapy (ADEPT) by; a) administering to a patient with a neoplastic disorder the polyvalent protein complex as above, where the complex contains a covalently attached enzyme capable of activating a prodrug, (b) optionally administering to the subject a clearing composition, and allowing the composition to clear the polyvalent complex from circulation, and (c) administering the prodrug to the patient.

Also provided are assay and immunostaining methods using one or more polyvalent protein complexes as described above.

Further provided is an isolated nucleic acid molecule encoding a first or second polypeptide as described above, and a nucleic acid expression cassette containing such an isolated nucleic acid. Also provided is an episome containing: (a) a first promoter operationally connected to a first nucleic acid encoding a first polypeptide containing a polypeptide chain represented by the formula $a_1$-$l_1$-$a_2$-$l_2$-$a_3$, where $a_1$, $a_2$, and $a_3$ are immunoglobulin variable domains and $l_1$ and $l_2$ are peptide linkers, (b) a second promoter operationally connected to a second nucleic acid encoding a polypeptide containing a second polypeptide chain represented by the formula $b_1$-$l_3$-$b_2$-$l_4$-$b_3$, where $b_1$, $b_2$, and $b_3$ are immunoglobulin variable domains and $l_3$ and $l_4$ are peptide linkers, where the first and second polypeptide chain together form a complex containing at least three antigen binding sites, where each of the antigen binding sites contains a variable domain from the first polypeptide chain and a variable domain from the second polypeptide chain, where the first nucleic acid and the second nucleic acid are coexpressed when the episome is transformed into a host cell. The episome may be a plasmid or a cosmid. Also provided is a host cell containing a nucleic acid, a expression cassette and/or an episome as described above. The host cell may be, for example, *E. coli*, yeast, a plant cell and a mammalian cell.

Also provided are methods of preparing a polyvalent protein complex, containing culturing a host cell as described above. The host cell may be, for example, a murine myeloma cell line. The episome may contain the plasmid is pdHL2.

Other aspects and advantages of the present invention are described further in the following detailed description of preferred embodiments of the present invention.

BRIEF DESCRIPTION OF THE DRAWINGS

FIG. 1 Panel A shows an expression cassette in BS14HP-GAP+ vector, which codes for two species of mRNA synthesized from the constitutive GAP promoters. See SEQ ID NOS 19, 17, 20, 18, 19 and 20, respectively, in order of appearance, for the disclosed peptides.

Panel B shows a drawings of the two mature heterologous polypeptides, h679$V_H$-GGGGS-hMN-14$V_K$-LEGGGS-hMN-14$V_H$-6His (Left) (residues 8-270 of SEQ ID NO: 1) and hMN-14$V_K$-GGGQFM-hMN-14$V_H$-GGGGS-h679$V_K$-6His (Right) (residues 7-363 of SEQ ID NO: 2), following cleavage of the α factor signal peptides by Kex2 protease.

Panel C shows a drawing of a trivalent protein structure formed by the heterodimerization of polypeptides 1 and 2 possessing two binding sites for CEA and one for HSG.

Panel D shows the amino acid sequence (SEQ ID NO: 1) and cDNA sequence (SEQ ID NO: 9) of EAEAEFM-h679VH-GGGGS-hMN-14VK-LEGGGS-hMN-14VH-6His (SEQ ID NO: 1).

Panel E shows the amino acid sequence (SEQ ID NO: 2) and cDNA sequence (SEQ ID NO: 10) of EAEAEF-hMN-14VK-GGGQFM-hMN-14VH-GGGGS-h679VK-6His (SEQ ID NO: 2).

Figure 2:
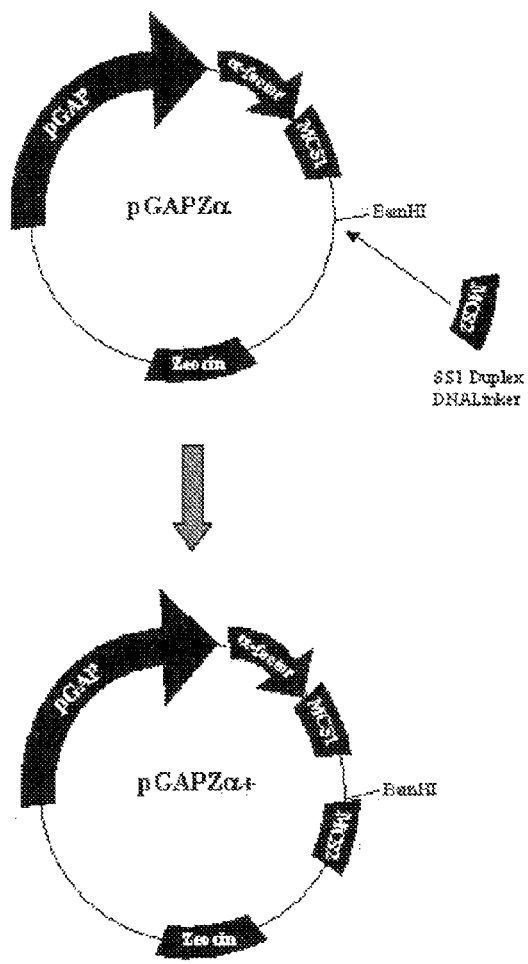

FIG. 2 depicts the construction of the modified *Pichia* expression vector pGAPZα+ used for the co-expression of two heterologous polypeptides from the same host cell.

Figure 3:
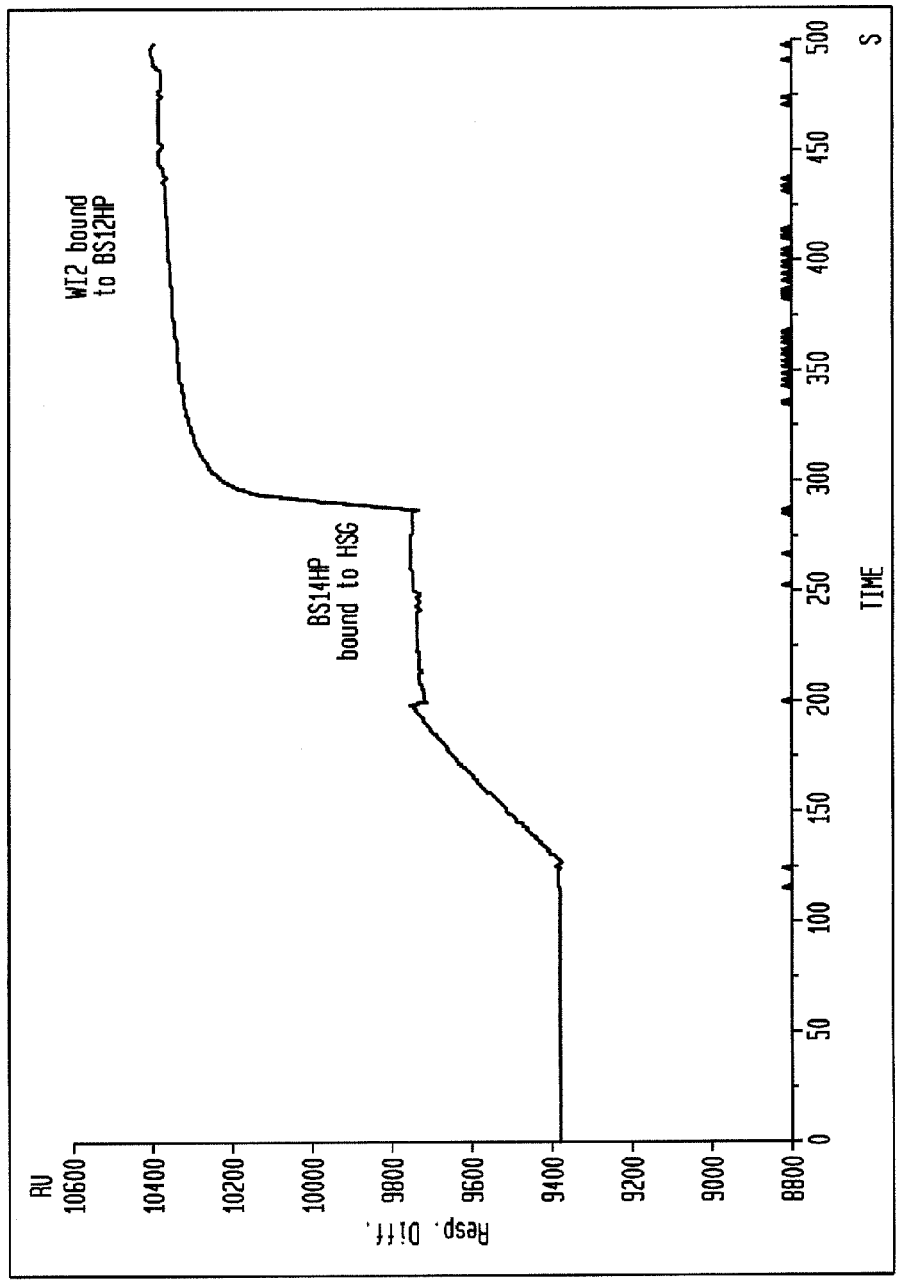

FIG. 3 shows one of many BIAcore sensorgrams used to evaluate expression of BS14HP in the culture media of *Pichia pastoris* clones. Following growth to stationary phase, culture media was diluted ten-fold in BIAcore eluent buffer and injected over an HSG-coupled sensorchip. A subsequent injection of W12 IgG (anti-id to hMN-14) confirmed the bispecificity of the samples.

Figure 4:
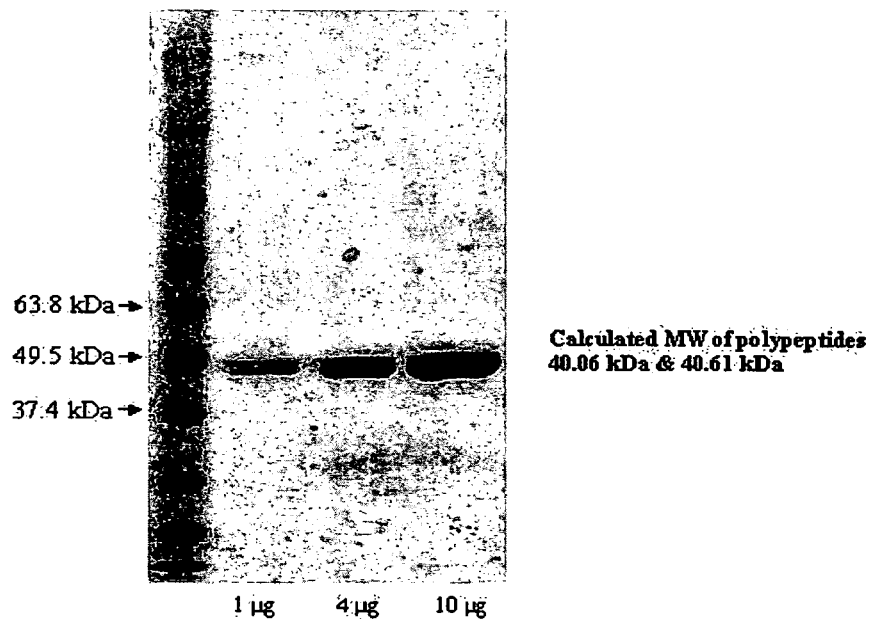

FIG. 4 shows a Coomassie blue-stained SDS-PAGE gel of BS14HP. Purified protein samples were subjected to reducing SDS-PAGE on 4-20% polyacrylamide Tris-Glycine gels. 1, 4 and 10 μg were loaded in indicated lanes. Arrows indicate the positions of molecular weight standards.

Figure 5:
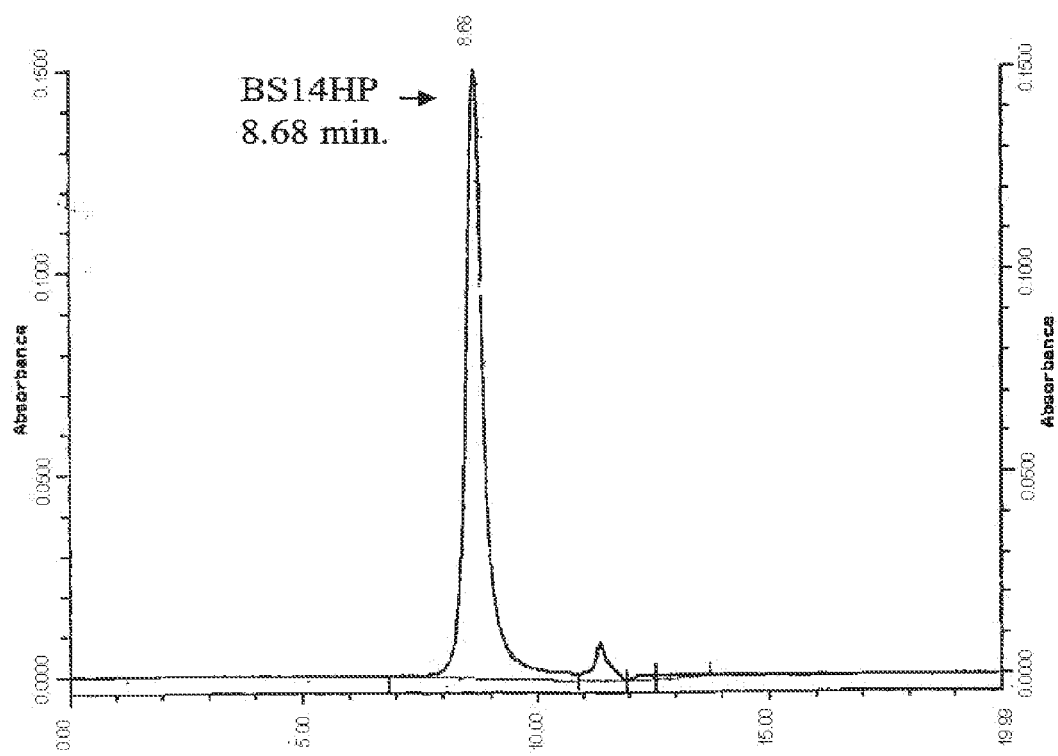

FIG. 5 shows the size exclusion HPLC profile of purified BS14HP.

FIG. 6 (a) shows a graphical representation of the results of a competitive ELISA experiment. HRP-conjugated hMN14 IgG (1 nM) was mixed with either BS14HP, BS1.5H (a bispecific diabody, monovalent for CEA and monovalent for HSG, derived from the same variable domains as BS14HP) or hMN14 F(ab')$_2$ at concentrations ranging from 1-250 nM, prior to incubation in CEA-coated (0.5 μg/well) wells. The % inhibition is plotted vs. nM concentration of sample. The 50% inhibitory concentration ($IC_{50}$) is given for each and (b) shows the results of SE-HPLC analysis of BS14HP immunoreactivity with CEA.

Figure 7:
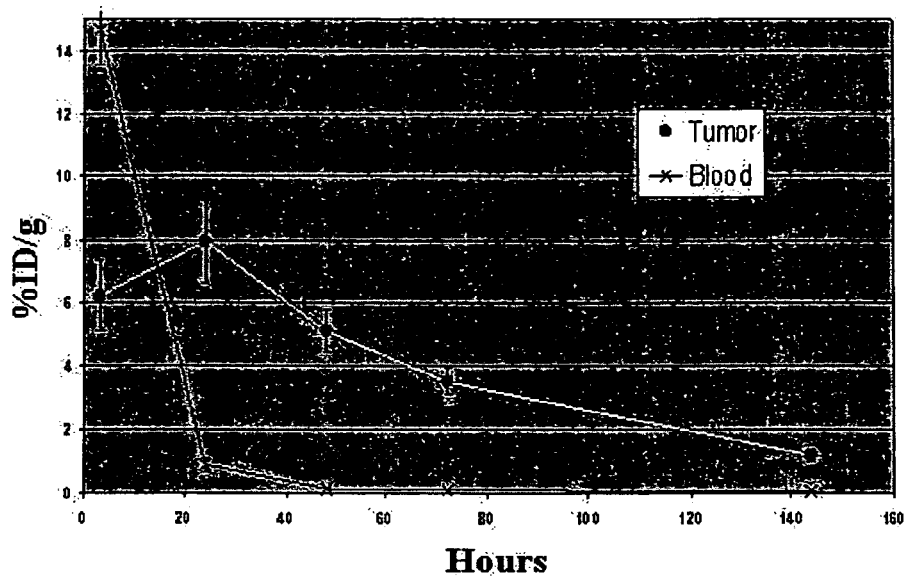

FIG. 7 shows a graphical representation of the tumor residence and blood clearance of $^{125}$I labeled BS14HP in GW39 tumor bearing nude mice. The % injected dose/gram (% ID/g) is plotted versus time (hours).

Figure 8:
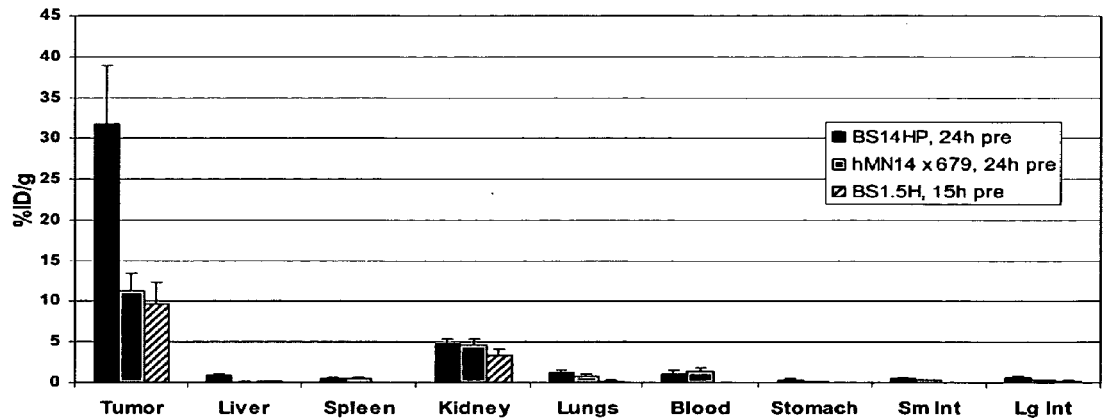
Figure 8C:
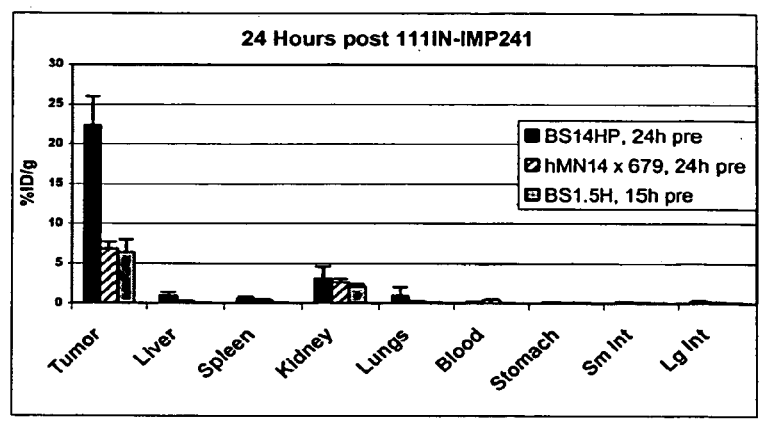

FIG. 8 shows the biodistribution (A) and tumor/non-tumor ratios after 3 hours (B) of $^{111}$In-IMP-241 in GW-39 tumor bearing mice pretargeted with three bispecific constructs and (C) and tumor/non-tumor ratios after 24 hours. Standard deviations are shown as error bars (A and C) or as in parentheses (B).

Figure 9A:
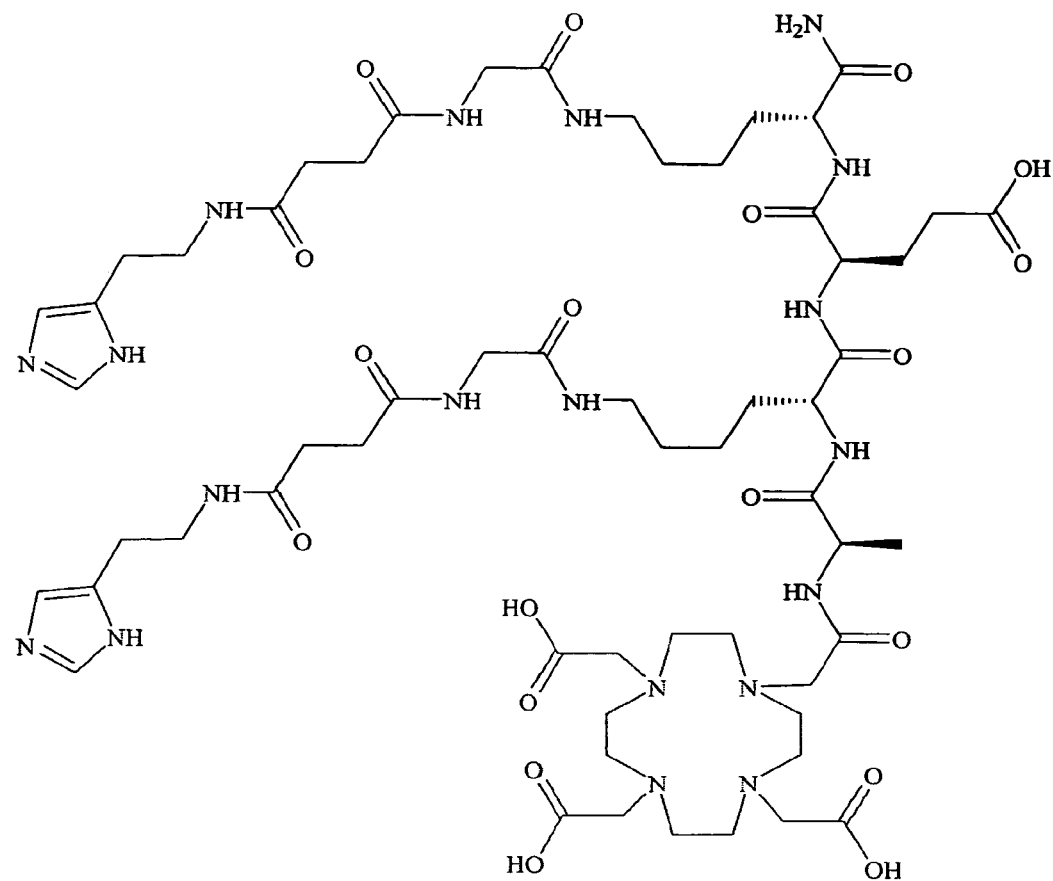
Figure 9B:
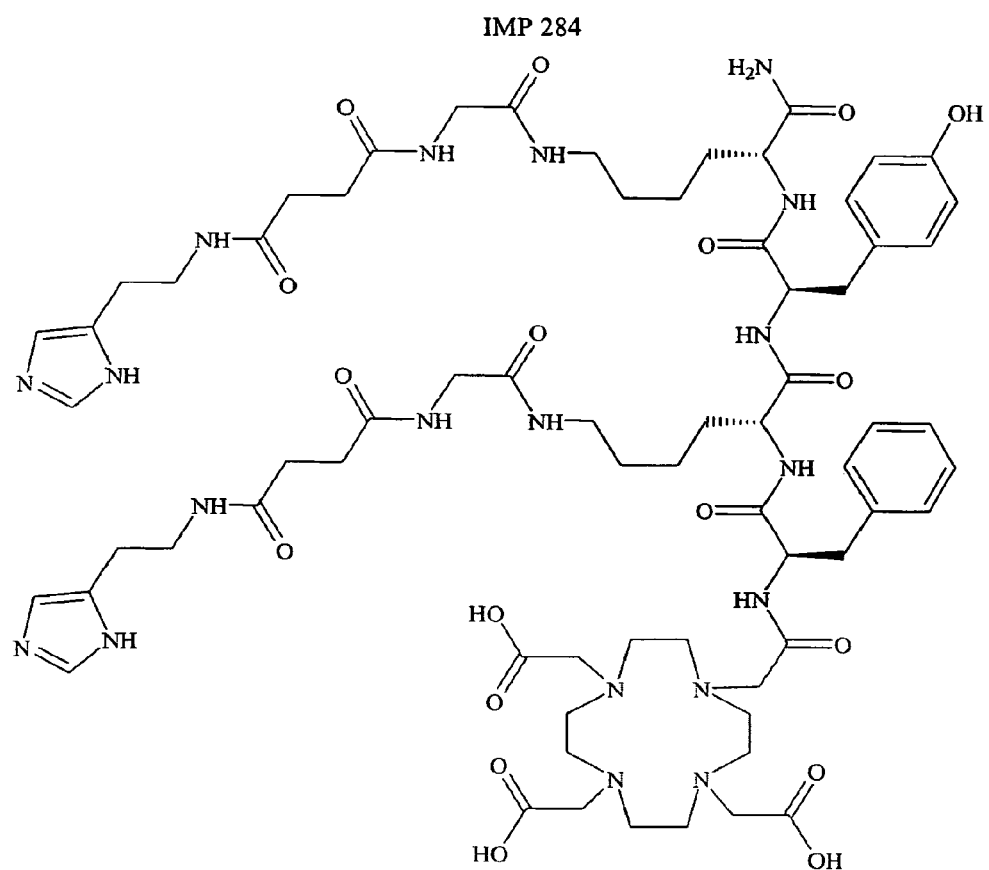
Figure 9C:
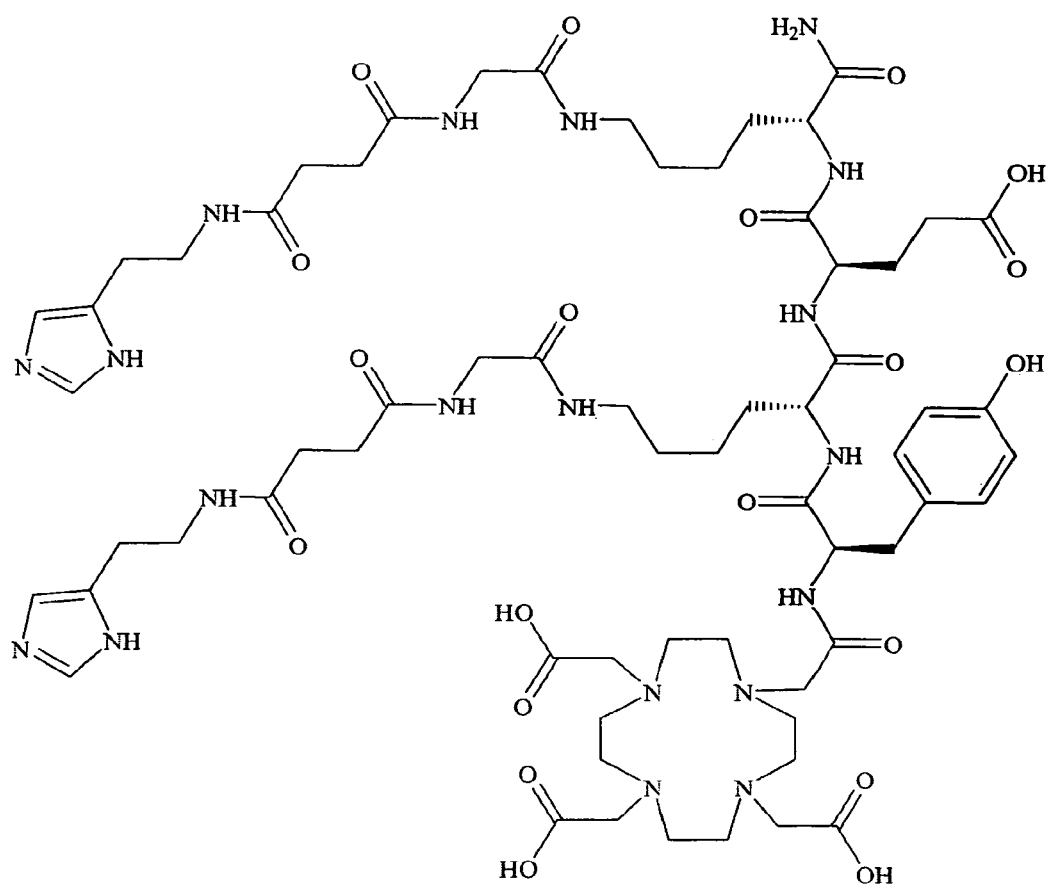

FIG. 9 panel A shows the molecular structure of IMP 281, panel B shows the molecular structure if IMP 284, panel C shows the figure of IMP 288.

FIG. 10 depicts (A) features of the SV3 shuttle vector and (B) features of the ORF/polypeptide 1 and ORF/Polypeptide 2 (SEQ ID NOS 1 & 2, respectively). The polyhistidine tag in FIG. 10A is shown in SEQ ID NO: 20.

FIG. 11 is a schematic representation of hBS14-pDHL2 expression vector.

FIG. 12 depicts the results of MTX amplification of hBS14 SP2/0 clone 1H6.

FIG. 13 depicts the results of SE-HPLC analysis of purified hBS14.

FIG. 14 depicts the results of SDS-PAGE analysis of purified hBS14.

FIG. 15 depicts the results of IEF analysis of purified hBS14.

FIG. 16 depicts the results of BIAcore analysis of hBS14.

FIG. 17 depicts the results of BIAcore analysis of HSG binding of hBS14 produced in either SP2/0 or YB2/0 cells.

Figure 18:
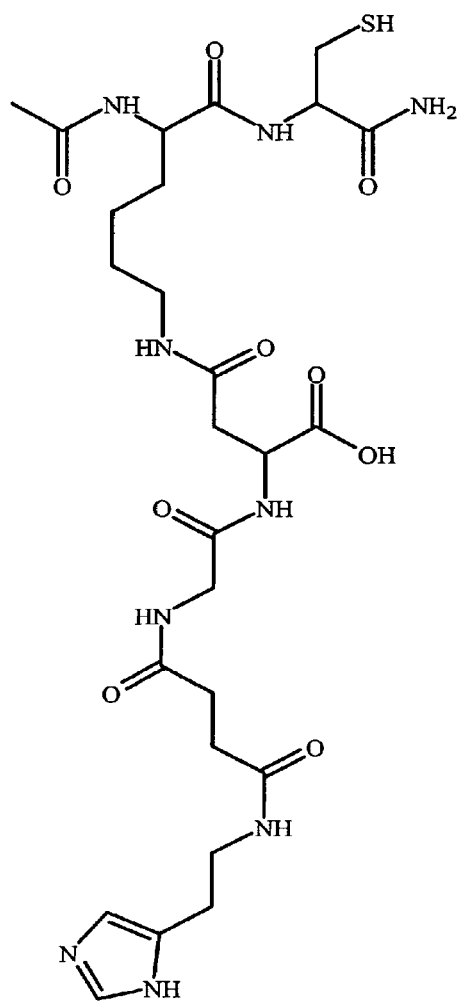

FIG. 18 shows the structure of the peptide IMP 291.

Figure 19:
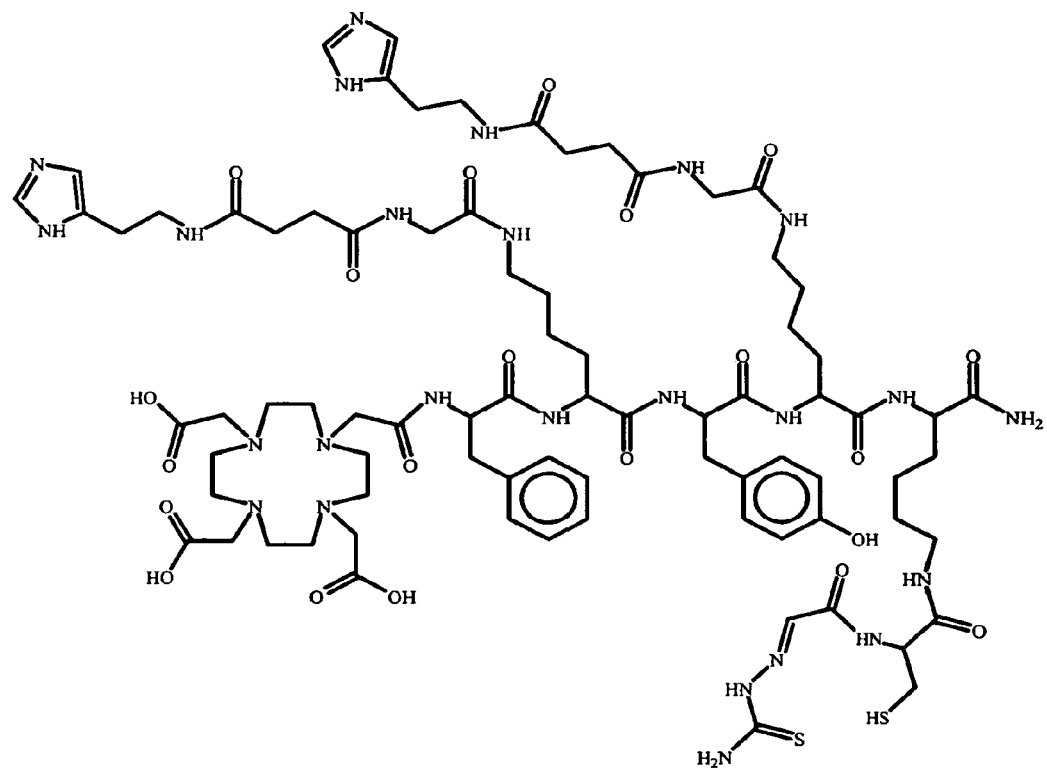

FIG. 19 shows the structure of the peptide IMP 245.

FIG. 20 shows the tumor uptake of 125I-hBS14 and $^{99m}$Tc-IMP-245 in mice when the hBS14 was given 4 hrs (top panel) or 24 hrs (bottom panel) to clear prior to administration of peptide (Groups I and II respectively).

FIG. 21 the top panel shows the tumor uptake of $^{125}$I-hBS14 and $^{99m}$Tc-IMP-245 in mice given 48 hrs to clear the hBS14 prior the administration of the peptide (Group III). The bottom panel shows peptide uptake in imaged mice at 24 hr post-injection.

FIG. 22 is a table showing percent ID/g and tumor/non-tumor ratios of $^{99m}$Tc-IMP-245 peptide at 1 h post injection.

Figure 23:
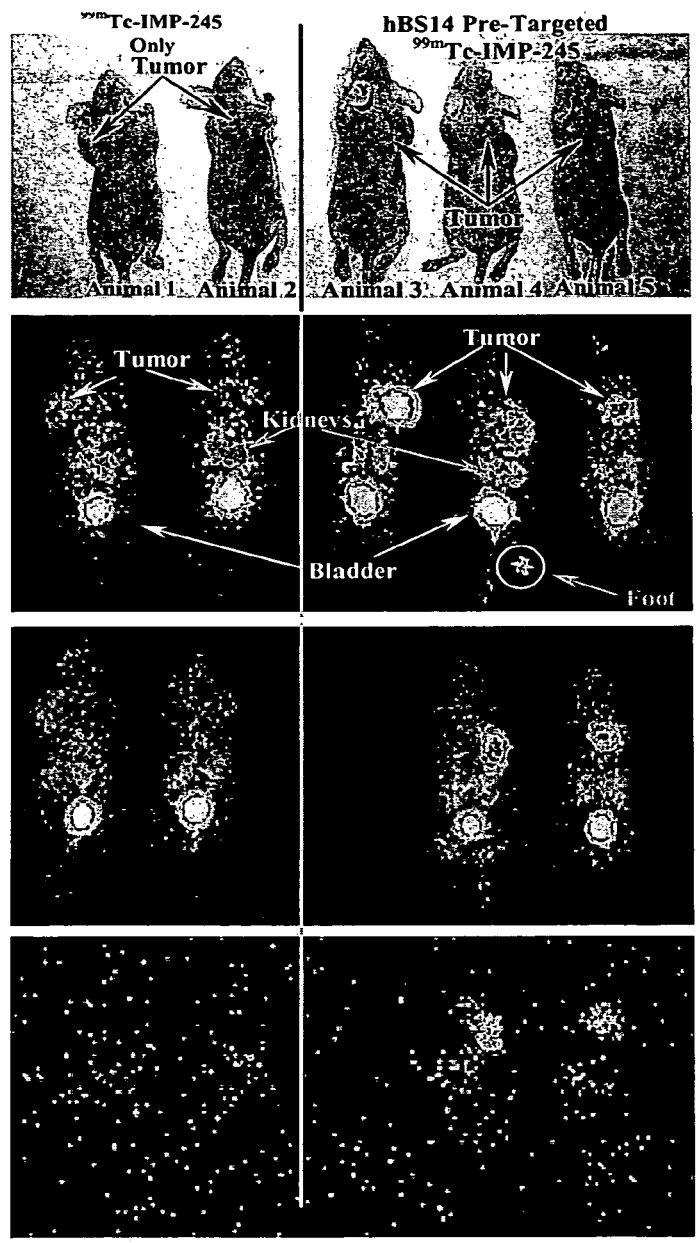

FIG. 23 shows imaging data in mice. The first pair of images shows the location of the tumors in the mice. The second pair of images shows the image at 1 hr post-peptide administration. The third pair of images show imaging data at 3 hrs post-peptide administration. The final pair of images shows the image at 24 hrs post-peptide administration.

DETAILED DESCRIPTION OF THE INVENTION

Definitions

As used herein, the term "engineered antibody" encompasses all biochemically or recombinately produced functional derivatives of antibodies. A protein is a functional derivative of an antibody if it has at least one antigen binding site (ABS) or a complementarity-determining region (CDR) that when combined with other CDR regions (on the same polypeptide chain or on a different polypeptide chain) can form an ABS. The definition of engineered antibody would include, at least, recombinant antibodies, tagged antibodies, labeled antibodies, Fv fragments, Fab fragments, recombinant (as opposed to natural) multimeric antibodies, single chain antibodies, diabodies, triabodies, tetravalent multimers (dimer of diabodies), pentavalent multimers (dimer of diabody and triabody), hexavalent multimers (dimer of triabodies) and other higher multimeric forms of antibodies.

As used herein, the term "single-chain antibody (scFv)," refers to engineered antibody constructs prepared by isolating the binding domains (both heavy and light chain) of a binding antibody, and supplying a linking moiety which permits preservation of the binding function. This forms, in essence, a radically abbreviated antibody, having only the variable domain necessary for binding the antigen. Determination and construction of single chain antibodies are described in many prior publications including U.S. Pat. No. 4,946,778; Bird et al., Science 242:423 (1988) and Huston et al., Proc. Nat'l Acad. Sci. USA 85:5879 (1988).

The term "humanized" means that at least a portion of the framework regions of an immunoglobulin or engineered antibody construct (including the PPC of this invention that comprise an immunoglobulin or engineered antibody) is derived from human immunoglobulin sequences. It should be clear that any method to humanize antibodies or antibody constructs, as for example by variable domain resurfacing as described by Roguska et al., (1994) Proc. Natl. Acad. Sci. USA 91: 969-973 would be applicable to the PPC of this invention. Alternatively, CDR grafting (also called CDR shuffling) or reshaping as reviewed by Hurle and Gross ((1994) Curr. Opin. Biotech. 5:428-433), can be used. Manipulation of the complementarity-determining regions (CDR) is a way of achieving humanized antibodies. The use of antibody components derived from humanized monoclonal antibodies obviates potential problems associated with the immunogenicity of murine constant regions. See, for example, U.S. Pat. Nos. 5,874,540 and 6,254,868. General techniques for cloning murine immunoglobulin variable domains are described, for example, by the publication of Orlandi et al., Proc. Nat'l Acad. Sci. USA 86: 3833 (1989). Techniques for producing humanized MAbs are described, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech 12: 437 (1992), Singer et al., J. Immun. 150: 2844 (1993), Winter & Milstein, Nature 349:293 (1991).

The terms "recombinant nucleic acid" or "recombinantly produced nucleic acid" refer to nucleic acids such as DNA or RNA which has been isolated from its native or endogenous source and modified either chemically or enzymatically by adding, deleting or altering naturally-occurring flanking or internal nucleotides. Flanking nucleotides are those nucleotides which are either upstream or downstream from the described sequence or sub-sequence of nucleotides, while internal nucleotides are those nucleotides which occur within the described sequence or subsequence.

The term "recombinant means" refers to techniques where proteins are isolated, the cDNA sequence coding the protein identified and inserted into an expression vector. The vector is then introduced into a cell and the cell expresses the protein. Recombinant means also encompasses the ligation of coding or promoter DNA from different sources into one vector for expression of a PPC, constitutive expression of a protein, or inducible expression of a protein.

The term "promoter" refers to a DNA sequence which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter.

The term "enhancer" refers to a promoter element. An enhancer can increase the efficiency with which a particular gene is transcribed into mRNA irrespective of the distance or orientation of the enhancer relative to the start site of transcription.

"Complementary DNA (cDNA)" refers to a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complement.

"Expression" refers to the process by which a polypeptide is produced from a structural gene. The process involves transcription of the gene into mRNA and the translation of such mRNA into polypeptide(s).

"Cloning vector" refers to a DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene which is suitable for use in the identification and selection of cells transformed with the cloning vector. Marker genes typically include genes that provide tetracycline resistance or ampicillin resistance.

"Expression vector" refers to a DNA molecule comprising a cloned structural gene encoding a foreign protein which provides the expression of the foreign protein in a recombinant host. Typically, the expression of the cloned gene is placed under the control of (i.e., operably linked to) certain regulatory sequences such as promoter and enhancer sequences. Promoter sequences may be either constitutive or inducible.

"Recombinant Host" or "Host cell" refers to a prokaryotic or eukaryotic cell which contains either a cloning vector or expression vector. This term is also meant to include those prokaryotic or eukaryotic cells that have been genetically engineered to contain the cloned gene(s) in the chromosome or genome of the host cell. The host cell is not limited to a unicellular organism such as *E. coli* and yeast. Cells from multicellular organisms such as mammals, insects, and plants are also contemplated as host cells in the context of this invention. For examples of suitable hosts, see Sambrook et al., MOLECULAR CLONING: A LABORATORY MANUAL, Second Edition, Cold Spring Harbor Laboratory, Cold Spring Harbor, N.Y. (1989). A mammalian host cell may be of any mammalian origin and include, at least cells of human, bovine, canine, murine, rattus, equine, porcine, feline and non-human primate origin.

A "tumor-associated antigen" is a protein normally not expressed, or expressed at very low levels, by a normal cell. However, in a neoplastic or preneoplastic cell (a cell predisposed to becoming a cancer cell), the tumor-associated antigen is expressed at a level that is higher than that of a normal cell. The preferred tumor-associated antigens are the ones that are expressed at very high levels in neoplastic and preneoplastic cells but at very low levels or not expressed in normal cells. "Antigens" and "tumor-associated antigens" are well known and include at least α-fetoprotein, A3, A33 (GI cancers, particularly colon cancer), CA125, carcinoembryonic antigen (CEA), CD19, CD20, CD21, CD22, CD23, CD30, CD33, CD45, CD52 (associated with chronic lymphocytic leukemia and other lymphomas), CD74, CD66, CD80, colon-specific antigen-p (CSAp), EGFR, EGP-1, EGP-2, folate receptor, HER2/neu, HLA-DR, human chorionic gonadrotropin, Ia, IL-2, IL-6 (prostate cancer), insulin-like growth factor, KS-1, Le(y), MAGE, MUC1, MUC2, MUC3, MUC4, necrosis antigens, PAM-4, placental growth factor, prostatic acid phosphatase (PAP), prostate specific antigen (PSA), PSMA, S100, T10, TAC, TAG-72, tenascin, and VEGF. Furthermore, the ABS of the invention includes, at least, an ABS that binds to an epitope of the above listed antigens. Tumor-associated antigens may be either produced by the tumor cells themselves or by adjacent structures, such as the tumor's vascular endothelium. B-cell, T-cell and other such "lineage" antigens which are present in both normal and malignant cell types may still be useful targets because of a differential expression by or sensitivity of the malignant cells to antibodies against these lineage antigens (e.g., CD19, CD20, CD21, CD22 in normal and malignant B cells). Many other illustrations of tumor-associated antigens are known to those of skill in the art. See, e.g., Urban et al., Ann. Rev. Immunol. 10:617 (1992). The list above is illustrative only and cites the cancers most closely associated to the tumor-associated antigen. In most cases, each tumor-associated antigen may have up to 2, 3, 4, 5, 6 or more epitopes.

Known tumors that are associated with tumor-associated antigens include, at least, carcinomas, melanomas, sarcomas, gliomas, myelomas, leukemias and lymphomas.

As used herein, an "infectious agent" and "pathogen" denotes both microbes and parasites. A "microbe" includes viruses, bacteria, rickettsia, mycoplasma, protozoa, fungi and like microorganisms. A "parasite" denotes infectious, generally microscopic or very small multicellular invertebrates, or ova or juvenile forms thereof, which are susceptible to antibody-induced clearance or lytic or phagocytic destruction, such as malarial parasites, spirochetes, and the like. Examples of infectious agents include, for example, a fungus, virus, parasite, bacterium, protozoan, or mycoplasm. The fungus may be from the species of *Microsporum, Trichophyton, Epidermophyton, Sporothrix schenckii, Cyrptococcus neoformans, Coccidioides immitis, Histoplasma capsulatum, Blastomyces dermatitidis*, or *Candida albicans*. The virus may be from the species of human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus. The bacterium may be, for example, *Anthrax bacillus, Streptococcus agalactiae, Legionella pneumophilia, Streptococcus pyogenes, Escherichia coli, Neisseria gonorrhoeae, Neisseria meningitidis, Pneumococcus, Hemophilis influenzae* B, *Treponema pallidum*, Lyme disease spirochetes, *Pseudomonas aeruginosa, Mycobacterium leprae, Brucella abortus, Mycobacterium tuberculosis* and *Tetanus toxin*. The parasite may be a helminth or a malarial parasite. The protozoan may be *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* or *Mesocestoides corti*. The mycoplasma may be *Mycoplasma arthritidis, Mycoplasma hyorhinis, Mycoplasma orale, Mycoplasma arginini, Acholeplasma laidlawii, Mycoplasma salivarum*, and *Mycoplasma pneumoniae*. Other examples of infectious agents and pathogens that may be treated by the product (PPC) and methods of this invention are contained in the second and subsequent editions of Davis et al, "Microbiology" (Harper & Row, New York, 1973 and later), and are well known to the ordinary skilled art worker.

The term "treating" in its various grammatical forms in relation to the present invention refers to preventing, curing, reversing, attenuating, alleviating, minimizing, suppressing or halting the deleterious effects of a disease state, disease progression, disease causative agent (e.g., bacteria or viruses) or other abnormal condition. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Unless otherwise noted, use of the term "antibody" or "immunoglobulin" herein will be understood to include antibody fragments and functional derivatives (i.e., engineered antibody) thereof. Antibodies can be whole immunoglobulin of any class, e.g., IgG, IgM, IgA, IgD, IgE, or hybrid antibodies with dual or multiple antigen or epitope specificities, or fragments, e.g., F(ab')$_2$, F(ab)$_2$, Fab', Fab$_1$ and the like, including hybrid fragments. Functional derivatives include engineered antibodies.

The terms "recombinant protein," "recombinantly produced protein" or "recombinantly produced immunotoxin" refer to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The term "selective cytotoxic reagent" refers to a compound that when added to a population of different cells, e.g., within an organism, kills one type of cell in the population based on some physical characteristic of the cell, i.e., a surface ligand or marker to which the cytotoxic reagent binds and then becomes internalized.

The term "surface marker" refers to various constituents, such as a protein, carbohydrate, or glycoprotein, that are present on the surface of a cell. Different types of cells express different cell surface markers and therefore cells can be identified by the presence of a cell surface marker. For example, B cells express CD19, CD20 (See, Ansell et al., J. Clin. Oncology, 20:3885-3890 (2002) and Witzig et al., J. Clin. Oncology 20:2453-2463) and CD22. Thus, the binding of an antibody that recognizes CD19, CD20 or CD22 identifies that cell as a B cell, either normal or malignant. As another example, the B-cell may be a multiple myeloma, in which case the B cells may express the tumor-associated antigen MUC1 or CD74. B cell surface markers may be used for ablation of B cells and B cell tumor-associated antigens may be used to ablate B cell tumors such as the multiple myeloma described above.

The term "CD22" refers to a lineage-restricted B-cell antigen belonging to the Ig superfamily, is expressed on the surface of many types of malignant B cells, including but not limited to, acute lymphocytic leukemia (B-ALL), chronic B-lymphocytic cells (B-CLL), B lymphoma cells such as Burkitt's, AIDS-associated and follicular lymphomas, and hairy cell leukemias, as well as on normal mature B lymphocytes. See, U.S. Pat. Nos. 6,183,744 and 6,306,393. CD22 is not expressed in early stages of B-cell development, nor is it found on the surface of stem cells or terminal stage plasma cells. Vaickus et al., Crit. Rev. Oncol/Hematol. 11:267-297 (1991). Additionally, no shed antigen is detected in normal human serum or serum from patients with CLL. Li et al., Cell. Immunol. 118:85-99 (1989).

According to the specific case, the "therapeutically effective amount" of an agent should be determined as being the amount sufficient to improve the symptoms of the patient in need of treatment or at least to partially arrest the disease and its complications. Amounts effective for such use will depend on the severity of the disease and the general state of the patient's health. Single or multiple administrations may be required depending on the dosage and frequency as required and tolerated by the patient.

As used herein, the term "a method to detect" refers to any assay (including immunoassays and calorimetric assays) known in the art for the measurement of a detectable label. These assays include, at least, assays utilizing biotin and avidin (including streptavidin), ELISA's and immunoprecipitation, immunohistochemical techniques and agglutination assays. A detailed description of these assays is given in WO 96/13590 to Maertens & Stuyver. The term "biological sample" relates to any possible sample taken from an animal (including humans), such as blood (which also encompasses serum and plasma samples), sputum, cerebrospinal fluid, urine, lymph or any possible histological section, and other body fluid. Detection may also include methods of imaging a lesion, such as with immunoscintigraphy, computed tomography (CT), ultrasonography, X-rays, and the like.

The terms "binding specificity," "specifically binds to" or "specifically immunoreactive with," when referring to a protein or ABS of the invention, refers to a binding reaction which is determinative of the presence of the protein or carbohydrate in the presence of a heterogeneous population of proteins and other biologics. Thus, under designated immunoassay conditions, the specified PPC bind to a particular protein or carbohydrate and do not bind in a significant amount to other proteins or carbohydrates present in the sample. Specific binding to a PPC under such conditions may require a PPC selected for its specificity towards a particular protein or carbohydrate. For example, PPCs specific for the CD22 antigen may be selected to provide PPC that are specifically immunoreactive with CD22 protein and not with other proteins. A variety of immunoassay formats may be used to select PPC specifically immunoreactive with a particular protein or carbohydrate. For example, solid-phase ELISA immunoassays are routinely used to select antibodies specifically immunoreactive with a protein or carbohydrate. See Harlow & Lane, Antibodies, A Laboratory Manual, Cold Spring Harbor Publication, New York (1988) for a description of immunoassay formats and conditions that can be used to determine specific immunoreactivity.

The terms "isolated" or "substantially purified," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

The terms "nucleic acid encoding" or "nucleic acid sequence encoding" refer to a nucleic acid which directs the expression of a specific protein or peptide. The nucleic acid sequences include both the DNA strand sequence that is transcribed into RNA and the RNA sequence that is translated into protein. The nucleic acid sequences include both full length nucleic acid sequences as well as shorter sequences derived from the full length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex form.

"Pharmaceutical composition" refers to formulations of various preparations. Parenteral formulations are known and are preferred for use in the invention. The formulations containing therapeutically effective amounts of the immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg or more.

The term "crosslinker" is well known in the art and include at least ABH(21509), AEDP(22101), AMAS(22295), ANB-NOS(21451), APDP(27720), APG(20108), ASBA(21512), BASED(21564), BMB(22331), BMDB(22332), BMH(22330), BMOE(22323), BMPA(22296), BMPH(22297), BMPS(22298), BM[PEO]$_3$(22336), BM[PEO]$_4$(22337), BSOCOES(21600), BS3(21580), DFDNB(21525), DMA (20663), DMP(21666), DMS (20700), DPDPB(21702), DSG (20593), DSP(22585), DSS(21555), DST(20589), DTBP (20665), DTME(22335), DTSSP(21578), EDC(22980), EGS (21565), EMCA(22306), EMCH(22106), EMCS(22308), GMBS(22309), HBVS(22334), KMUA(22211), KMUH (22111), LC-SMCC(22362), LC-SPDP(21651), MBS (22311), M2C2H(22303), MPBH(22305), MSA(22605), NHS-ASA(27714), PDPH(22301), PMPI(28100), SADP (21533), SAED(33030), SAND(21549), SANPAH(22600), SASD(27716), SATA(26102), SATP(26100), SBAP(22339), SFAD(27719), SIA(22349), SIAB(22329), SMCC(22360), SMPB(22416), SMPH(22363), SMPT(21558), SPDP (21857), Sulfo-BSOCOES(21556), Sulfo-DST(20591), Sulfo-EGS(21566), Sulfo-EMCS(22307), Sulfo-GMBS (22324), Sulfo-HSAB(21563), Sulfo-KMUS(21111), Sulfo-LC-SPDP(21650), Sulfo-MBS(22312), Sulfo-NHS-LC-ASA(27735), Sulfo-SADP(21553), Sulfo-SANPAH (22589), Sulfo-SIAB(22327), Sulfo-SMCC(22322), Sulfo-SMPB(22317), Sulfo-LC-SMPT(21568), Sulfo-SBED (33033), SVSB(22358), TFCS(22299), THPP(22607), TMEA(33043), and TSAT(33063) (Pierce Chemical, Rockford, Ill. catalog number in parenthesis). See, also U.S. Pat. No. 4,680,338 and provisional patent application 60/436,359 filed Dec. 24, 2002, for additional linker descriptions.

The term "chemotherapeutic agent" may be any chemotherapeutic agent known in the art and includes, at least, taxanes, nitrogen mustards, ethylenimine derivatives, alkyl sulfonates, nitrosoureas, triazenes; folic acid analogs, pyrimidine analogs, purine analogs, vinca alkaloids, antibiotics, enzymes, platinum coordination complexes, substituted urea, methyl hydrazine derivatives, adrenocortical suppressants, or antagonists. Specifically, the chemotherapeutic agent may be from the group of steroids, progestins, estrogens, antiestrogens, and androgens. More specifically, the chemotherapeutic agent may be azaribine, bleomycin, bryostatin-1, busulfan, carmustine, celebrex, chlorambucil, cisplatin, CPT-11, cyclophosphamide, cytarabine, dacarbazine, dactinomycin, daunorubicin, dexamethasone, diethylstilbestrol, doxorubicin, ethinyl estradiol, etoposide, fluorouracil, fluoxymesterone, gemcitabine, hydroxyprogesterone caproate, hydroxyurea, L-asparaginase, leucovorin, lomustine, mechlorethamine, medroprogesterone acetate, megestrol acetate, melphalan, mercaptopurine, methotrexate, methotrexate, mithramycin, mitomycin, mitotane, phenyl butyrate, prednisone, procarbazine, semustine streptozocin, tamoxifen, taxanes, taxol, testosterone propionate, thalidomide, thioguanine, thiotepa, uracil mustard, vinblastine, and vincristine.

The term "cytotoxic agents" includes all known cytotoxic and cytostatic agents. Examples of these agents are listed in Goodman et al., "The Pharmacological Basis of Therapeutics," Sixth Edition, A. G. Gilman et al, eds./Macmillan Publishing Co. New York, 1980, as well as a more current edition (See also, U.S. Pat. Nos. 6,083,477 and 6,395,276) These agents include, at least the following: antiapoptotic agents, antimetabolites, alkaloids, antimitotic agents, enzyme inhibitors, COX-inhibitors, chemotherapeutic agents; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone). Other examples of cytotoxic agents include ricin, abrin, ribonuclease, DNase I, Staphylococcal enterotoxin-A, pokeweed antiviral protein, gelonin, diphtherin toxin, Pseudomonas exotoxin, Pseudomonas endotoxin and radionuclides. See, for example, Pastan et al., Cell 47:641 (1986), and Goldenberg, Calif.—A Cancer Journal for Clinicians 44:43 (1994). Other suitable toxins are known to those of skill in the art.

Therapeutic agents are as defined in the specification but include at least, an immunoe modulator, an enzyme, a hormone.

Radionuclide include any radioactive isotope useful for medical diagnostic, therapeutic and imaging methods (i.e., detectable labels). Examples of radionuclides include $^{225}$Ac, $^{111}$Ag, $^{72}$As, $^{77}$As, $^{211}$At, $^{198}$Au, $^{199}$Au, $^{212}$Bi, $^{213}$Bi, $^{75}$Br, $^{76}$Br, $^{11}$C, $^{55}$Co, $^{62}$Cu, $^{67}$Cu, $^{166}$Dy, $^{169}$Er, $^{18}$F, $^{52}$Fe, $^{59}$Fe, $^{67}$Ga, $^{68}$Ga, $^{154-158}$Gd, $^{166}$Ho, $^{120}$I, $^{121}$I, $^{123}$I, $^{124}$I, $^{125}$I, $^{131}$I, $^{110}$In, $^{111}$In, $^{194}$Ir, $^{177}$Lu, $^{51}$Mn, $^{52m}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{142}$Pr, $^{143}$Pr, $^{223}$Ra, $^{82m}$Rb, $^{186}$Re, $^{188}$Re, $^{189}$Re, $^{105}$Rh, $^{47}$Sc, $^{75}$Se, $^{153}$Sm, $^{83}$Sr, $^{89}$Sr, $^{161}$Tb, $^{94m}$Tc, $^{99m}$Tc, $^{86}$Y, $^{90}$Y and $^{89}$Zr. Of these radionuclides $^{225}$Ac, $^{111}$Ag, $^{77}$As, $^{211}$At, $^{198}$Au, $^{199}$Au, $^{212}$Bi, $^{213}$Bi, $^{62}$Cu, $^{64}$Cu, $^{67}$Cu, $^{166}$Dy, $^{169}$Er, $^{59}$Fe, $^{67}$Ga, $^{166}$Ho, $^{125}$I, $^{131}$I, $^{111}$In, $^{194}$Ir, $^{177}$Lu, $^{99}$Mo, $^{32}$P, $^{33}$P, $^{211}$Pb, $^{212}$Pb, $^{109}$Pd, $^{149}$Pm, $^{142}$Pr, $^{143}$Pr, $^{223}$Ra, $^{186}$Re, $^{188}$Re, $^{189}$Re, $^{105}$Rh, $^{47}$Sc, $^{75}$Se, $^{153}$Sm, $^{89}$Sr, $^{161}$Tb and $^{90}$Y are particularly useful as therapeutic radionuclides and therapeutic cations. Further, $^{72}$As, $^{75}$Br, $^{76}$Br, $^{11}$C, $^{55}$Co, $^{62}$Cu, $^{64}$Cu, $^{67}$Cu, $^{18}$F, $^{52}$Fe, $^{67}$Ga, $^{68}$Ga, $^{154-158}$Gd, $^{120}$I, $^{123}$I, $^{124}$I, $^{125}$I, $^{131}$I, $^{110}$In, $^{111}$In, $^{177}$Lu, $^{51}$Mn, $^{52}$Mn, $^{13}$N, $^{15}$O, $^{32}$P, $^{223}$Ra, $^{82}$Rb, $^{186}$Re, $^{188}$Re, $^{83}$Sr, $^{94}$Tc, $^{99}$Tc, $^{86}$Y, $^{90}$Y and $^{89}$Zr are particularly useful as diagnostic radionuclides and diagnostic cations.

"Antimicrobial agents" are any agents that has a cytotoxic or cytostatic effect on microbes. Antimicrobial agents may be conventionally classified into four main groups, based upon their affecting (1) bacterial cell-wall synthesis, (2) the cytoplasmic membrane, (3) protein synthesis, and (4) nucleic acid synthesis, and often each of these groups can be subdivided into several classes. Reviews of antimicrobial chemotherapy can be found in the chapter by M. P. E. Slack (In: Oxford Textbook of Medicine, Second Ed., Vol. 1, edited by D. J. Weatherall, J. G. G. Lidingham, and D. A. Warrell, pp. 5.35-5.53; Oxford University Press, Oxford/Melbourne/N.Y., 1987) and in Section XII, Chemotherapy of Microbial Diseases (In: Goodman and Gilman's THE PHARMACOLOGICAL BASIS OF THERAPEUTICS, 6th Ed., Goodman et al., Eds., pp. 1080-1248; Macmillan Publishing Co., New York, 1980—and also the 2001 edition). As indicated in these texts, some antimicrobial agents are selective in their toxicity, since they kill or inhibit the microorganism at concentrations that are tolerated by the host (i.e., the drug acts on microbial structures or biosynthetic pathways that differ from those of the host's cells). Other agents are only capable of temporarily inhibiting the growth of the microbe, which may resume growth when the inhibitor is removed. Often, the ability to kill or inhibit a microbe or parasite is a function of the agent's concentration in the body and its fluids.

Cytokines are known to those of skill in the art and includes, at least, "immune modulators" such as IL-1, IL-2, IL-3, IL-6, IL-10, IL-12, IL-18, IL-21, interferon-α, interferon-β, and interferon-γ.

It is understood that the definitions provided above are not mutually exclusive. For example, one molecule may be a cytotoxic agent, a radionuclide and a detectable label.

Structure of the Polyvalent Protein Complex (PPC)

The invention provides for a polyvalent protein complex (PPC) comprising two polypeptide chains generally arranged laterally to one another. Each polypeptide chain typically comprises 3 or 4 "v-regions", which comprise amino acid sequences capable of forming an antigen binding site when matched with a corresponding v-region on the opposite polypeptide chain. Up to about 6 "v-regions" can be used on each polypeptide chain, however. The v-regions of each polypeptide chain are connected linearly to one another and may be connected by interspersed linking regions. When arranged in the form of the PPC, the v-regions on each polypeptide chain form individual antigen binding sites. Thus, for example, a PPC with 4 antigen binding sites and three linking regions can be depicted as follows:

[amino terminus]-a$_1$-l$_1$-a$_2$-l$_2$-a$_3$-l$_3$-a$_4$-[carboxyl terminus]

[carboxyl terminus]-b$_1$-l$_4$-b$_2$-l$_5$-b$_3$-l$_6$-b$_4$-[amino terminus]

As shown here, the first polypeptide comprises 4 v-regions, a$_1$, a$_2$, a$_3$ and a$_4$, connected by three linker regions, l$_1$, l$_2$ and l$_3$. The second polypeptide of the PPC comprises 4 corresponding v-regions b$_1$, b$_2$, b$_3$ and b$_4$ and three interspersed linker regions, l$_4$, l$_5$ and l$_6$. The individual polypeptide chains of the PPC are bound to one another by the complementarity binding of the corresponding v-regions on each chain. Thus, as depicted above, a$_1$ binds to b$_1$, a$_2$ binds to b$_2$, a$_3$ binds to b$_3$, etc. to form the PPC.

The PPC of the invention can comprise v-regions of various amino acid sequences so long as the arrangement of corresponding v-regions on the two polypeptide chains (i.e., a$_n$ to b$_n$) provides for an antigen binding site. The binding of the corresponding v-regions forms the individual antigen binding sites of the PPC. A preferred method for forming each antigen binding site on the PPC is to arrange corresponding V$_H$ and V$_L$ regions of known antigen binding regions from antibodies or antibody fragments. However the practice of the invention is not limited to incorporation of such known antigen binding regions. If corresponding V$_H$ and V$_L$ regions are used, there are no limitations on which of the two v-regions (i.e., a$_n$ or b$_n$) encode V$_H$ or V$_L$. For example, where n=3, any combination of V$_H$ and V$_L$ listed below are possible:

| Combination | a$_1$ | a$_2$ | a$_3$ | b$_1$ | b$_2$ | b$_3$ |
|---|---|---|---|---|---|---|
| 1 | V$_H$ | V$_H$ | V$_H$ | V$_L$ | V$_L$ | V$_L$ |
| 2 | V$_H$ | V$_H$ | V$_L$ | V$_L$ | V$_L$ | V$_H$ |
| 3 | V$_H$ | V$_L$ | V$_H$ | V$_L$ | V$_H$ | V$_L$ |
| 4 | V$_L$ | V$_H$ | V$_H$ | V$_H$ | V$_L$ | V$_L$ |
| 5 | V$_H$ | V$_L$ | V$_L$ | V$_L$ | V$_H$ | V$_H$ |
| 6 | V$_L$ | V$_H$ | V$_L$ | V$_H$ | V$_L$ | V$_H$ |
| 7 | V$_L$ | V$_L$ | V$_H$ | V$_H$ | V$_H$ | V$_L$ |
| 8 | V$_L$ | V$_L$ | V$_L$ | V$_H$ | V$_H$ | V$_H$ |

As a further example, in the case where there are tour V-regions, any of the following are possible.

| Combination | a$_1$ | a$_2$ | a$_3$ | a$_4$ | b$_1$ | b$_2$ | b$_3$ | b$_4$ |
|---|---|---|---|---|---|---|---|---|
| 1 | V$_H$ | V$_H$ | V$_H$ | V$_H$ | V$_L$ | V$_L$ | V$_L$ | V$_L$ |
| 2 | V$_H$ | V$_H$ | V$_L$ | V$_H$ | V$_L$ | V$_L$ | V$_H$ | V$_L$ |
| 3 | V$_H$ | V$_L$ | V$_H$ | V$_H$ | V$_L$ | V$_H$ | V$_L$ | V$_L$ |
| 4 | V$_L$ | V$_H$ | V$_H$ | V$_H$ | V$_H$ | V$_L$ | V$_L$ | V$_L$ |
| 5 | V$_H$ | V$_L$ | V$_L$ | V$_H$ | V$_L$ | V$_H$ | V$_H$ | V$_L$ |
| 6 | V$_L$ | V$_H$ | V$_L$ | V$_H$ | V$_H$ | V$_L$ | V$_H$ | V$_L$ |
| 7 | V$_L$ | V$_L$ | V$_H$ | V$_H$ | V$_H$ | V$_H$ | V$_L$ | V$_L$ |
| 8 | V$_L$ | V$_L$ | V$_L$ | V$_H$ | V$_H$ | V$_H$ | V$_H$ | V$_L$ |
| 9 | V$_H$ | V$_H$ | V$_H$ | V$_L$ | V$_L$ | V$_L$ | V$_L$ | V$_H$ |
| 10 | V$_H$ | V$_H$ | V$_L$ | V$_L$ | V$_L$ | V$_L$ | V$_H$ | V$_H$ |
| 11 | V$_H$ | V$_L$ | V$_H$ | V$_L$ | V$_L$ | V$_H$ | V$_L$ | V$_H$ |
| 12 | V$_L$ | V$_H$ | V$_H$ | V$_L$ | V$_H$ | V$_L$ | V$_L$ | V$_H$ |
| 13 | V$_H$ | V$_L$ | V$_L$ | V$_L$ | V$_L$ | V$_H$ | V$_H$ | V$_H$ |
| 14 | V$_L$ | V$_H$ | V$_L$ | V$_L$ | V$_H$ | V$_L$ | V$_H$ | V$_H$ |
| 15 | V$_L$ | V$_L$ | V$_H$ | V$_L$ | V$_H$ | V$_H$ | V$_L$ | V$_H$ |
| 16 | V$_L$ | V$_L$ | V$_L$ | V$_L$ | V$_H$ | V$_H$ | V$_H$ | V$_H$ |

In one embodiment, one polypeptide of the PPC may be SEQ ID NO: 1 (FIG. 1D). In another embodiment, one polypeptide of the PPC may be SEQ ID NO:2 (FIG. 1E). In a preferred embodiment, one polypeptide of the PPC is SEQ ID NO:1 while the other polypeptide is SEQ ID NO:2.

Because each of the v-regions of the polypeptides of a PPC are independent, each of the antigen binding sites can independently have the same or different affinity or specificity. In separately preferred embodiments, the antigen binding sites of a PPC bind different epitopes or the same epitope. In practice of this invention, in either such embodiment, it is likely and acceptable that binding affinity for each individual antigen binding site will differ.

As noted above, a preferred embodiment of the PPC of this invention comprises known $V_H$ and $V_L$ sequences for the v-regions. For example, if it is desired for a PPC to have an ABS with the same specificity as a target antibody. The gene for the target antibody may be cloned or the target antibody may be subjected to protein sequencing. Then the $V_H$ and $V_L$ sequence of the target antibody may be determined. A nucleic acid construct may be made to coexpress both polypeptides of the PPC in a host where at least one of the PPC's antigen binding sites would comprise the corresponding $V_H$ and $V_L$ regions as the target antibody. These antigen binding sites would be expected to have similar, if not identical, antigen binding specificity and affinity with the target antibody. In the practice of this embodiment of the invention, the target antibody may be human, nonhuman or an engineered antibody. Furthermore, the antibody may be any antibody whose sequence is in the public domain.

Methods of producing a target antibody of any specificity are known in the art. For example, a monoclonal antibody may be made from an antigen. Recombinant antibody libraries expression libraries, which express a repertoire of antibodies on different host cells may be screened. Furthermore, antibodies may be purified and their protein sequences determined using antigen affinity columns.

In another embodiment of the invention, the $V_H$ and $V_L$ regions of the PPC may be derived from a "humanized" monoclonal antibody or from a human antibody. Alternatively, the $V_H$ and/or $V_L$ regions may comprise a sequence derived from human antibody fragments isolated from a combinatorial immunoglobulin library. See, for example, Barbas et al., METHODS: A companion to Methods in Enzymology 2: 119 (1991), and Winter et al., Ann. Rev. Immunol. 12: 433 (1994). Cloning and expression vectors that are useful for producing a human immunoglobulin phage library can be obtained, for example, from STRATAGENE Cloning Systems (La Jolla, Calif.).

The human antibody $V_H$ or $V_L$ sequence may be derived from a human monoclonal antibody produced in a mouse. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7: 13 (1994), Lonberg et al., Nature 368: 856 (1994), and Taylor et al., Int. Immun. 6: 579 (1994).

The linker regions may comprise any amino acid sequence that are of sufficient length to allow for arrangement of corresponding v-regions on the individual polypeptide chains of the PPC into antigen binding sites (i.e. $a_1/b_1$, $b_2/a_2$, etc.), for example, due to steric constraints. However, the linker sequences should not be so long as to allow two adjacent v-regions on the polypeptide chains to fold back on one another (i.e., $a_1/a_2$, $b_1/b_2$, etc.). Typically, linkers longer than 10 amino acids are more likely to demonstrate folding back problems. In a preferred embodiment, the linkers comprise a polypeptide of between 3 to 8 amino acids in length. While any amino acid may be used in the linker, the preferred amino acids are those that are flexible and hydrophilic (e.g., glycine and serine). Examples of such linkers include, for example, the linkers of the invention as shown in FIGS. 1D and 1E. In some embodiments where steric hindrance is not a constraint, the linker regions may be omitted.

Tagged PPC

PPCs of the present invention may also be modified in a way to form chimeric molecules (referred to herein as "tagged PPC") comprising a fusion of a PPC with a "epitope tag" which provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the flu HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et al., (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Elnhauer et al., J. Biochem. Biophys. Methods, 2001 Oct. 30, 49(1-3), 455-65; Song et al., Int. J. Oncol. 2003 Jan., 22(1)93-8; Werkmeister et al., Biochim. Biophys Acta 1993 May 7, 1157(1):50-4; Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein peptide tag (see, Lutz-Freyermuth et al. (1990) Proc. Natl. Acad. Sci. USA 87:6393.). It is understood that tagged PPC is a subset of all PPC and any reference to PPC in this disclosure also comprise tagged PPC.

In one embodiment of the invention, the three or four ABS of a PPC may be specific for an epitope of a tumor-associated antigen. Each ABS of a PPC may be specific for a different tumor-associated antigen. For example, one tumor-associated antigen may be CEA while another tumor associate antigen may be a non-CEA antigen. In another embodiment of the invention, the PPC has at least one ABS specific for an epitope of a hapten. The hapten may be, for example, histamine-succinyl-glycine (HSG).

In another embodiment of the invention, the PPC is linked, via a chemical bond, to a second molecule. These linkages may be made using a crosslinker. Alternatively, the linkage may be a binding pair such as antigen-antibody, hormone-receptor, drug-receptor, cell surface antigen-lectin, biotin-avidin, substrate/enzyme, peptide-receptor, and complementary nucleic acid strands, hapten-anti-hapten systems and the like. The avidin described includes reduced affinity avidin and reduced immunogenicity avidin as described by U.S. Pat. No. 5,698,405.

In one embodiment, the PPC may be linked to peptides (which includes proteins) to form a fusion PPC. The linkage may be any linkage that could be used to join two peptides since the PPC is itself comprised of peptides. For example, one method would be to synthesize the fusion PPC in a peptide synthesizer. In this case, the bond would be a peptide bond (also referred to as an amide bond). Another method would be to synthesize or clone a DNA to encode both polypeptides of the fusion PPC. The DNA is placed into an expression vector and transformed into a host cell permanently or transiently. Yet another method would be to use a chemical crosslinker to join two peptides.

The PPC molecule of the invention may further comprise a "detectable label" such as a "diagnostic agent." Detectable labels and diagnostic agents may include radiolabels, fluorescent labels, luminescent (chemiluminescent and bioluminescent) labels, positron-emission tomography (PET) labels and SPECT labels. The choice of labels are well known but specific examples are provided below. Methods of detecting labels are generally known and are also described in U.S. Pat. Nos. 4,595,654, 4,735,210, 4,792,521, 5,364,612, 5,439,665, 5,632,968, 5,697,902, 5,753,206, 6,071,490, 6,120,768, 6,126,916, and 6,187,284. The discussion of various labels in this segment of the disclosure is applicable to all references to labels in this invention.

Radiolabels may be further classified as therapeutic cations and diagnostic cations. Diagnostic cations may emit particles and/or positrons having 25-10,000 keV. Therapeutic cations may emit particles and/or positrons having 20 to 10,000 keV. Any conventional method of radiolabeling which is suitable for labeling proteins for in vivo use will be generally suitable for labeling the PPC of the invention. Such methods are known to the ordinary skilled artisan and are disclosed inter alia in, e.g., Childs et al., J. Nucl. Med., 26:293 (1985); and in U.S. Pat. Nos. 4,331,647, 4,348,376, 4,361,544, 4,468,457, 4,444,744, 4,624,846, 5,334,708, 5,670,132, 5,514,363, 5,976,492, 6,358,489, and 6,440,386. A wide range of labeling techniques are disclosed in Feteanu, "LABELED ANTIBODIES IN BIOLOGY AND MEDICINE", pages 214-309 (McGraw-Hill Int. Book Co., New York et al, 1978). The introduction of various metal radioiosotopes may be accomplished according to the procedures of Wagner et al., J. Nucl. Med., 20, 428 (1979); Sundberg et al, J. Med. Chem., 17, 1304 (1974); and Saha et al. J. Nucl. Med., 6, 542 (1976). Some of these methods describe the use of labeled antibodies. The methods may be used in the present invention by the substitution of PPC of the invention for the antibodies described in these methods.

The detectable label may be a fluorescent label, a chemiluminescent label, or a bioluminent label. Examples of fluorescent labels include fluorescein isothiocyanate, rhodamine, phycoerytherin, phycocyanin, allophycocyanin, o-phthaldehyde or fluorescamine. Examples of chemiluminescent labels include luminol, isoluminol, an aromatic acridinium ester, an imidazole, an acridinium salt and an oxalate ester. Examples of bioluminscent labels include luciferin, luciferase or aequorin.

The detectable labels may include one or more image enhancing agents. Image enhancing agents are useful for magnetic resonance imaging (MRI). Magnetic resonance imaging (MRI) agents are described, for example, in Pykett, Scientific American, 246, 78 (1982); Runge et al., Am. J. Radiol., 141, 1209 (1983). Examples of compounds useful for MRI image enhancement include complexes of paramagnetic ions, e.g., Gd(III), Eu(III), Dy(III), Pr(III), Pa(IV), Mn(II), Cr(III), Co(III), Fe(III), Cu(II), Ni(II), Ti(III), and V(IV) ions, or radicals, e.g., nitroxides, and these may be further attached to a substrate via a suitable linker. The MRI enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in, e.g., Pykett, Scientific American, 246:78 (1982); and Runge et al., Am. J. Radiol, 141:1209 (1987).

The detectable label may comprise one or more radiopaque or contrast agents for X-ray or computed tomography. Radiopaque or contrast agents may be barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, or thallous chloride. See U.S. Pat. Nos. 5,120,525, 5,128,119, 5,328,679.

The detectable label may comprise one or more ultrasound contrast agents such as, for example, a liposome (including gas filled liposome) or dextran.

In addition to the described detectable label, the PPC may comprise a therapeutic agent such as a radionuclide. Other applicable methods for labeling the PPC of this invention are disclosed in U.S. Pat. Nos. 5,061,641, 5,101,827.

Additional examples for using radiolabeled antibodies and engineered antibodies for detection or therapy may be found in U.S. Pat. Nos. 4,624,846, 5,482,698, 5,525,338, 5,609,846, 5,716,595, 5,728,369, 5,736,119, 5,746,996, 5,772,981, 5,776,093, 5,776,094, 5,776,095, 5,843,397, 5,851,527, 5,958,408, 5,965,131, 6,010,680, 6,077,499, 6,096,289, 6,331,175, 6,361,774, 6,387,350, 6,399,068, and 6,458,933. The PPC of the invention may be substituted for any of the antibodies mentioned in these patents.

The invention also provides for PPC where at least one ABS of the PPC is specific for an epitope on a cancer associated antigen and at least one ABS is specific for an epitope on a hapten.

Another embodiment of the invention is directed to a PPC linked to a conjugate (See U.S. Pat. No. 4,824,659 for a description of an antibody conjugate). The linkage may by a crosslinker. The conjugate may be a radionuclide or a cytotoxic agent, a drug, a chemotherapeutic agent, and a radionuclide.

In another embodiment of the invention, the PPC may have at least one ABS with specificity for an antigen on the surface of effector cells and at least one ABS specific for an antigen on a target cell or a virus. Examples of the first antigen may be an antigen of the surface of T-cells, natural killer cells, granulocytes, monocytes, or macrophages. In this case, the binding of the PPC to these two antigens may result in the killing or the mitotic arrest of the target cell. The following articles make reference to the utility of a polyvalent protein with these characteristics: Takemura et al., Cancer Immunol. Immunother. 2002 March; 51(1):33-44; Kipriyanov et al., J. Immunol. 2002 Jul. 1; 169(1):137-44; Stockmeyer et al., J. Immunol. 2000 Nov. 15; 165(10): 5954-61.

In another embodiment of the invention, the PPC may have at least one ABS with specificity for an antigen on the surface of a cells and at least one ABS specific for an antigenic substance. Examples of the first antigen may be an antigen of the surface of B-cells, monocytes, dendritic cells and macrophages. In this case, the binding of the PPC to the cell surface antigen and the antigenic substance results in the induction of an immune response to the antigenic substance.

In another embodiment, the invention is directed to a PPC wherein one of the polypeptides comprise an additional V-region. The V-region may be linked to the other V-regions by an additional linker. This additional V-region may comprise an amino acid sequence of a toxin, a hapten or a detectable moiety. Many examples of toxins, haptens, and detectable moiety are proteins and peptides with known amino acid sequences. Many of these peptides are cited as examples throughout this specification. These amino acid sequences may be used in the V-regions described in this paragraph.

Bispecific and Multispecific PPC

The invention provides for methods of using the PPC. In general, any method that require the use of an antibody or engineered antibody (see, e.g., Cao Y and Lam, L. Adv Drug Deliv Rev 2003 Feb. 10; 55(2): 171-97) may be performed using a PPC with a similar binding affinity and specificity. These methods includes any of the methods described in this disclosure and in the references, patents and patent applications cited therein. Descriptions of specific embodiments are described below.

Bispecific and multispecific PPC are effective for the recruitment of effector functions and treatment of tumor cells. Multispecificity refers to the ability of a engineered antibody, like the PPCs of the invention, to have multiple ABS where each ABS binds a different epitope. As discussed above, the fusion PPC of the invention may have at least 3 to 10 or more ABS and each ABS may have specificity to a different epitope. Further each different epitope may be on the same or different antigen. Bispecific antibodies have found particular use in recruiting the powerful effector functions of cytotoxic T cells or natural killer (NK) cells. Thus bispecific antibodies have been used to bridge the T cell coreceptor (CD3) (Staerz et al., Nature 314: 628-631, 1985) or FcRIII (CD16) (De Palazzo et al., Cell Immunol. 142: 338-347, 1992) and the cell surface antigen of a target cell to mediate the killing of target cells by cytotoxic T cells or NK cells. In mice, such anti-CD3 bisAbs can inhibit the growth of solid tumors (Titus et al., J. Immunol. 138: 4018-4022, 1987, Gamido et al., Cancer Res. 50: 42274232, 1990) or even eradicate lymphoma (Brissinck et al., J. Immunol. 147: 4019-4026, 1991); in humans, they have been used against malignant glioma (Brissinck et al., J. Immunol. 147: 4019-4026, 1991). Bispecific antibodies have also been used for ex vivo purging of leukaemia cells from bone marrow (T. Kaneko et al., Blood 81: 1333-1341, 1993). Bispecific antibodies synthesized in vitro have also been used to deliver enzymes, antigens, toxins, radionuclides and cytotoxic drugs to tumor cells (see Bonardi et al., Cancer Res. 53:187-199 1992). Any of the above method, and any of the methods in the cited references in this disclosure, may be performed using the bispecific PPCs of the invention as a substitute for the multispecific antibody (or functional derivatives) specified in these method.

The multispecific PPC of the invention may be used for imaging of tumors. Bispecific anti-tumor marker, anti-hapten antibodies have been used to image tumors (J. M. Le Doussal et al. Int. J. Cancer Supplement 7: 58-62, 1992; P. Peltier et al. J. Nucl. Med. 34: 1267-1273 1993; C. Somasundaram et al. Cancer Immunol. Immunother. 36: 337-345, 1993; A. Bruynck et al. Br. J. Cancer 67: 436-440, 1993). The method comprises two steps. In the first step, a bispecific antibody is injected and localize to the tumor by binding to a tumor-associated antigen. In the second step, a radioactively labeled hapten is then injected which preferentially localizes to the tumor, by binding to the bispecific antibody, enabling imaging of the tumor. Multispecific PPC of the invention with at least one ABS specific for tumor cells and one ABS specific for the hapten could be used to in place of the bispecific antibody to achieve the same results.

As another example, the PPC of the invention may be used to deliver cytotoxic drugs to tumor cells, using one binding site to deliver the drug and the other to bind to the tumor, or using systems analogous to that described for the delivery of doxorubicin to tumors by P. A. Trail et al. (Science 261: 212-215, 1993). These authors used an antibody directed to the Lewis Y antigen, covalently linked to doxorubicin, which was internalized into lysosomes and endosomes. The linkage was cleavable in these environments leading to delivery of the drug to these cells. Bivalent PPCs may be particularly useful to increase the avidity of the antibody for the tumor cell. The specificity may be increased by using a bispecific antibody directed against two (or more) different tumor-associated antigen on the same tumor or two (or more) epitopes on the same tumor-associated antigen.

The multispecific PPCs of the invention may be used to deliver therapeutic agents across the blood brain barrier. In this method, a multispecific PPC with one ABS directed against either FHA, an adhesin of the bacterium *Bordetella pertussis* or against the natural ligand for the leucocyte adhesion molecule CR3 (E. I Tuomanen et al. Proc. Natl. Acad. Sci. USA 90: 7824-7828, 1993) and the other ABS may then be directed against a target to provide the therapeutic function.

Multivalent PPCs may be particularly useful for imaging purposes for instance when localizing tumors by binding to two different epitopes of a tumor-associated antigen with a radiolabeled PPC. The presence of two ABS for one tumor-associated antigen would give an avidity component which may increase the signal to noise ratio of the detection method.

The multispecific PPCs of the invention may be used in retargetting of antibodies to a site or antigen for which they have no specificity under normal circumstances. The PPC would possess two ABSs; one ABS is specific for a target site, the other ABS is capable of binding to selected parts of an antibody molecule. In this manner, antibodies with no specificity for the antigen target are brought into proximity with the antigen via the PPC. This principle is advantageous for re-targeting antibodies in the circulation to sites within the body such as tumors and to block inappropriate immune responses exemplified by autoimmune disease and would allow recruitment of effector functions.

In this way, multispecific PPCs could be used to recruit effector functions through binding to whole antibody chains. One ABS of the PPC would be directed against antigen for therapy and the second arm against whole antibodies for the recruitment of effector functions.

In a preferred embodiment of the invention, the ABS in a PPC may be specific for an epitope of a tumor-associated antigen. The tumor-associated antigen may be associated with, for example, carcinomas, melanomas, sarcomas, gliomas, leukemias or lymphomas. A tumor-associated antigen may have more than one epitope. For example, a tumor-associated antigen may have at least 1, 2, 3, 4 epitopes. Other target antigens present in more than once cell type and useful in this invention are CD74, HLA-DR, Where the construct contain more than one ABS, the ABS may be specific for epitopes on the same tumor antigen or different tumor antigens. Thus, a PPC with 3 or 4 ABSs may bind from 1 to 3 or 4 of tumor antigens.

In a preferred embodiment, the ABS of a PPC has the same binding specificity as monoclonal antibody (Mab) Mu-9 and MAb 679. This can be achieved, for example, by using the sequence of the monoclonal antibodies to construct the $V_H$ and $V_L$ regions of the PPC.

In addition, the PPC of the invention may comprise one or more ABS which bind an epitope on a hapten. The hapten may be a histamine-succinyl-glycine (HSG) or indium-DTPA. Naturally, the ABS of the PPC may bind multiple epitopes of one hapten or different epitopes of different haptens. The three or more ABS of a PPC can bind any combination of tumor-associated antigens or haptens without limitation. As an example, one ABS may bind CEA while another ABS may bind a non-CEA tumor-associated antigen. For example, where the number of ABS is equal to N, the number of ABS that binds tumor-associated antigen may range from zero to N. The remainder of the ABS may all bind hapten.

As the above examples illustrate, the multispecific PPC of the invention may serve as a substitute for multi specific engineered antibodies in any method. These methods includes any of the methods described in this disclosure and in the references, patents and patent applications cited therein. More specific examples of the use of PPC are discussed below.

Methods for Treating, Diagnosing, and Detecting Disorders

The invention also provides for methods for treating, diagnosing, and detecting a symptom of a neoplastic disorder by administering any of the PPC of this disclosure with an ABS directed to a cancer associated antigen. The PPC may be administered with one or more therapeutic agents, diagnostic agents, or detecting agents and one or more cytokines. The therapeutic agent may be a chemotherapeutic agent or a combination of chemotherapy agents. The administration of the therapeutic agent or cytokine may be before, during or after the administration of the PPC.

When more than one therapeutic agents are used, the therapeutic agents may be the same or different, and may be, for example, therapeutic radionuclides, drugs, hormones, hormone antagonists, receptor antagonists, enzymes or proenzymes activated by another agent, autocrines or cytokines. Toxins also can be used in the methods of the present invention. Other therapeutic agents useful in the present invention include anti-DNA, anti-RNA, radiolabeled oligonucleotides, such as anti-sense oligonucleotides, anti-protein and anti-chromatin cytotoxic or antimicrobial agents. Other therapeutic agents are known to those skilled in the art, and the use of such other therapeutic agents in accordance with the present invention is specifically contemplated.

In a preferred embodiment, the therapeutic agents comprise different isotopes, which are effective over different distances as a result of their individual energy emissions, are used as first and second therapeutic agents. This process achieves more effective treatment of tumors, and is useful in patients presenting with multiple tumors of differing sizes, as in normal clinical circumstances.

Few of the available isotopes are useful for treating the very smallest tumor deposits and single cells, and a drug or toxin may be a more useful therapeutic agent in these situations. Accordingly, in preferred embodiments of the present invention, isotopes are used in combination with non-isotopic species such as drugs, toxins, and neutron capture agents. Many drugs and toxins are known which have cytotoxic effects on cells, and can be used in connection with the present invention. They are to be found in compendia of drugs and toxins, such as the Merck Index, Goodman and Gilman, and the like, and in the references cited above.

Drugs that interfere with intracellular protein synthesis can also be used in the methods of the present invention; such drugs are known to those skilled in the art and include puromycin, cycloheximide, and ribonuclease.

The therapeutic agents may be linked to the PPC. Methods of making linked proteins in which one recombinant protein comprises a cytotoxic agent, therapeutic agent or chemotherapeutic agent also are known to those of skill in the art. These methods can be applied to the PPC of the invention. For example, antibody-*Pseudomonas* exotoxin A PPCs have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin PPCs containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1: 177 (1995), have described an antibody-toxin PPC having an RNase moiety, while Linardou et al., Cell Biophys. 24-25: 243 (1994), produced an antibody-toxin PPC comprising a DNase I component. As a further example, Dohlsten et al., Proc. Nat'l Acad. Sci. USA 91:8945 (1994), reported an antibody-toxin PPC comprising Staphylococcal enterotoxin-A. These methods are also applicable for making the PPCs comprising a toxin of the invention. Other suitable cytotoxic agents are listed in the definitions section of this disclosure.

It is to be understood that any combination of the above described therapeutic agents may be used. For example, a PPC may be conjugated to two or more radioisotopes, or drugs. When a mixture of therapeutic agents is used, a plurality of therapeutic agents are delivered to the tumor sites, thereby enhancing the benefits of the method. The use of mixtures of nuclides has the further advantage that a greater percentage of the injected biotinylated chelates delivers a toxic payload to the tumor target.

The present invention also contemplates dyes used, for example, in photodynamic therapy, and used in conjunction with appropriate non-ionizing radiation. The use of light and porphyrins in methods of the present invention is also contemplated and their use in cancer therapy has been reviewed (van den Bergh, Chemistry in Britain, 22: 430-437 (1986)).

The invention also provides for methods of reducing a symptom of a neoplastic disorder in a subject. The subject can be any animal including horses, mice, rats, pigs, bovines, chickens etc. In a preferred embodiment, the animal is a human. In the method, a PPC is administered to a patient displaying a symptom of the neoplastic disorder to reduce the symptom. The neoplastic disorder may be a carcinomas, sarcomas, gliomas, lymhomas, leukemias, melanomas or the like. In a preferred embodiment, the neoplastic disorder is a B-cell malignancy such as indolent forms of B-cell lymphomas, aggressive forms of B-cell lymphomas (including non-Hodgkin's lymphoma), chronic lymphatic leukemias, or acute lymphatic leukemias.

Another embodiment of the invention is directed to a method for treating B cell malignancies. The method involves administering to a subject having a B cell malignancy one or more dosages of a therapeutic composition which contains a pharmaceutically acceptable carrier and at least one PPC of the invention. The B-cell malignancies may be any B-cell malignancy including, at least, carcinomas, sarcomas, gliomas, lymphomas, leukemias, and melanomas. In the method, the PPC may be parenterally administered in a dosage of 20 to 1500 milligrams protein per dose. In a preferred embodiment, the PPC may be administered in a dosage of 20 to 500 milligrams protein per dose. In a most preferred embodiment, the PPC may be parenterally administered in a dosage of 20 to 100 milligrams protein per dose. Any of these dosages may be repeatedly administered to achieve an even higher dosage. As discussed above, the PPC of the invention, including the PPC in the methods of the invention, may be radiolabeled. In administering a PPC that is radiolabeled, the dosage of the radiolabel may be between 15 to 40 mCi. In a preferred embodiment, the dosage is between 10 and 30 mCi. In a more preferred embodiment, the dosage may be between 20 and 30 mCi. In another more preferred embodiment, the dosage may be between 10 and 20 mCi.

In another embodiment, where a method of the calls for the administration of PPC, the PPC may be administered before, after or concurrently with a chemotherapeutic agent, cytokine, or colony stimulating factor. Specific examples of chemotherapeutic agents and cytokines are enumerated in another section of the specification.

Any of the methods of the invention, including methods for treating autoimmune disorders and neoplastic disorders may be used to treat disorders such as cardiovascular diseases and inflammation. These disorders include clots, emboli, myocardial infarction, ischemic heart disease, and atherosclerotic plaques. PPCs that are suitable for treating these disorders include those PPCs with an ABS specific for CD74 (e.g., hLL1), NCA (or -CD66) and NCA90. This would include ABS with the same specificity as hMN3. The diagnostic imaging methods of the invention are particularly adaptable for using the above stated PPC. In particular, the detection methods, diagnostic methods, and the cell ablation methods may be applied to cardiovascular disorders. For example, the detection may be used to detect damaged heart and vascular tissue. The cell ablation methods may be used for targeting diseased heart tissue. Inflammation can be detected or treated with anti-granulocyte (e.g., anti-CD66, anti-CD33, anti-CD45), anti-lymphocyte (anti-B- or anti-T-cell antibodies), and/or anti-monocyte antibodies (e.g., anti-Ia or anti-CD74 antibody).

In another embodiment of the invention, the treatment methods of the invention can be used in combination with other compounds or techniques for preventing, mitigating or reversing the side effects of cytotoxic agents. Examples of such combinations include, e.g., administration of IL-1 together with a second antibody for rapid clearance, as described. e.g., U.S. Pat. No. 4,624,846, from 3 to 72 hours after administration of a targeted primary PPC antibody fragment conjugate (with a radioisotope, drug or toxin as the cytotoxic component of the immunoconjugate) or of a non-conjugated drug or toxin, to enhance clearance of the conjugate, drug or toxin from the circulation and to mitigate or reverse myeloid and other hematopoietic toxicity caused by the therapeutic agent. This method is also applicable to the PPC of the invention.

In another aspect, cancer therapy often involves a combination of more than one tumoricidal agent, e.g., a drug and a radioisotope, or a radioisotope and a Boron-10 agent for neutron-activated therapy, or a drug and a biological response modifier, or a PPC conjugate and a biological response modifier. The cytokine can be integrated into such a therapeutic regimen to maximize the efficacy of each component thereof.

Similarly, certain antileukemic and antilymphoma antibodies conjugated with radioisotopes that are $\beta$ or $\alpha$ emitters can induce myeloid and other hematopoietic side effects when these agents are not solely directed to the tumor cells, particularly when the tumor cells are in the circulation and in the blood-forming organs. Concomitant and/or subsequent administration of the hematopoietic cytokine (growth factor, such as colony stimulating factors (e.g., G-CSF and GM-CSF) is preferred to reduce or ameliorate the hematopoietic side effects, while augmenting the anticancer effects.

In addition to preventing, mitigating or reversing the myelosuppressive or other hematopoietic side effects of the therapy, cytokines such as, e.g., IL-1, can have anticancer effects (Nakamura et al., Gann 77:1734-1739, 1986; Nakata et al., Cancer Res. 48:584-588, 1988), as well as IL-12, and therefore are capable of enhancing the therapeutic effect of the targeted agents when used in combination with these other therapeutic modalities. Thus, another aspect of the present invention is to maximize the antiproliferative activity of the cytokine by conjugating it to the targeting PPC to form a heteroconjugate. Since the cytokines are polypeptides, conjugation to the PPC can be performed using any of the conventional methods for linking polypeptides to antibodies. These include, e.g., use of the heterobifunctional reagent N-succinimidyl 3-(2-pyridyldithio)propionate (SPDP), according to published procedures, e.g., that of Carlsson et al., Biochem. J. 173:723-737, 1978, use of glutaraldehyde, carbodiimide or like condensing and/or linking reagents.

It is preferable to achieve a high ratio of the cytokine to the PPC without affecting the latter's immunoreactivity and targeting properties. Thus, it may be advantageous to use a carrier for the cytokine and to link a plurality of cytokine molecules to the carrier, which is then linked to the PPC. A particularly effective method for achieving this result is to use the method of Shih et al., PCT/US WO 87/005031, wherein an addend is conjugated to a polymer such as an aminodextran, which is then site-specifically linked to the oxidized carbohydrate portion of a PPC. Depending upon the cytokine and PPC used, 20 to more than 100 cytokine molecules per PPC can be attached without affecting the PPC appreciably, and in some circumstances 100 to 1,000 molecules of cytokine per PPC molecule can be achieved.

Use of IL-1 or G-CSF as the cytokine is preferable if a cytokine with antitumor activity is desired to potentiate the targeting PPC's effects, especially if the latter is conjugated with a toxic radioisotope or drug. If the targeting PPC circulates and deposits in other normal organs, such as the bone marrow, then the presence of the cytokine is important to prevent, mitigate or reverse the hematologic side effects that would normally result. Since some of the cytokines have lymphoid effector cell functions for tumor cell killing (e.g., IL-2), the heteroconjugate of this invention provides a multimodal therapy to the target, whether it be a cancer, an infection, or another lesion that is unresponsive to more traditional measures.

An appropriate dose of the cytokine can be administered prior to, simultaneously with or subsequent to the administration of the therapeutic agent. The object will be to maximize the cytotoxic activity of the agent on the pathological lesion, such as cancer cells or infectious organisms, while minimizing toxicity to the myeloid and other hematopoietic cells. Careful monitoring of the WBC and other blood elements, including but not limited to erythrocyte (red blood cell/RBC) count, thrombocyte (platelet) count, and including a differential WBC analysis to monitor the myloid/lymphoid series, as well as the bone marrow hematological picture during the course of therapy, with particular attention to possible depletion of myeloid lymphoid forms, but also the status of immature erythrocytes, myelocytes, lymphocytes and thrombocytes, will permit optimization of the cytokine treatment. Depending upon which hematologic element is adversely affected, the choice of cytokine and administration schedule can be individualized in each circumstance, including the combination of cytokines, such as IL-1 and IL-3; IL-1 and IL-2; IL-1 and GM-CSF; IL-1, erythropoietin, and platelet growth factor and the like.

Correlation of the choice of cytokine, singly or in combinations, and doses thereof, to hematotoxicity is important, since each cytokine generally has its effect mostly on particular hematopoietic elements. The following guidelines may be used for choosing cytokines in the methods of the invention. For example, if a cytotoxic agent has both severe myeloid and thrombocytic toxicity, the combination of IL-1 and IL-3 in a 1:1 or 2:1 (or higher) ratio will be advantageous. Thus, reduction in the WBC count to a level below about 2,000 and platelets to a level below about 20,000 can be reversed by administration of from about 1 ug to about 500 ug, preferably 5-100 ug, more preferably about 10 ug of rIL-1 in a single dose, together with or followed by administration of from about 1 ug to about 200 ug, preferably 5-50 ug, more preferably about 5 ug of IL-3. The applications can be repeated, with the reversal of the myeloid and platelet depressions occurring within about 5-20 days, usually about 7 days. The ordinary skilled clinician will appreciate that variations in the timing and dosage of cytokine administration and cytokine combinations and dosages are a function of the cytokine used, the nature of the bone marrow and/or other hematopoietic element depressed, and the nature of the patient (e.g., prior toxicity affecting bone marrow status) and the cytotoxic agent and protocol.

Examples of autoimmune diseases that could be treated by the methods of the invention include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pemiciousanemia, rapidly progressive glomerulonephritis, psoriasis, and fibrosing alveolitis.

The method of treating autoimmune disease may comprise an additional step of administering a secondary antibody or PPC with an ABS specific for an epitope on T-cells, plasma cells, or macrophages or inflammatory cytokines. This additional step may be performed before, during or after the administration the PPC.

Another major application of the methods and PPCs of the invention is to depress host immunity in certain autoimmune diseases such as, for example, systemic lupus erythematosis, and in patients receiving organ transplants. In these applications, the PPC is associated with cytotoxic drugs. These cytotoxic drugs are similar to those often used in cancer chemotherapy, with the attendant myeloid and other hematopoietic side effects. In addition to these drugs, specific PPCs targeted against these lymphoid cells (particularly T-cell), (e.g., a PPC with an ABS derived from the anti-Tac monoclonal antibody of Uchiyama et al., J. Immunol. 126:1393 and 1398 (1981), which specifically binds to the human IL-2 receptor of activated T-cells) can be conjugated to cytotoxic agents, such as drugs, toxins or radioisotopes, to effect a relatively select killing of these cells involved in organ rejection. For example, a T-cell specific PPC can be conjugated with α, β or γ emitting radioisotope, and this can be administered to the patient prior to undertaking organ transplantation and, if needed, also thereafter.

In order to effect a high T-cell killing dose without the concomitant limiting side effects to the hematopoietic system, this treatment can be combined with the use of cytokines, according to the present invention. This method is preferred for the long-term survival of many organ transplants, such as the kidney, heart, liver, etc., where a critical period of organ rejection needs to be overcome.

The dosage level of the cytokine will be a function of the extent of compromise of the hematopoietic cells, correlated generally with the white blood cell (WBC) level in the patient. Periodic monitoring of the WBC and other blood cell counts and adjustment of the rate and frequency of infusion or the dosage of the cytokine administered to achieve a relatively constant level of WBC's will ensure that the patient does not sustain undue marrow toxicity from the therapy. Experience will permit anticipation of WBC lowering and in fusion of the cytokine at a time and in an amount sufficient to substantially prevent WBC-depression. Importantly, this also insures that excessive side effects due to the cytokine itself are not produced, but only such side effects as are necessary to prevent compromise of the patient's myeloid and other hematopoietic cell systems.

Correlation of cytokine dosage to WBC count suggests that, in general, reduction of WBC count from a normal range of 8-12,000/mm$^3$ to a level of about 2,000 can be reversed by administration of from about 1 ug to about 500 ug, preferably 5-100 ug, more preferably about 10 ug of recombinant human IL-1 in a single dose, the reversal of WBC count depression occurring within about 2-12 days, usually about 4 days. The clinician will appreciate that variations in the timing and dosage of cytokine administration as a function of the type of cytokine used, the extent and rate of compromise of the bone marrow and/or other components of the myeloid and/or other hematopoietic elements and the individual characteristics of the patient and the therapy protocol will be possible and often desirable. These can easily be made by the clinician using conventional monitoring techniques and dosimetric principles.

The methods of the invention, including methods for treating autoimmune disorders and neoplastic disorders may be used to treat disorders such as cardiovascular diseases and inflammation. These disorders include myocardial infarction, ischemic heart disease, and atherosclerotic plaques. PPCs that are suitable for treating these disorders include those PPCs with an ABS specific for CD74 (e.g., hLL1), NCA (or -CD66) and NCA90. This would include ABS with the same specificity as hMN3. The diagnostic imaging methods of the invention are particularly adaptable for using the above stated PPCs. In particular, the detection methods, diagnostic methods, and the cell ablation methods may be applied to cardiovascular disorders. For example, the detection may be used to detect damaged heart and vascular tissue. The cell ablation methods may be used for targeting diseased heart tissue. Inflammation can be detected or treated with anti-granulocyte (e.g., anti-CD66, anti-CD33, anti-CD45), anti-lymphocyte (anti-B- or anti-T-cell antibodies), and/or anti-monocyte antibodies (e.g., anti-Ia or anti-CD74 antibody).

Any of the methods of the invention, including methods for treating autoimmune disorders and neoplastic disorders may be used to treat disorders such as neurological diseases such as Alzheimer's disease. PPC that are suitable for treating these disorders include those PPC with an ABS specific for the amyloid plaques of Alzheimer patients. The diagnostic imaging methods of the invention are particularly adaptable for using the above stated PPC. In particular, the detection methods, diagnostic methods, and the cell ablation methods may be applied to neurological disorders. For example, the detection may be used to detect damaged brain tissue or brain tissue with amyloid. The cell ablation methods may be used for targeting amyloid. Inflammation can be detected or treated with anti-amyloid PPCs.

This invention also provides for methods of detecting and diagnosing a diseased tissue or a disease. For example, any of the methods of treatment presented may be performed with a PPC that has a detectable label, such as, for example, a radiolabel. The PPC can be detected after administration to the patient. Thus, any of the treatment methods can be used as detecting methods by the additional step of detecting the PPC after administration to the patient. Furthermore, by using a PPC with a specificity to a known pathogen, diseased cell, tumor associated antigen, disease associated antigen (e.g., amyloid) and the like, the presence of a disease may be diagnosed.

Methods of Administration

The preferred route for administration of the invention is parental injection. In parenteral administration, the compositions of this invention will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, such as oral administration are also contemplated.

The PPC of the present invention may be administered in solution. The pH of the solution should be in the range of pH 5 to 9.5, preferably pH 6.5 to 7.5. The PPC thereof should be in a solution having a suitable pharmaceutically acceptable buffer such as phosphate, tris(hydroxymethyl) aminomethane-HCl or citrate and the like. Buffer concentrations should be in the range of 1 to 100 mM. The solution of the immunoglobulin may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included and may be added to a solution containing the PPC or to the composition from which the solution is prepared. Systemic administration of the PPC is typically made every two to three days or once a week if a humanized form of the antibody is used as a template for the PPC. Alternatively, daily administration is useful. Usually administration is by either intramuscular injection or intravascular infusion.

Administration may also be intranasal or by other non-parenteral routes. The PPC may also be administered via microspheres, liposomes or other microparticulate delivery systems placed in certain tissues including blood.

The PPC may be administered by aerosol to achieve localized delivery to the lungs. This is accomplished by preparing an aqueous aerosol, liposomal preparation or solid particles containing or derivatives thereof. A nonaqueous (e.g., fluorocarbon propellent) suspension could be used. Sonic nebulizers preferably are used in preparing aerosols. Sonic nebulizers minimize exposing the PPC to shear, which can result in degradation of the PPC.

In general, the dosage of administered PPC will vary depending upon such factors as the patient's age, weight, height, sex, general medical condition and previous medical history. Preferably, a saturating dose of PPC is administered to a patient.

Typically, it is desirable to provide the recipient with a dosage that is in the range of from about 50 to 500 milligrams of PPC, although a lower or higher dosage also may be administered as circumstances dictate. Examples of dosages include 20 to 1500 milligrams protein per dose, 20 to 500 milligrams protein per dose, 20 to 100 milligrams protein per dose, 20 to 100 milligrams protein per dose, 20 to 1500 milligrams protein per dose. In the embodiments where the PPC of PPC comprise a radio nuclide, the dosage may be measured by millicurries. In that case, the dosage may be between 15 and 40 mCi, 10 and 30 mCi, 20 and 30 mCi, or 10 and 20 mCi.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (Mack Publishing Co. 1995), and Goodman and Gilman's THE PHARMACOLOGICAL BASIS OF THERAPEUTICS (Goodman et al., Eds. Macmillan Publishing Co., New York, 1980 and 2001 editions).

For purposes of therapy, one or more PPCs and a pharmaceutically acceptable carrier are administered to a patient in a therapeutically effective amount. A combination of one or more PPCs and a pharmaceutically acceptable carrier is said to be administered in a "therapeutically effective amount" if the amount administered is physiologically significant. An agent is physiologically significant if its presence results in a detectable change in the physiology of a recipient patient. In the present context, an agent is physiologically significant if its presence results in the inhibition of the growth of target cells.

PPC linked to radionuclide are particularly effective for microbial therapy. After it has been determined that PPC are localized at infectious sites in a subject, higher doses of the labeled PPC, generally from 20 mCi to 150 mCi per dose for I-131, 5 mCi to 30 mCi per dose for Y-90, or 5 mCi to 20 mCi Re-186, each based on a 70 kg patient weight, are injected. Injection may be intravenous, intraarterial, intralymphatic, intrathecal, or intracavitary (i.e., parenterally), and may be repeated. It may be advantageous for some therapies to administer multiple, divided doses of PPC or PPC composite, thus providing higher microbial toxic doses without usually effecting a proportional increase in radiation of normal tissues.

A variety of radionuclides are useful for therapy, and they may be incorporated into the specific PPC by the labeling techniques discussed above, as well as other conventional techniques well known to the art. Preferred therapeutically effective radionuclides are actinium-225, astatine-211, bismuth-212, yttrium-90, rhenium-186, rhenium-188, copper-67, phosphorus-32, lutetium-177, iodine-131, and iodine-125, although other radionuclides as well as photosensitizing agents are also suitable.

As discussed above, the PPC may be labeled and the use of a labeled PPC in the methods of the invention is also contemplated. The dosage of the radiolabel may be in the range of between 10 and 60 mCi per dose for yttrium-90. Preferably, between 10 and 50 mCi per dose. Most preferably, between 15 and 40 mCi, or between 20 to 30 mCi per dose or between 10 to 30 mCi per dose of yttrium-90.

In a preferred embodiment of the invention, the PPC to be administered to a patient suffering from a neoplastic disorder is an PPC comprising at least one ABS specific for an epitope from the appropriate tumor-associated antigen. That is, the PPC can bind one of these tumor-associated antigens at more than one site (epitope). Bispecific and polyspecific immunoglobulin derivative have may uses which are enumerated in WO02082041 A2.

In practicing the methods of the invention the PPC may further comprise any of the additional components described above which includes, at least, toxins, radionuclide, chemotherapeutic agents or antimicrobial agents. In some embodiments of the invention, a chemotherapeutic agent may be physically linked to the PPC. In other embodiments, the chemotherapeutic agent may be unlinked. Unlinked chemotherapeutic agents may be administered before, during, or after the administration of the PPC.

In another embodiment of the invention, the PPC may be administered before, during, or after administration of a cytokine moiety. Other agents that can be advantageously administered before, during of after the administration of PPC, for any of the methods of the invention, include at least, granulocyte-colony stimulating factor (G-CSF), granulocyte macrophage-colony stimulating factor (GM-CSF), erythropoietin, thrombopoietin, and the like. Other useful agents include a hematopoietic growth factors conjugated to a bispecific antibody.

The PPC of the invention may be substituted for immunoglobulin used for cancer therapy. It is well known that radioisotopes, drugs, and toxins can be conjugated to antibodies or antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986), in Immunoconjugates. Antibody Conjugates in Radioimaging and Therapy of Cancer (C. W. Vogel, ed., 3-300, Oxford University Press, N.Y., 1987), in Dillman, R. O. (CRC Critical Reviews in Oncology/Hematology 1:357, CRC Press, Inc., 1984), in Pastan et al. (Cell 47:641, 1986). in Vitetta et al. (Science 238:1098-1104, 1987) and in Brady et al. (Int. J. Rad. Oncol. Biol. Phys. 13:1535-1544, 1987). Other examples of the use of immunoconjugates for cancer and other forms of therapy have been disclosed, inter alia, in U.S. Pat. Nos. 4,331,647, 4,348,376, 4,361,544, 4,468,457, 4,444, 744, 4,460,459, 4,460,561 4,624,846, 4,818,709, 4,046,722, 4,671,958, 4,046,784, 5,332,567, 5,443,953, 5,541,297, 5,601,825, 5,635,603, 5,637,288, 5,677,427, 5,686,578, 5,698,178, 5,789,554, 5,922,302, 6,187,287, and 6,319,500. These methods are also applicable to the methods of the invention by the substitution of the immunoconjugated engineered antibodies and antibodies of the previous methods with the PPC of this invention.

The PPC of the invention, for use in any of the methods of the invention, may be associated or administered with antimicrobial agents.

The PPC of the invention, for use in any of the methods of the invention, may be associated or administered with cytokines and immune modulators (defined elsewhere in this disclosure). These cytokines and immune modulators, includes, at least, interferonss alpha, beta and gamma, and colony stimulating factors.

The invention also provides for methods for stimulating the immune response in a patient using the PPC of the invention. In one embodiment, the PPC of the invention may comprise an ABS of an anti-idiotype antibody. The PPC may mimic an epitope of a tumor-associated antigen to enhance the body's immune response.

The PPC of the invention may be used for many immunological procedures currently employing antibodies. These procedures include the use of anti-idiotypic antibodies and epitope conjugated antibodies to boost the immune system. See, U.S. Pat. Nos. 5,798,100 6,090,381, 6,132,718. Anti-idiotypic antibodies are also employed as vaccines against cancers and infectious diseases U.S. Pat. Nos. 6,440,416 and 6,472,511. Further polyspecific PPC may bind multidrug transporter proteins and overcome multidrug resistant phenotype in cells and pathogens. The antibodies in these methods may be replaced by the PPC of this invention.

The invention also provides for a method for treating a symptom of an autoimmune disorder. In the method, an PPC of the invention is administered to a patient with an autoimmune disorder. The PPC may be admixed with a pharmaceutically acceptable carrier before administration. The PPC of this method should contain at least one ABS with binding specificity to a B-cell antigen epitope. The B cell antigen may be CD22 and the epitope may be epitope A, epitope B, epitope C, epitope D and epitope E of CD22. The B cell-associated antigen may also be another cell antigen such as CD19, CD20, HLA-DR and CD74.

The ABS may contain a sequence of subhuman primate, murine monoclonal antibody, chimeric antibody, humanized antibody, or human origin. For example, the ABS may be of humanized LL2 (anti-CD22) or A20 (anti-CD20) monoclonal antibody origin.

The administration may be parenteral with dosages from 20 to 2000 mg per dose. Administration may be repeated until a degree of reduction in symptom is achieved.

The patients who may be treated by the methods of the invention include any animal including humans. Preferably, the animal is a mammal such as humans, primates, equines, canines and felines.

The method and PPCs of the invention may be used for the treatment of diseases that are resistant or refractory towards systemic chemotherapy. These include various viral, fungal, bacterial and protozoan infections, as well as particular parasitic infections. Other viral infections include those caused by influenza virus, herpes virus, e.g., Epstein-Barr virus and cytomegalovirus, rabies virus (Rhabdoviridae) and papovavirus, all of which are difficult to treat with systemic antibiotic/cytotoxic agents. Use of PPC conjugates, provides a significantly higher therapeutic index for antiviral drugs and toxins, thus enhancing their efficacy and reducing systemic side effects. Targeted radioimmunotherapy with conjugates of PPC with therapeutic radioisotopes (including boron addends activatable with thermal neutrons) offers a new approach to antiviral therapy Protozoans that may be treated by the methods and PPCs include, e.g., Plasmodia (especially *P. falciparum*, the malaria parasite), *Toxoplasma gondii* (the toxoplasmosis infectious agent), Leishmaniae (infectious agent in leishmaniasis), and *Escherichia histolytica*. Detection and treatment of malaria in its various stages is significantly enhanced using the PPC of the invention. As noted above, MAbs that bind to sporozoite antigens are known. However, since sporozoite antigens are not shared by blood stage parasites, the use of MAbs against sporozoite antigens for targeting is limited to a relatively short period of time in which the sporozoites are free in the circulation, prior to and just after injection of and development in the host's hepatocytes. Thus, it is preferable to use a mixture of PPCs. Alternatively, a PPC with ABSs that target more than one parasite stage of a protozoan (such as *P. falciparum*) is also useful. The MAbs are conjugated to a suitable radionuclide for imaging (e.g., Tc-99m) or for therapy (e.g., astatine-211; rhenium-186), or with an antimalarial drug (e.g., pyrimethamine) for more selective therapy.

Toxoplasmosis is also resistant to systemic chemotherapy. It is not clear whether MAbs that bind specifically to *T. gondii*, or natural, host antibodies, can play a role in the immune response to toxoplasmosis but, as in the case of malarial parasites, appropriately targeted PPC are effective vehicles for the delivery of therapeutic agents.

Schistosomiasis, a widely prevalent helminth infection, is initiated by free-swimming cercariae that are carried by some freshwater snails. As in the case of malaria, there are different stages of cercariae involved in the infectious process. PPCs that bind to a plurality of stages of cercariae, optionally to a plurality of epitopes on one or more thereof, and preferably in the form of a polyspecific composite, can be conjugated to an imaging or therapy agent for effective targeting and enhanced therapeutic efficacy.

PPCs that bind to one or more forms of *Trypanosoma cruzi*, the causative agent of Chagas' disease, can be made and used for detection and treatment of this microbial infection. PPCs which reacts with a cell-surface glycoprotein, as well as PPCs reactive with other surface antigens on differentiation stages of the trypanosome, are suitable for directing imaging and therapeutic agents to sites of parasitic infiltration in the body.

Another very difficult infectious organism to treat by available drugs is the leprosy *bacillus* (*Mycobacterium leprae*). PPCs that specifically bind to a plurality of epitopes on the surface of *M. leprae* can be made and can be used, alone or in combination, to target imaging agents and/or antibiotic/cytotoxic agents to the *bacillus*.

Helminthic parasitic infections, e.g., Strongyloidosis and Trichinosis, themselves relatively refractory towards chemotherapeutic agents, are suitable candidates for PPC-targeted diagnosis and therapy according to the invention, using PPCs that bind specifically to one or, preferably, to a plurality of epitopes on the parasites.

Antibodies are available or can easily be raised that specifically bind to most of the microbes and parasites responsible for the majority of infections in humans. Many of these have been used previously for in vitro diagnostic purposes and the present invention shows their utility as components of antibody conjugates to target diagnostic and therapeutic agents to sites of infection. Microbial pathogens and invertebrate parasites of humans and mammals are organisms with complex life cycles having a diversity of antigens expressed at various stages thereof. Therefore, targeted treatment can best be effected when PPC conjugates which recognize antigen determinants on the different forms are made and used in combination, either as mixtures or as polyspecific conjugates, linked to the appropriate therapeutic modality. The production of PPC is not difficult because the antibody may be purified and its sequence determined. The same principle applies to using the reagents comprising PPCs for detecting sites of infection by attachment of imaging agents, e.g., radionuclides and/or MRI enhancing agents.

The invention also provides a method of intraoperatively identifying diseased tissues by administering an effective amount of a PPC; and a targetable construct where the PPC comprises at least one antigen binding site that specifically binds a targeted tissue and at least one other antigen binding site that specifically binds the targetable construct; and wherein said at least one antigen binding site is capable of binding to a complementary binding moiety on the target cells, tissues or pathogen or on a molecule produced by or associated therewith.

The invention also provides a method for the endoscopic identification of diseased tissues, in a subject, by administering an effective amount of a PPC and administering a targetable construct. The PPC comprises at least one antigen binding site that specifically binds a targeted tissue and at least one antigen binding site that specifically binds the targetable construct; and wherein said at least one antigen binding site shows specific binding to a complementary binding moiety on the target cells, tissues or pathogen or on a molecule produced by or associated therewith.

An alternative method of detection suitable for use in the present invention is wireless capsule endoscopy, using an ingested capsule camera/detector of the type that is commercially available from, for example, Given Imaging (Norcross Ga.).

The invention also provides a method for the endoscopic identification of diseased tissues, in a subject, by administering an effective amount of a PPC; and administering a targetable construct. In this embodiment, the PPC comprises at least one antigen binding site that specifically binds a targeted tissue and at least one antigen binding site that specifically binds the targetable construct; and wherein said at least one antigen binding site shows specific binding to a complementary binding moiety on the target cells, tissues or pathogen or on a molecule produced by or associated therewith.

The invention also provides a method for the intravascular identification of diseased tissues, in a subject by administering an effective amount of a PPC and a targetable construct. The PPC comprise at least one antigen binding site that specifically binds a targeted tissue and at least one antigen binding site that specifically binds a targetable construct. The at least one antigen binding site is capable of binding to a complementary binding moiety on the target cells, tissues or pathogen or on a molecule produced by or associated with the cell, tissues or pathogen. The target tissue may be a tissue from normal thyroid, liver, heart, ovary, thymus, parathyroid, endometrium, bone marrow, or spleen.

The invention also provides for a kit for practicing the methods of the invention. The kit may include a targetable construct. The targetable construct may be labeled by any of the labels described as suitable for targetable constructs above. Further, the targetable construct may be unlabeled but the kit may comprise labeling reagents to label the targetable construct. The labeling reagents, if included, may contain the label and a crosslinker. The kit may also contain an PPC of the invention comprising at least one ABS specific for the targetable construct and at least one ABS specific for a targetable tissue. The kit may optionally contain a clearing composition for clearing non-localized PPC.

Nucleic Acid Encoding PPC

Another embodiment of the invention is directed to a nucleic acid molecule with at least one open reading frame (ORF) that encodes at least one polypeptide of any of the PPC of the invention. The open reading frame of the nucleic acids of the invention may be linked, in an operational manner, to one or more nucleic acid elements that promote the expression of the open reading frame. These elements are known to those of skill in the art and include, at least, promoters, enhancers, proximal stimulatory elements and the like. In a preferred embodiment, a nucleic acid molecule may comprise two open reading frame that together express both chains of a PPC (see, e.g., FIG. 1A).

The nucleic acids of the invention may be present in many forms such as, for example, an expression cassette or an episome (plasmids, cosmids, and the like). Thus, an expression cassette or an episome, such as a plasmid or cosmid) is also envisioned as an embodiment of the invention. Another embodiment of the invention is directed to a host cell comprising a nucleic acid of the invention. The host cell may be an *E. coli*, a yeast, a plant cell or a mammalian cell. Mammalian cells may be, for example, a human cell or a mouse cell.

The nucleic acids of the invention may be expressed. Where the nucleic acid is an RNA, the expression may involve a first step of reverse transcribing the RNA into DNA. The DNA sequence may then be operably linked to regulatory sequences controlling transcriptional expression in an expression vector and then, introduced into either a prokaryotic or eukaryotic host cell. In addition to transcriptional regulatory sequences, such as promoters and enhancers, expression vectors include translational regulatory sequences and a marker gene which is suitable for selection of cells that carry the expression vector.

Suitable promoters for expression in a prokaryotic host can be repressible, constitutive, or inducible. Suitable promoters are well-known to those of skill in the art and include promoters capable of recognizing the T4, T3, Sp6 and T7 polymerases, the $P_R$ and $P_L$ promoters of bacteriophage lambda, the trp, recA, heat shock, and lacZ promoters of *E. coli*, the α-amylase and the sigma-specific promoters of *B. subtilis*, the promoters of the bacteriophages of *Bacillus, Streptomyces* promoters, the int promoter of bacteriophage lambda, the bla promoter of the β-lactamase gene of pBR322, and the CAT promoter of the chloramphenicol acetyl transferase gene. Prokaryotic promoters are reviewed by Glick, J. Ind. Microbiol. 1:277 (1987); Watson et al., MOLECULAR BIOLOGY OF THE GENE, 4th Ed., Benjamin Cummins (1987); Ausubel et al., supra, and Sambrook et al., supra.

The invention also provides for a host cell carrying the nucleic acids of the invention. A preferred prokaryotic host is *E. coli*. Preferred strains of *E. coli* include Y1088, Y1089, CSH18, ER1451, and ER1647 (see, for example, Brown (Ed.), MOLECULAR BIOLOGY LABFAX, Academic Press (1991)). An alternative preferred host is *Bacillus subtilus*, including such strains as BR151, YB886, MI119, MI120, and B170 (see, for example, Hardy, "*Bacillus* Cloning Methods," in DNA CLONING: A PRACTICAL APPROACH, Glover (Ed.), IRL Press (1985)). Other host include mammalian cells.

Methods for expressing nucleic acids are well-known to those of skill in the art. See, for example, Ward et al., "Genetic Manipulation and Expression of Antibodies," in MONOCLONAL ANTIBODIES: PRINCIPLES AND APPLICATIONS, pages 137-185 (Wiley-Liss, Inc. 1995). Moreover, expression systems for cloning antibodies in prokaryotic cells are commercially available. For example, the IMMUNO ZAP™ Cloning and Expression System (Stratagene Cloning Systems; La Jolla, Calif.) provides vectors for the expression of antibody light and heavy chains in *E. coli*.

The nucleic acids of the invention is preferably expressed in eukaryotic cells, and especially mammalian, insect, and yeast cells. Especially preferred eukaryotic hosts are mammalian cells. Mammalian cells provide post-translational modifications to the cloned polypeptide including proper folding and glycosylation. For example, such mammalian host cells include COS-7 cells (ATCC CRL 1651), non-secreting myeloma cells (SP2/0-AG14; ATCC CRL 1581), rat pituitary cells ($GH_1$; ATCC CCL 82), and rat hepatoma cells (H-4-II-E; ATCC CRL 1548).

For a mammalian host, the transcriptional and translational regulatory signals may be derived from viral sources, such as adenovirus, bovine papilloma virus, and simian virus. In addition, promoters from mammalian expression products, such as actin, collagen, or myosin, can be employed. Alternatively, a prokaryotic promoter (such as the bacteriophage T3 RNA polymerase promoter) can be employed, wherein the prokaryotic promoter is regulated by a eukaryotic promoter (for example, see Zhou et al., Mol. Cell. Biol. 10:4529 (1990); Kaufman et al., Nucl. Acids Res. 19:4485 (1991)). Transcriptional initiation regulatory signals may be selected which allow for repression or activation, so that expression of the genes can be modulated. In general, eukaryotic regulatory regions will include a promoter region sufficient to direct the initiation of RNA synthesis. Such eukaryotic promoters include the promoter of the mouse metallothionein I gene (Hamer et al., J. Mol. Appl. Gen. 1:273 (1982)); the TK promoter of Herpes virus (McKnight, Cell 31:355 (1982)); the SV40 early promoter (Benoist et al., Nature (London) 290:304 (1981)); the Rous sarcoma virus promoter (Gorman et al., supra); the cytomegalovirus promoter (Foecking et al., Gene 45:101 (1980)); the yeast gal4 gene promoter (Johnston, et al., Proc. Natl. Acad. Sci. (USA) 79:6971 (1982); Silver et al., Proc. Natl. Acad. Sci. (USA) 81:5951 (1984)); and the IgG promoter (Orlandi et al., Proc. Natl. Acad. Sci. USA 86:3833 (1989)).

Strong regulatory sequences are the most preferred regulatory sequences of the present invention. Examples of such preferred regulatory sequences include the SV40 promoter-enhancer (Gorman, "High Efficiency Gene Transfer into Mammalian cells," in DNA CLONING: A PRACTICAL APPROACH, Volume II, Glover (Ed.), IRL Press pp. 143-190 (1985)), the hCMV-MIE promoter-enhancer (Bebbington et al., Bio/Technology 10: 169 (1992)), and antibody heavy chain promoter (Orlandi et al., Proc. Natl. Acad. Sci. USA 86:3833 (1989)). Also preferred are the kappa chain enhancer for the expression of the light chain and the IgH enhance (Gillies, "Design of Expression Vectors and Mammalian Cell Systems Suitable for Engineered Antibodies," in Antibody Engineering: A Practical Guide, C. Borrebaeck (Ed.), W. H. Freeman and Company, pp. 139-157 (1992); Orlandi et al., supra).

The PPC sequence and an operably linked promoter may be introduced into eukaryotic cells as a non-replicating DNA molecule, which may be either a linear molecule or, more preferably, a closed covalent circular molecule. Since such molecules are incapable of autonomous replication, the expression of the protein may occur through the transient expression of the introduced sequence. Preferably, permanent expression occurs through the integration of the introduced sequence into the host chromosome.

Preferably, the introduced sequence will be incorporated into a plasmid or viral vector that is capable of autonomous replication in the recipient host. Several possible vector systems are available for this purpose. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired genomic or cDNA sequences into the host chromosome.

Additional elements may also be needed for optimal synthesis of mRNA. These elements may include splice signals, as well as transcription promoters, enhancers, and termination signals. The cDNA expression vectors incorporating such elements include those described by Okayama, Mol. Cell. Biol. 3:280 (1983), Sambrook et al., supra, Ausubel et al., supra, Bebbington et al., supra, Orlandi et al., supra, and Fouser et al., Bio/Technology 10:1121 (1992); Gillies, supra. Genomic DNA expression vectors which include intron sequences are described by Orlandi et al., supra. Also, see generally, Lerner et al. (Eds.), NEW TECHNIQUES IN ANTIBODY GENERATION, Methods 2(2) (1991).

Methods Involving Targetable Constructs

The invention also provides for a method of treating or diagnosing a disorder. In the method, an PPC of the invention which has at least (A) one ABS specific for an epitope of a targeted tissue and (B) one ABS specific for a targetable construct is provided is administered to the patient. Following the administration of the PPC, the targetable construct is administered to the patient. The PPC and the targetable construct may be administered to the patient at substantially the same time.

The targetable construct, for the purposes of this disclosure may be of two formulas.

In the first structure, the targetable construct is a compound of the formula:

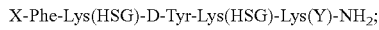

where the compound includes a hard acid cation chelator at X or Y, and a soft acid cation chelator at remaining X or Y; and wherein the compound further comprises at least one diagnostic or therapeutic cation, and/or one or more chelated or chemically bound therapeutic agent, diagnostic agent, or enzyme (described elsewhere in this disclosure). The diagnostic agent could be, for example, Gd(III), Eu(III), Dy(III), Pr(III), Pa(IV), Mn(II), Cr(III), Co(III), Fe(III), Cu(II), Ni(II), Ti(III), V(IV) ions or a radical.

In the second formula, the targetable construct is a compound of the formula:

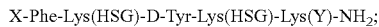

where the compound includes a hard acid cation chelator or a soft acid cheator at X or Y, and nothing at the remaining X or Y; and wherein the compound further comprises at least one diagnostic or therapeutic cation, and/or one or more chelated or chemically bound therapeutic agent, diagnostic agent, or enzyme (described elsewhere in this disclosure). The diagnostic agent could be, for example, Gd(III), Eu(III), Dy(III), Pr(III), Pa(IV), Mn(II), Cr(III), Co(III), Fe(III), Cu(II), Ni(II), Ti(III), V(IV) ions or a radical.

Any method of the invention that uses a targetable construct may also use a combination of targetable constructs. In a preferred embodiment, the targetable constructs are IMP241, IMP281 (FIG. 9A), IMP284 (FIG. 9B), IMP288, or a combination thereof.

In this method, a clearing composition may be optionally administered to the patient to clear non-localized PPC from circulation. The clearing compound is administered after the administration of the PPC but before the administration of the targetable construct. These methods are described in detail in U.S. Pat. No. 4,624,846, WO 92/19273, and Sharkey et al., Int. J. Cancer 51: 266 (1992).

The described method may be used for in vivo diagnosis. The method of diagnostic imaging with radiolabeled monoclonal antibodies is well-known and is applicable for the PPC of this invention. In the technique of immunoscintigraphy, for example, antibodies are labeled with a γ-emitting radioisotope and introduced into a patient. A γ camera is used to detect the location and distribution of γ-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 990), Brown, "Clinical Use of Monoclonal Antibodies," in BIOTECHNOLOGY AND PHARMACY 227-49, Pezzuto et al. (eds.) (Chapman & Hall 1993), and Goldenberg, Calif.—A Cancer Journal for Clinicians 44: 43 (1994). The methods of the invention may be practiced, for example, by the substitution of the monoclonal antibodies of the above referenced techniques with the PPCs of the invention.

For diagnostic imaging, radioisotopes may be bound to a PPC either directly, or indirectly by using an intermediary functional group. Useful intermediary functional groups include chelators such as ethylenediaminetetraacetic acid and diethylenetriaminepentaacetic acid. For example, see U.S. Pat. No. 5,057,313 and U.S. Pat. No. 5,128,119.

For purely diagnostic purposes (as opposed to therapeutic or diagnostic/therapeutic purposes) radiation dose delivered to the patient is maintained at as low a level as possible by choosing an isotope with the best combination of minimum half-life, minimum retention in the body, and minimum quantity of isotope which will permit detection and accurate measurement. Examples of radioisotopes that can be bound to the PPC and are appropriate for diagnostic imaging include γ-emitters and positron-emitters such as $^{99}$Tc, $^{67}$Ga, $^{111}$In, $^{123}$I, $^{124}$I, $^{125}$I, $^{131}$I, $^{51}$Cr, $^{89}$Zr, $^{18}$F and $^{68}$Ga. Other suitable radioisotopes are known to those of skill in the art. Preferred γ-emitters have a γ radiation emission peak in the range of 50-500 Kev, primarily because the state of the art for radiation detectors currently favors such labels. Examples of such γ-emitters include $^{99}$Tc, $^{67}$Ga, $^{123}$I, $^{125}$I and $^{131}$I.

The PPCs also can be labeled with paramagnetic ions for purposes of in vivo diagnosis. Elements that are particularly useful for magnetic resonance imaging include Gd, Mn, Dy and Fe ions. Other methods for enhancing in vivo diagnosis may be found, for example, in U.S. Pat. Nos. 6,096,089, 5,965,131 and 5,958,048.

In an alternate approach, detection methods are improved by taking advantage of the binding between avidin/streptavidin and biotin. Avidin, found in egg whites, has a very high binding affinity for biotin, which is a B-complex vitamin. Streptavidin, isolated from *Streptomyces avidinii*, is similar to avidin, but has lower non-specific tissue binding and therefore, streptavidin often is used in place of avidin. A basic diagnostic method comprises administering a PPC composite conjugated with avidin/streptavidin (or biotin), injecting a clearing composition comprising biotin (or avidin/streptavidin), and administering a conjugate of a diagnostic agent and biotin (or avidin/streptavidin). Preferably, the biotin (or avidin/streptavidin) component of the clearing composition is coupled with a carbohydrate moiety (such as dextran) or a polyol group (e.g., polyethylene glycol) to decrease immunogenicity and permit repeated applications.

A modification of the basic method is performed by parenterally injecting a mammal with a PPC which has been conjugated with avidin/streptavidin (or biotin), injecting a clearing composition comprising biotin (or avidin/streptavidin), and parenterally injecting a polyspecific PPC according to the present invention, which further comprises avidin/streptavidin (or biotin). See WO 94/04702.

In a further variation of this method, improved detection can be achieved by conjugating multiple avidin/streptavidin or biotin moieties to a polymer which, in turn, is conjugated to a PPC component. Adapted to the present invention, monospecific or polyspecific PPCs can be produced which contain multiple avidin/streptavidin or biotin moieties. Techniques for constructing and using multiavidin/multistreptavidin and/or multibiotin polymer conjugates to obtain amplification of targeting are disclosed by Griffiths, PCT application number PCT/US94/04295.

In another variation, improved detection is achieved by injecting a targeting PPC composite conjugated to biotin (or avidin/streptavidin), injecting at least one dose of an avidin/streptavidin (or biotin) clearing agent, and injecting a diagnostic composition comprising a conjugate of biotin (or avidin/streptavidin) and a naturally occurring metal atom chelating protein which is chelated with a metal detection agent. Suitable targeting proteins according to the present invention would be ferritin, metallothioneins, ferredoxins, and the like. See, PCT/US94/05149.

In another embodiment, the methods of the invention may be used for therapy. In the therapeutic methods, a suitable therapeutic agent is selected from the group consisting of radioisotope, boron addend, immunomodulator, toxin, photoactive agent or dye, cancer chemotherapeutic drug, antiviral drug, antifungal drug, antibacterial drug, antiprotozoal drug and chemosensitizing agent (See, U.S. Pat. Nos. 4,925,648, 4,932,412). Suitable chemotherapeutic agents are described in REMINGTON'S PHARMACEUTICAL SCIENCES, 19th Ed. (Mack Publishing Co. 1995), and in Goodman and Gilman's THE PHARMACOLOGICAL BASIS OF THERAPEUTICS (Goodman et al., Eds. Macmillan Publishing Co., New York, 1980 and 2001 editions). Moreover a suitable therapeutic radioisotope is selected from the group consisting of α-emitters, β-emitters, .γ.-emitters, Auger electron emitters, neutron capturing agents that emit α-particles and radioisotopes that decay by electron capture. Preferably, the radioisotope is selected from the group consisting of $^{225}$Ac, $^{198}$Au, $^{32}$P, $^{125}$I, $^{131}$I, $^{90}$Y, $^{186}$Re, $^{188}$Re, $^{67}$Cu, $^{177}$Lu, $^{213}$Bi, $^{10}$B, and $^{211}$At.

Boron, when used as a therapeutic agent is useful in boron neutron capture therapy (BNCT). BNCT is based on the nuclear reaction which occurs when a stable isotope, B-10 (present in 19.8% natural abundance), is irradiated with thermal neutrons to produce an α particle and a Li-7 nucleus. These particles have a path length of about one cell diameter, resulting in high linear energy transfer. Just a few of the short-range 1.7 MeV α particles produced in this nuclear reaction are sufficient to target the cell nucleus and destroy it. Barth et al., Cancer, 70: 2995-3007 (1992). Since the $^{10}$B(n, α)$_7$ Li reaction will occur, and thereby produce significant biological effect, only when there is a sufficient number of thermal neutrons and a critical amount of B-10 localized around or within the malignant cell, the radiation produced is localized. The neutron capture cross section of B-10 far exceeds that of nitrogen and hydrogen found in tissues, which also can undergo capture reactions, (relative numbers: 1 for N-14, 5.3 for H-1, and 11560 for B-10), so that once a high concentration differential of B-10 is achieved between normal and malignant cells, only the latter will be affected upon neutron irradiation. This is the scientific basis for boron neutron capture therapy. This method is described in more detail in Barth et al., supra; Barth et al. Cancer Res., 50: 1061-70 (1990); Perks et al., Brit. J. Radiol., 61: 1115-26 (1988).

Therapeutic preparations contemplated herein comprise PPC comprising an ABS specific for an epitope of a pathogen. This PPC is conjugated to a therapeutically effective radioisotope and/or antibiotic/cytotoxic drug, in a suitable vehicle for parenteral administration. A therapeutic preparation may likewise comprise a polyspecific anti-pathogen PPC composite conjugated to a radioisotope and/or antibiotic/cytotoxic drug.

It is advantageous in certain cases to combine a drug with a radionuclide, especially where the pathogen "hides" or is somewhat inaccessible. The longer range action of radionuclides can reach hidden pathogen so long as some antigen is accessible to the conjugate. Also, radiation can cause lysis of an infected cell and expose intracellular pathogen to the antimicrobial drug component of the conjugate.

The anti-microbial polyspecific imaging PPCs and monospecific or polyspecific therapeutic PPCs according to the invention also can be conveniently provided in a therapeutic or diagnostic kit for PPC targeting to a focus of infection. Typically, such a kit will comprise a vial containing the PPC conjugate of the present invention, either as a lyophilized preparation or in an injection vehicle. If the conjugate is to be used for scintigraphic imaging or for radioisotope therapy, it will generally be provided as a cold conjugate together with reagents and accessories for radiolabeling, in separate containers, while MRI agents and therapeutic drug/toxin conjugates will generally be supplied with a paramagnetic species or an antibiotic/cytotoxic agent already conjugated to the PPC. The kit may further contain a second, separately packaged, unlabeled PPC specific the therapeutic agent, a carrier therefor, or a chelating agent for the radionuclide or paramagnetic ion.

It is well known in the art that various methods of radionuclide therapy can be used for the treatment of cancer and other pathological conditions, as described. e.g., in Harbert, "Nuclear Medicine Therapy", New York, Thieme Medical Publishers, 1087, pp. 1-340. A clinician experienced in these procedures will readily be able to adapt the cytokine adjuvant therapy described herein to such procedures to mitigate the hematopoietic side effects thereof. Similarly, therapy with cytotoxic drugs, either administered alone or as PPC conjugates for more precisely targeted therapy. e.g., for treatment of cancer, infectious or autoimmune diseases, and for organ rejection therapy, is governed by analogous principles to radioisotope therapy with isotopes or radiolabeled antibodies. Thus, the ordinary skilled clinician will be able to adapt the description of cytokine use to mitigate marrow suppression and other such hematopoictic side effects by administration of the cytokine before, during and/or after drug therapy.

Therapeutically useful immunoconjugates can be obtained by conjugating photoactive agents or dyes to a PPC of the invention. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al., (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130:1473 (1983); idem., Cancer Res. 45:4380 (1985); Oseroff et al., Proc. Natl. Acad. Sci. USA 83:8744 (1986); idem., Photochem. Photobiol. 46:83 (1987); Hasan et al, Prog. Clin. Biol. Res. 288:471 (1989); Tatsuta et al., Lasers Surg. Med. 9:422 (1989); Pelegrin et al., Cancer 67:2529 (1991). The present invention contemplates the therapeutic use of PPC comprising photoactive agents or dyes. Anti-CD19 and anti-CD20 antibodies are known to those of skill in the art. See, for example, Ghetie et al, Cancer Res. 48:2610 (1988); Hekrnan et al., Cancer Immunol. Immunother. 32:364 (1991); Kaminski et al., N. Engl. J. Med. 329:459 (1993); Press et al., N. Engl. J. Med. 329:1219 (1993); Maloney et al., Blood 84:2457 (1994); Press et al., Lancet 346:336 (1995); Longo, Curr. Opin. Oncol. 8:353 (1996).

The targetable construct may contain $^{10}$B atoms. In this case, the method may comprise an additional step of effecting BNCT of a diseased tissue (including neoplastic tissue) where the targetable construct is located. See U.S. Pat. Nos. 5,846,741, 6,228,362 for a discussion of BNCT.

In another embodiment of the invention, the targetable construct of the method may comprise an enzyme. The enzyme may be one that can increase the cytotoxicity of a drug. For example, the enzyme may convert a drug from a nontoxic form to a toxic form. Alternatively, the enzyme may convert a toxic drug to an even more toxic drug. Examples of such enzyme-prodrug binding partners are I-131-antibody-carboxypeptidase G2 and topoisomerase-inhibiting prodrug CPT-11; β-lactamase and cephalosporin-doxorubicin; alkaline phosphatase and etoposide phosphate; carboxypeptidase G2 and glutamic acid derivative of benzoic acid mustard; and β-glucuronidase and the glucuronide of any drug which can form a glucuronide, such as p-hydroxyaniline mustard. Other examples of targeted enzymes for prodrug activation are discussed in Bioconjuate Chem., Vol. 4, (1), 3-9 (1993).

In the methods where the PPC is labeled or the targetable construct is labeled, the method may be used to detect a target cell, target tissue, or a pathogen (i.e., infectious agent) in a patient.

Methods for Producing PPC

The invention also provides for methods for producing the PPC of the invention. In one embodiment, the methods comprise providing a first polypeptide having an amino acid sequence comprising 3 or 4 v-regions (i.e., $a_1$, $a_2$, $a_3$, etc.) linearly arranged in the polypeptide sequence, optionally comprising amino acid linking sequences interspersed between the v-regions, and providing a second polypeptide having an amino acid sequence comprising 3 or 4 v-regions (i.e., $b_1$, $b_2$, $b_3$, etc.) linearly arranged in the polypeptide sequence, optionally comprising amino acid linking sequences interspersed between the v-regions; and contacting the first and second polypeptides under appropriate conditions such that the individual polypeptide chains arrange laterally to one another and bind to one another by the complementarity binding of corresponding v-regions (i.e. $a_1$ to $b_1$, $a_2$ to $b_2$, $a_3$ to $b_3$, etc.) to form the PPC.

The methods of producing the PPC's may be performed, for example, by producing the polypeptides on a peptide synthesizer and combining them in solution under appropriate conditions to allow for the complementarity binding of the individual polypeptide chains. Those of ordinary skill in the art are aware of several such methods for combining the individual polypeptide chains. For example polypeptide 1 and polypeptide 2 of a PPC may be synthesized on a peptide synthesizer using following the manufacturer's instruction (e.g., Applied Biosystems). Alternatively, peptides may be ordered by mail from a commercial laboratory (e.g., Sigma-Genosys, The Woodlands, Tex.). The dried peptides may be mixed and solubilized in water or water with 5% $NH_4OH$ to produce the PPC.

In a preferred embodiment, the two PPC polypeptides may be coexpressing in a host cell. For example, an expression plasmid (referred to herein as the coexpression plasmid) that can co-express two different genes inserted into two different cloning sites may be chosen (e.g., BS14HP-GAP+). Nucleic acid molecules with open reading frames that encode polypeptide 1 and polypeptide 2 of PPC may be cloned into the two cloning sites. The nucleic acid molecules may be cloned by traditional techniques or they may be synthesized using an oligonucleotide synthesizer. The coexpression plasmid may be transfected into a eukaryotic host such as a yeast cell for expression. PPC may be produced by culturing the eukaryotic host cell culture until a desired quantity of PPC is produced.

In any of the production methods of the invention, the produced PPC may be a tagged PPC. Tagged PPC may comprise an additional peptide sequence, such as the FLAG sequence or the polyHIS sequence. This sequence would allow any expressed PPC to be purified with the proper affinity column.

Another example of a suitable expression system for diabodies and triabodies (which includes the PPC of this invention) is the pdHL2 vector, which has an amplifiable murine dhfr gene that allows subsequent selection and amplification by methotrexate treatment. Gillies et al., J. Immunol. Methods 125:191 (1989). The pdHL2 vector provides independent expression of two genes that are independently controlled by two metallothionine promoters and IgH enhancers. One example of using an amplifiable selectable marker to increase expression in a mammalian recombinant host cell line is shown in Example 2.

Suitable host cells or cell lines for the expression of the PPC of the invention are known to one of skill in the art and are also listed in the definition of "host cell" above. One host cell is a human cell—which would enable any expressed molecules to be modified with human glycosylation patterns. It should be noted that there is no indication that a human host cell is essential or preferred for the methods of the invention.

As an illustration, SP2/0 cells can be transfected by electroporation with linearized pdHL2 vector that contains coding sequences for two antibody components. Selection can be initiated 48 hours after transfection by incubating cells with medium containing 0.05-0.1 µM methotrexate. Amplification of the two antibody sequences is achieved by a stepwise increase in methotrexate concentration up to 5 µM.

To ensure that the PPC was formed correctly, or for purification, the PPC may be purified by an antigen affinity column which is loaded with an antigen that is recognized by an ABS of the PPC. An antigen affinity purification column can purify only those PPC with properly formed ABS because PPC without the proper ABS should not bind to the affinity column matrix. The antigen affinity purification may be performed multiple times. For example, if the ABSs of a PPC recognize antigen 1, antigen 2 and antigen 3, the PPC may be purified by three antigen affinity purification columns each loaded with one of the three antigens. Other methods of purification, such as, for example, precipitation of proteins, size exclusion chromatography, co-precipitation and co renaturation are known to those of skill in the art.

The following examples are provided to illustrate, but not to limit, the claimed invention.

EXAMPLES

Example 1

BS14HP, a Bispecific Trivalent Heterodimer

Design.

BS14HP was designed for the constitutive expression of foreign genes in *Pichia pastoris* using the GAP promoter system. Transfection of *P. pastoris* cells with a linearized DNA plasmid (BS14HP-GAP+) results in the stable and site-specific integration of the two DNA segments (FIG. 1A) into the GAP locus of the host's chromosome. These two DNA segments contain open reading frames, SEQ ID NO:49 and SEQ ID NO:10, which code for polypeptide 1 (SEQ ID NO:1) and polypeptide 2 (SEQ ID NO:2) respectively. As each of the two DNA segments also contains nucleotide sequences for the GAP promoter, two mRNA species that encode the amino acid sequences of polypeptide 1 and polypeptide 2 are synthesized in the same host cell.

Polypeptide 1.
(SEQ ID NO: 1)
α-Factor-h679$V_H$-GGGGS-hMN-14$V_K$-LEGGGS-hMN-14$V_H$-

6His

Polypeptide 2.
(SEQ ID NO: 2)
α-Factor-hMN-14$V_K$-GGGQFM-hMN-14$V_H$-GGGGS-h679$V_K$-

6His

The "α-factor," as shown in the schematic of polypeptide 1 and 2 above, represents a signal peptide that is removed during synthesis and protein transport, resulting in secretion of the protein (without the signal peptide) into the media. The carboxyl terminal hexa-histadine (6His) sequence (SEQ ID NO: 20) allows for rapid and efficient purification of the secreted protein with commercially available immobilized metal affinity chromatography (IMAC) material. hMN-14$V_H$ represents the amino acid sequence of the variable region of the heavy chain of ($V_H$ region) a humanized monoclonal antibody (Mab) that binds specifically to carcinoembryonic antigen (CEA; Shevitz et al, J. Nucl. Med., suppl., 34, 217P, 1993). h679$V_K$ represents the light chain variable region of the humanized murine monoclonal antibody designated 679 (an antibody of the IgG1, kappa class), which binds with high affinity to molecules containing the tri-peptide moiety histamine-succinyl-glycyl (referred to herein as "HSG"; Morel et al, Molecular immunology, 27, 995-1000, 1990). The nucleotide sequence pertaining to the variable domains ($V_H$ and $V_K$) of 679 has been determined (Qu et al, unpublished results). Humanized versions of the 679 variable domains (Rossi. et al, unpublished results) were used in the design of this construct.

The short peptide linkers, GGGGS (SEQ ID NO: 16), LEGGGS (SEQ ID NO: 17), GGGQFM (SEQ ID NO: 18), and GGGGS (SEQ ID NO: 19), between the variable domains in the constructs are designed to discourage intra-polypeptide domain pairing. It is anticipated that the two different polypeptides (FIG. 1B) would associate with each other non-covalently by pairing the cognate $V_H$ and $V_K$ domains and thereby forming two functional binding sites for CEA and one functional binding site for HSG as shown in FIG. 1C.

pGAPZα Modified Vector

The novel construct pGAPZα+, depicted in FIG. 2, was engineered to make bispecific constructs through the synthesis of two heterologous polypeptides from a single *Pichia* host cell. Two overlapping oligonucleotides, which constitute the SS1 linker, were synthesized, phosphorylated with T4 polynucleotide kinase and annealed by heating to 95° C. and then slowly cooling to room temperature over 30 minutes.

```
SS1 Linker Top
5'-gatcccctgc agggagctca ctagta-3'   (SEQ ID NO: 3)

SS1 Linker bottom
5'-gatctactag tgagctccct gcaggg-3'   (SEQ ID NO: 4)
```

The oligonucleotide duplex was ligated into the BamHI site of the pGAPZαA vector (Invitrogen) and transformants were screened for the presence of the linker in the proper orientation Construction of the *Pichia* Expression Plasmid BS14HP-GAP+

Cloning of BS14-Orf-1-pGAPzα+

Using the plasmid construct hMN-14$V_H$-L5-h679VK-GAP+ (Rossi et al, unpublished results) as a template, a PCR reaction was performed to generate the amplimer XhoI-L6-hMN-14$V_H$-SalI using the following oligonucleotide primers:

```
L6-hMN14VH Xho Left
                                     (SEQ ID NO: 5)
5'-catactcgagggcggaggtagcgaggtccaactggtggagagc-3' hMN14V_H SalI Right
                                     (SEQ ID NO: 6)
5'-cttagtcgacggagacggtgaccggggtc-3'
```

The PCR amplimer was cloned into pGemT vector (Promega) and screened for clones inserted in the 5'-T7 orientation. This construct, L6-hMN-14-pGemT(T7), was digested with NcoI and XhoI restriction enzymes and ligated with a DNA fragment containing h679$V_H$-L5-hMN14$V_K$ that was excised from the h679$V_H$-L5-hMN-14VK-GAP+ plasmid construct (Rossi et al, unpublished results) with NcoI and XhoI restriction enzymes to generate the construct to generate the staging plasmid construct BS14HP orf1-pGemT. This staging construct was first digested with NcoI restriction endonuclease and the ends were made blunt by filling with the Klenow fragment of the DNA polymerase. Following the Klenow fragment treatment, the DNA molecule was digested with SalI restriction endonuclease to generate a fragment named BS14HP-orf1. The pGAPZα+ vector (FIG. 2) was first digested with EcoRI restriction endonuclease and the ends were made blunt by filling with Klenow enzyme, and then it was digested with SalI. The digested vector was ligated with the insert fragment to generate BS14orf1-pGAPzα+.

Cloning of BS14-orf2-pGAPZα+AVRX

A PCR reaction was performed to generate the amplimer EcoRI-L5-hMN-14$V_K$-L5-MfeI using the plasmid construct h679$V_H$-L5-hMN-14VK-GAP+ (Rossi et al, unpublished results) as a template and the following primers:

```
HMN-14VK EcoRI Left
                                     (SEQ ID NO: 7)
5'-ctaggaattc gacatccagc tgacccagag-3' hMN14V_K-L5 MfeI Right
                                     (SEQ ID NO: 8)
5'-cgtacaattg gccacctcca cgtttgattt ccaccttgg-3'
```

The amplimer was digested with EcoRI and MfeI restriction enzymes and ligated with the plasmid construct hMN-14$V_H$-L5-h679VK-AvrX (Rossi et al, unpublished results) that was digested with EcoRI to generate the construct BS14HP-orf2-pGAPZα+AVRX.

Final Assembly of BS14HP-GAP+

The construct BS14HP-orf2-pGAPZα+AVRX was digested with NsiI and SpeI and separated by agarose gel electrophoresis. A 2260 bp DNA fragment containing the BS14-orf2 coding sequence was isolated from the agarose gel. This isolated nucleic acid molecule was digested with SbfI and SpeI restriction endonuclease and ligated with the NsiI/SpeI BS14-orf2 fragment (discussed above) to generate the final construct BS14HP-GAP+

Constitutive Expression of BS14HP in *Pichia Pastoris*

The BS14HP-GAP+ construct was prepared for transfection by digestion with AvrII restriction endonuclease. This linearized construct was used to transfect the X-33 strain of *Pichia pastoris* by electroporation using standard methods. Stable transfectants were isolated on YPD-agar plates containing 100 µg/ml of zeocin. Nine zeocin-resistant colonies were re-streaked on YPD-zeocin plates and the isolated clones were used to inoculate baffled shake flasks containing modified YPD media (1% yeast extract, 2% tryptone, 2% dextrose, 0.4 µg/ml biotin, 1.34% yeast nitrogen base, 100 mM $K_2HPO_4$, pH 6.0). The flask cultures were shook at 250 RPM and 30° C. for 48-72 hours to stationary phase where the optical density at 600 nm was between 18 and 25. The media, which should contain the excreted recombinant protein, was clarified by centrifugation and assayed for active protein using a BIAcore sensorchip.

The analysis step is as follows. Samples of the culture media were diluted 1:5 in EB buffer (150 mM NaCl; 50 µM EDTA; 0.005% surfactant P20; 10 mM HEPES, pH 7.4) and injected (501) over a high-density, HSG-coupled sensorchip in a BIAcoreX system. Following injection of the diluted media, EB containing 20 µg/ml of WI2 IgG, an anti idiotypic antibody to hMN-14, was injected (100 µg) over the sensorchip to confirm bispecific binding. The initial binding slopes were used to quantitate yields. Seven of the nine zeocin resistant clones tested produced bispecific protein with a yield of up to 3 mg per liter of culture media.

To purify a larger amount of recombinant protein, the culture media from the highest expressing clone was buffer exchanged by diafiltration into Ni Binding buffer (300 mM NaCl; 10 mM imidazole; 50 mM $NaH_2PO_4$, pH 8.0). Following buffer exchange, the media protein was loaded onto Ni-NTA IMAC affinity column. The column was washed extensively with buffer containing 20 mM imidazole and eluded with a buffer containing 250 mM imidazole (250 mM imidazole; 50 mM NaCl; 25 mM Tris, pH 7.5). The eluates were analyzed by BIAcore, as described above, and all of the binding activity was retained (FIG. 3).

Biochemical Analysis of BS14HP

To assay the expressed and purified BS14HP, a protein sample was analyzed by reducing SDS-PAGE and visualized by Coomassie blue-stained SDS-PAGE gel. The results, as shown in FIG. 4, showed that the samples are were highly purified and lack significant protein contamination. The purified protein complex were resolved in the SDS-PAGE gel as comprising two similar sized c (i.e., closely spaced bands) polypeptide chain that migrate in the gel at a rate that is near expected molecular weights of 40,614 and 40,061 Daltons.

To further analyze the expressed product, the expressed protein was analyzed by MALDI TOF mass spectrometry and size exclusion HPLC analysis. Both analysis of expressed BS14HP gave a single peak consistent with an 81 kDa dimeric protein structure (FIG. 5).

The binding stoichiometry can be extrapolated from BIAcore sensorgrams such as the one shown in FIG. 3. The W12:BS14HP molar binding ratio can be derived by comparison of the response units (RU) attained from BS14HP binding to the HSG sensorchip with the further RU increase from W12 binding to BS14HP with normalization for the respective molecular weights. Several BS14HP preps were analyzed with the measured ratio ranging from 0.8-0.9. This ratio indicates the presence of two functional CEA binding sites per molecule, as the theoretical maximum ratio for such a protein is 1.0. As a comparison, a variety of monovalent CEA-binding bispecific (hMN-14×679) constructs all gave molar ratios between 0.4 and 0.45.

Figure 6A:
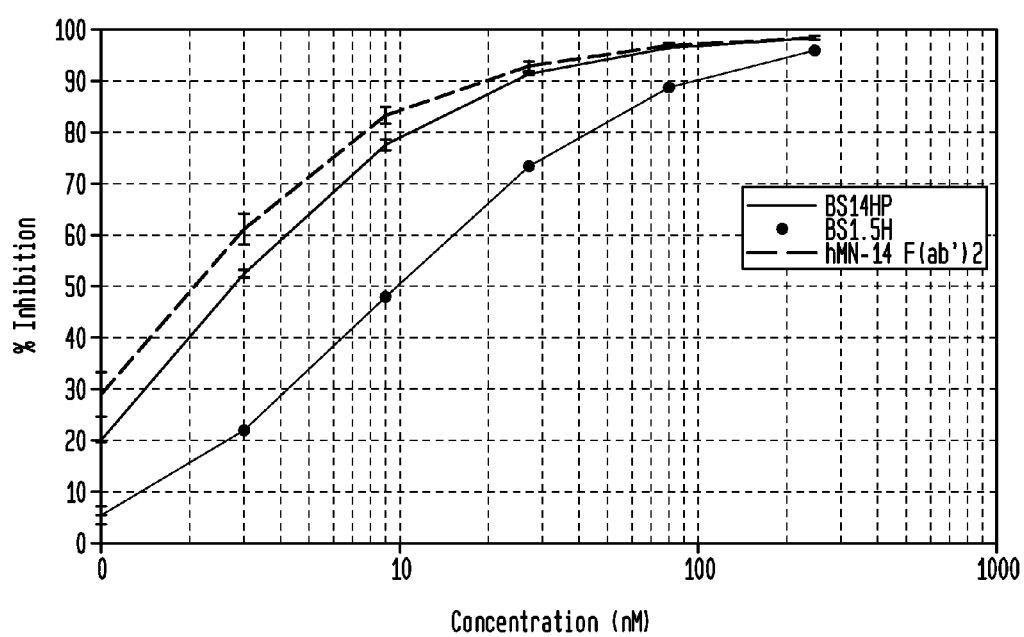

The CEA binding of BS14HP was analyzed in a competitive ELISA and compared to BS1.5H and hMN-14F(ab')$_2$, which have one and two CEA binding groups, respectively (FIG. 6A). HRP-conjugated hMN-14 IgG (1 nM) was mixed with either BS14HP, SB1.5H or hMN-14 F(ab')$_2$ at concentrations ranging from 1 to 250 nM, prior to incubation in CEA-coated (0.5 μg/well) wells. The $IC_{50}$ for BS14HP was 2.7 nM which is close to 2.0 nM for hMN14 F(ab')$_2$. The monovalent CEA binder, BS1.5H, had an $IC_{50}$ of 10 nM. These results are consistent with the BIAcore analysis in demonstrating that BS14HP binds CEA divalently. Further, the binding avidity is comparable to that of the native hMN-14 F(ab')$_2$.

Confirmation that BS14HP has the ability to bind CEA bivalently was provided by SE-HPLC analysis of in vitro immunoreactivity. When increasing amounts of CEA were mixed with $^{125}$I-hBS14, two distinct peak shifts were evident by HPLC corresponding to complexes of $^{125}$I-hBS14 bound to either one or two CEAs. (FIG. 6B).

In Vivo Analysis of BS14HP

The utility of BS14HP for tumor pretargeting was evaluated in GW-39 tumor-bearing mice using a bivalent HSG peptide (IMP-241) labeled with $^{111}$In. IMP-241 has a structure of DOTA-Phe-Lys(HSG)-D-Tyr-Lys(HSG)-NH2, where the N-terminal amino group of Phe is linked to a DOTA and the epsilon amino group of each lysine is derivatived with an HSG group. The tetrapeptide backbone (Phe-Lys-(D-Tyr)-Lys) contains a d-amino acid (D-Tyr) and the carboxyl group of the C-terminal lys is amidated.

The results from this analysis were compared with those of chemically linked hMN-14×679 (Fab'×Fab') and BS1.5H (bispecific diabody). Nude mice bearing GW-39 (CEA positive) tumors were pre-targeted with BS14HP, BS1.5H or hMN-14×679. Initially, the bio-distribution was followed with $^{131}$I-labeled bispecific agent. The tumor residence and blood clearance of $^{131}$I-BS14HP is depicted in FIG. 7. As determined in preliminary experiments, the time interval between administration of bispecific targeting agent and of $^{111}$In-IMP241 peptide is the amount of time required for the former to clear the blood to a concentration of 1% ID/g or less. A pre-targeting clearance time of 24 hours was used for BS14HP and hMN-14×679. A 15-hour clearance time was used for the smaller BS1.5H, which clears the blood more rapidly. IMP-241 (Immunomedics, Inc), a peptide containing two HSG groups and a DOTA moiety, was loaded with $^{111}$Indium and injected in pre-targeted mice. The bio-distribution of the $^{111}$In-IMP-241 was examined at 3 hours after injection (FIG. 8A) and the tumor/non-tumor ratios are shown in FIG. 8B.

The results indicate that approximately three-fold more $^{111}$In-IMP241 peptide was specifically bound to the tumor in mice pretargeted with BS14HP, as compared to mice pretargeted with either BS1.5H or hMN14×679. The radioactivity in all non-tumor organs was low and comparable amongst the three pretargeting agents.

These experiments were performed again using polypeptide IMP281 (FIG. 9A), IMP284 (FIG. 9B), and IMP288 (FIG. 9C) with the same results.

Example 2 hBS14, a Bispecific Trivalent Heterodimer Expressed in Myeloma Cells

To demonstrate that similar PPCs could be made from other types of host cell systems we developed a scheme for production of a fusion protein named hBS14 in mammalian cell culture. The hBS14 PPC produced in mammalian cell culture was designed to be structurally and functionally similar to BS14HP, which was produced in the yeast P. pastoris (example 1). A DNA plasmid vector was engineered for hBS14 expression and used to generate transgenic cell lines in SP2/0-Ag14 mouse myeloma cells, NS0 mouse myeloma, and YB2/0 rat myeloma cells. While these particular cell lines were used, it is understood that the vectors of the invention may be used in any mammalian cell lines, such as, for example, a human cell line.

Generation of an hBS14 DNA Expression Vector

The nucleic acid encoding the hBS14 polypeptides were recombinantly inserted into the mammalian expression vector pdHL2, which permits the amplification of antibody production. The pdHL2 vector contains the genes for IgG constant regions ($C_H$ an $C_K$) and was originally designed to accept variable domain cassettes and direct the synthesis of whole IgG. Since we are interested in expressing novel single chain-based constructs devoid of constant region sequences, it was necessary to create a new shuttle vector to facilitate the assembly and transfer of the hBS14 genes into the pdHL2 vector. See FIG. 10A.

Overlapping synthetic oligonucleotides (85mers) were annealed to form duplex DNA possessing the features shown in FIG. 10A. This duplex was ligated into the HindIII and EcoRI restriction endonuclease sites of the pGEM3z cloning vector (Promega) to generate the SV3 shuttle vector. The variable domain genes were amplified by PCR from BS14HP-GAP+(example 1) and assembled into open reading frames (ORFs) in the SV3 shuttle vector via the NcoI and SalI restriction endonuclease sites. SV3 constructs were generated for both ORF1 and ORF 2, which encode polypeptides 1 and 2 (See FIG. 10B).

Each ORF includes the IgG light chain leader peptide, which directs secretion of the nascent polypeptides, preceding the variable domain genes, which are in turn followed by the codons for six histidines and two stop codons. The variable domains are separated by linker peptides consisting of 5 or 6 amino acid residues. ORF1 and ORF2 were sub-cloned into a single pdHL2 expression vector. ORF1 was excised from its shuttle vector with Xba I and Bgl II restriction endonucleases and cloned into the XbaI and BamHI sites of pdHL2 to generate the intermediate construct hBS140RF1-pdHL2. ORF2 was then excised from its shuttle vector with XhoI and EagI restriction enzymes and cloned into those same sites of the intermediate hBS140RF1-pdHL2 construct to generate the final di-cistronic expression vector hBS14-pdHL2 (FIG. 11).

Stable Transfection and Amplification of hBS14 Genes in Sp2/0 Myeloma Cells

SP2/0-Ag14 mouse myeloma cells have been used previously in conjunction with the pdHL2 expression vector for high-level expression of recombinant IgG. NS0 mouse myeloma and YB2/0 rat myeloma cells have been used for high-level expression of recombinant IgG with other expression vectors. The hBS14-pdHL2 DNA vector was linearized by digestion with EcoRI restriction endonuclease and successfully transfected into each of the three cell lines ($4 \times 10^6$ cells) by electroporation (450 volts, 25 µF). The pdHL2 vector contains the gene for dihydrofolate reductase (DHFR) allowing clonal selection as well as gene amplification with methotrexate (MTX).

Transfectants were cloned by plating in 96-well plates in the presence of 0.05 µM MTX and the primary screening for hBS14-expressing clones was accomplished by ELISA. The ELISA screening format was as follows: A conjugate consisting of an HSG-containing peptide (IMP239) and bovine serum albumin was first adsorbed to micro-plate wells and then conditioned media from the putative clones were transferred to the micro-plate wells to allow hBS14 binding to the HSG groups of the conjugate. Bound hBS14 was detected with WI2, a rat anti-idiotype IgG to hMN-14, and HRP-conjugated goat anti-rat IgG. Several positive clones were identified and expanded. Expression of hBS14 was confirmed by BIAcore using an HSG (IMP239) sensorchip. An increase in response units (RU) following injection of culture media signified expression of hBS14. A further increase in RU with subsequent injection of WI2 demonstrated that the hBS14 was bispecific and fully functional. With this method, standard concentration curves were generated using purified 679-proteins allowing for accurate real time measurements of productivity. The initial productivity of the highest terminal culture hBS14 producer in SP2/0, YB2/0 and NSO was 0.8 mg/L, 3.7 mg/L, and 4.4 mg/L, respectively.

Gene amplification and the resulting increase in productivity were accomplished by stepwise increase in MTX concentration in the culture media over several months. An example of the increase in productivity is shown for SP2/0 clone 1H6 in FIG. 12. The MTX concentration has been increased from 0.05 µM to 1 µM and the productivity has increased to 8 mg/L, 16 mg/L and 9.3 mg/L for representative clones of SP2/0, YB2/0 and NS0, respectively without adverse effects. We expect these yields can be further improved with further MTX treatment and selection. Typically, MTX concentrations can be increased up to 5 µM with significant additional increase in productivity.

Production and Purification of hBS14

Nearly 100 mg of hBS14 has been purified to near homogeneity. Starting material was generated in terminal roller bottle cultures of each representative cell line grown with 1 µM MTX. The purification process was greatly facilitated by the generation of an HSG-based affinity purification resin. Initial attempts using affigel-IMP239, the same peptide that was used in both ELISA and BIAcore experiments, were less successful because the strong binding affinity made elution without protein denaturation. None of the myriad elution buffers tested eluted the hBS14 effectively. A new peptide (IMP291), which was designed to have $\frac{1}{10}$ to $\frac{1}{100}$ lower affinity for 679, was synthesized and conjugated to Affigel (BIO-RAD) by standard methods. The high binding capacity (>20 mg/ml) Affigel-IMP291 proved to be ideal for affinity purification of hBS14 by providing high yield, high purification and high retention of activity.

Briefly, culture media from roller bottles was clarified by cross-flow microfiltration (0.2 µM) and then pH adjusted to 4.5 with citric acid. The hBS14 in the clarified and pH adjusted media was partly purified about 25 fold by loading the media onto a S-sepharose cation exchange column. The S-sepharose column was eluted with 2×PBS (0.3 M NaCl; 80 mM $NaH_2PO_4$, pH 7.4) and the eluate was loaded onto an Affigel-IMP291 column. The column was eluted with 50 ml of 1 M imidazole; 150 mM sucrose; 0.02% Tween-20; 50 mM Citrate, pH 4.5. The eluded product was dialyzed into formulation buffer (150 mM Sucrose; 0.02% Tween-20; 10 mM NaAc, pH 4.5). This procedure allows elution of nearly 100% of the hBS14 bound to the affinity column.

Biochemical Analysis of hBS14

Basic biochemical analysis demonstrated that the purification process resulted in highly purified hBS14. The native quaternary structure of the hBS14 was designed to be a 79.4 kDa heterodimer of polypeptide 1 (39.94 kDa) and polypeptide 2 (39.5 kDa). The size exclusion HPLC profile of purified hBS14 (FIG. C) shows a major sharp peak with a retention time of 9.23 minutes, consistent with the profile of an 80 kDa protein. BS1.5H diabody (54 kDa), hMN-14 triabody (78 kDa), and hMN-14 F(ab')$_2$ (100 kDa) were run in the same column as molecular weight and size standards. These proteins had retention times of 9.60, 9.35, and 8.77 minutes, respectively. The HPLC profiles are very similar among batches purified from each cell line (FIG. C.). The peak at ~11.4 minutes is a non-protein buffer peak. The small peak at 8.30 minutes constitutes 3% of the total protein and is likely dimerized/aggregated hBS14. SDS-PAGE analysis was used to evaluate the purity and quality of the polypeptide constituents of hBS14. The Coomassie blue-stained reducing SDS-PAGE gel shown in FIG. 14 demonstrates the high degree of purity achieved from this two-step purification process. Only trace amounts of contaminating protein were detected even when a lane was overloaded with 4 µg of protein. This SDS-PAGE analysis indicates that the minor HPLC peak (8.30 min) is indeed hBS14 aggregate and not contaminating protein. The molecular weights (MW) given for polypeptides 1 and 2 were calculated from the deduced amino acid sequences of the polypeptides. The $M_r$s of the two bands are consistent with the calculated MW of the hBS14 polypeptides. As predicted, the two bands appear to be of equal intensity as they should be in equimolar concentration based on the molecular design. There is no evidence of appreciable protein degradation. Isoelectric focusing (IEF) of the purified hBS14 shows a major band near the isoelectric point (pI) of hBS14 (pI=7.73) as calculated from the deduced amino acid sequence (FIG. 15). There are trace bands at lower pI that are likely product related and may be the result of negligible deamidation of some basic amino acid residues. Taken together, this combination of standard biochemical analyses suggests that the transgenic myeloma cells correctly synthesize and secrete hBS14 as designed and that we have developed a robust purification process capable of generating highly purified material. The biochemical properties of hBS14 were indistinguishable among batches prepared from the different cell lines.

Functional characterization was provided by BIAcore experiments to demonstrate bispecific binding properties (FIG. 16). hBS14 bound tightly to HSG that was immobilized on a sensorchip. The HSG-bound proteins were able to capture subsequently added CEA or WI2, demonstrating that they can simultaneously bind both antigens. If the W12 binding is allowed to approach saturation, the stoichiometry of the binding can be determined. The additional increase in RU resulting from W12 binding was compared to the initial RU increase of the hBS14 upon binding to the HSG-sensorchip. As each increase in RU level is directly proportional to the mass bound, the WI2:bsAb molar binding ratio can be calculated using the formula $(RU_{WT2}/RU_{hBS}14) \times (MW_{hBS14}/MW_{WT2})$. hBS14 was designed to be bivalent for CEA (and monovalent for HSG) and as such should bind W12 (also bivalent) with a 1:1 molar ratio. Indeed, the experimentally determined molar binding ratio of WI2 to hBS14 was found to be between 0.7 and 0.8, approaching the theoretical maximum of 1.0. When equal concentrations of hBS14 were bound to an HSG-sensorchip, BIAcore sensorgrams are indistinguishable between lots derived from either SP2/0 or YB2/0 cells (FIG. 17).

The data demonstrate that the primary amino acid sequence is solely responsible for the structure and function of the PPC, independent of the host cell from which it is produced. The PPC hBS14 was not only equivalent among batches produced in three different mammalian cell lines, it was also very similar with respect to structure and function to BS14HP, which has similar primary amino acid sequences but is produced in yeast.

Biopolymer Sequences:

The nucleic acid and amino acid sequence of the biopolymers used in Example 2 are as follows:

hBS14 Polypeptide 1 Deduced Amino Acid Sequence:

```
                                            (SEQ ID NO: 11)
MEVQLVESGGDLVKPGGSLKLSCAASGFTFSIYTMSWLRQTPKGLEWVA

TLSGDGDDIYYPDSVKGRFTISRDNAKNSLYLQMNSLRAEDTALYYCARV

RLGDWDFDVWGQGTTVSVSSGGGGSDIQLTQSPSSLSASVGDRVTITCKA

SQDVGTSVAWYQQKPGKAPKLLIYWTSTRHTGVPSRFSGSGSGTDFTFTI

SSLQPEDIATYYCQQYSLYRSFGQGTKVEIKRLEGGGSEVQLVESGGGVV

QPGRSLRLSCSASGFDFTTYWMSWVRQAPGKGLEWIGEIHPDSSTINYAP

SLKDRFTISRDNAKNTLFLQMDSLRPEDTGVYFCASLYFGFPWFAYWGQG

TPVTVSVDHHHHHH
or (SEQ ID NO: 11)
MetGluValGlnLeuValGluSerGlyGlyAspLeuValLysProGly

GlySerLeuLysLeuSerCysAlaAlaSerGlyPheThrPheSerIle

TyrThrMetSerTrpLeuArgGlnThrProGlyLysGlyLeuGluTrp

ValAlaThrLeuSerGlyAspGlyAspAspIleTyrTyrProAspSer

ValLysGlyArgPheThrIleSerArgAspAsnAlaLysAsnSerLeu

TyrLeuGlnMetAsnSerLeuArgAlaGluAspThrAlaLeuTyrTyr

CysAlaArgValArgLeuGlyAspTrpAspPheAspValTrpGlyGln

GlyThrThrValSerValSerSerGlyGlyGlyGlySerAspIleGln

LeuThrGlnSerProSerSerLeuSerAlaSerValGlyAspArgVal

ThrIleThrCysLysAlaSerGlnAspValGlyThrSerValAlaTrp

TyrGlnGlnLysProGlyLysAlaProLysLeuLeuIleTyrTrpThr

SerThrArgHisThrGlyValProSerArgPheSerGlySerGlySer

GlyThrAspPheThrPheThrIleSerSerLeuGlnProGluAspIle

AlaThrTyrTyrCysGlnGlnTyrSerLeuTyrArgSerPheGlyGln

GlyThrLysValGluIleLysArgLeuGluGlyGlyGlySerGluVal

GlnLeuValGluSerGlyGlyGlyValValGlnProGlyArgSerLeu

ArgLeuSerCysSerAlaSerGlyPheAspPheThrThrTyrTrpMet

SerTrpValArgGlnAlaProGlyLysGlyLeuGluTrpIleGlyGlu

IleHisProAspSerSerThrIleAsnTyrAlaProSerLeuLysAsp

ArgPheThrIleSerArgAspAsnAlaLysAsnThrLeuPheLeuGln

MetAspSerLeuArgProGluAspThrGlyValTyrPheCysAlaSer

LeuTyrPheGlyPheProTrpPheAlaTyrTrpGlyGlnGlyThrPro

ValThrValSerValAspHisHisHisHisHisHis
``` hBS14 Polypeptide 2 Deduced Amino Acid Sequence:

```
                                            (SEQ ID NO: 12)
MDIQLTQSPSSLSASVGDRVTITCKASQDVGTSVAWYQQKPGKAPKLLIY

WTSTRHTGVPSRFSGSGSGTDFTFTISSLQPEDIATYYCQQYSLYRSFGQ

GTKVEIKRGGGQFMEVQLVESGGGVVQPGRSLRLSCSASGFDFTTYWMSW

VRQAPGKGLEWIGEIHPDSSTINYAPSLKDRFTISRDNAKNTLFLQMDSL

RPEDTGVYFCASLYFGFPWFAYWGQGTPVTVSGGGGSDIVMTQSPSSLAV

SPGERVTLTCKSSQSLFNSRTRKNYLGWYQQKPGQSPKLLIYWASTRESG

VPDRFSGSGSGTDFTLTINSLQAEDVAVYYCTQVYYLCTFGAGTKLELKR

LDHHHHHH.
or (SEQ ID NO: 12)
MetAspIleGlnLeuThrGlnSerProSerSerLeuSerAlaSerVal

GlyAspArgValThrIleThrCysLysAlaSerGlnAspValGlyThr

SerValAlaTrpTyrGlnGlnLysProGlyLysAlaProLysLeuLeu

IleTyrTrpThrSerThrArgHisThrGlyValProSerArgPheSer

GlySerGlySerGlyThrAspPheThrPheThrIleSerSerLeuGln

ProGluAspIleAlaThrTyrTyrCysGlnGlnTyrSerLeuTyrArg

SerPheGlyGlnGlyThrLysValGluIleLysArgGlyGlyGlyGln

PheMetGluValGlnLeuValGluSerGlyGlyGlyValValGlnPro

GlyArgSerLeuArgLeuSerCysSerAlaSerGlyPheAspPheThr
```

ThrTyrTrpMetSerTrpValArgGlnAlaProGlyLysGlyLeuGlu
TrpIleGlyGluIleHisProAspSerSerThrIleAsnTyrAlaPro
SerLeuLysAspArgPheThrIleSerArgAspAsnAlaLysAsnThr
LeuPheLeuGlnMetAspSerLeuArgproGluAspThrGlyValTyr
PheCysAlaSerLeuTyrPheGlyPheProTrpPheAlaTyrTrpGly
GlnGlyThrProValThrValSerGlyGlyGlyGlySerAspIleVal
MetThrGlnSerProSerSerLeuAlaValSerProGlyGluArgVal
ThrLeuThrCysLysSerSerGlnSerLeuPheAsnSerArgThrArg
LysAsnTyrLeuGlyTrpTyrGlnGlnLysProGlyGlnSerProLys
LeuLeuIleTyrTrpAlaSerThrArgGluSerGlyValProAspArg
PheSerGlySerGlySerGlyThrAspPheThrLeuThrIleAsnSer
LeuGlnAlaGluAspValAlaValTyrTyrCysThrGlnValTyrTyr
LeuCysThrPheGlyAlaGlyThrLysLeuGluLeuLysArgLeuAsp
HisHisHisHisHisHis.

hBS14 Open Reading Frame 1 (Including Coding Sequence for the Leader Peptide) Nucleic Acid Sequence:

(SEQ ID NO: 13)
atgggatggagctgtatcatcctcttcttggtagcaacagctacaggtgt
ccactccatggaagtgcagctggtggagtcaggggggagacttagtgaagc
ctggagggtccctgaaactctcctgtgcagcctctggattcactttcagt
atttacaccatgtcttggcttcgccagactccggggaaggggctggagtg
ggtcgcaaccctgagtggtgatggtgatgacatctactatccagacagtg
tgaagggtcgattcaccatctccagagacaatgccaagaacagcctatat
ctgcagatgaacagtctaaggctgaggacacggccttgtattactgtgc
aagggtgcgacttggggactgggacttcgatgtctgggccaagggacca
cggtctccgtctcctcaggaggtggcggatccgacatccagctgacccag
agcccaagcagcctgagcgccagcgtgggcgacagagtgaccatcacctg
taaggccagtcaggatgtgggtacttctgtagcttggtaccagcagaagc
caggtaaggctccaaagctgctgatctactggacatccaccggcacact
ggtgtgccaagcagattcagcggtagcggtagcggtaccgacttcaccttc
accatcagcagcctccagccagaggacatcgccacctactactgccagc
aatatagcctctatcggtcgttcggccaagggaccaaggtggaaatcaaa
cgtctcgagggcggaggtagcgaggtccaactggtggagagcggtggagg
tgttgtgcaacctggccggtccctgcgcctgtcctgctccgcatctggct
tcgatttcaccacatattggatgagttgggtgagacaggcacctggaaaa
ggtcttgagtggattggagaaattcatccagatagcagtacgattaacta
tgcgccgtctctaaaggatagatttacaatatcgcgagacaacgccaaga
acacattgttcctgcaaatggacagcctgagacccgaagacaccggggtc
tattttttgtgcaagcctttacttcggcttcccctggtttgcttattgggg
ccaagggacccggtcaccgtctcagtcgaccatcatcatcatcatcatt
ga.

HBS14 Open Reading Frame 2 (Including Coding Sequence for the Leader Peptide) Nucleic Acid Sequence:

(SEQ ID NO: 14)
atgggatggagctgtatcatcctcttcttggtagcaacagctacaggtgt
ccactccatggacatccagctgacccagagcccaagcagcctgagcgcca
gcgtgggtgacagagtgaccatcacctgtaaggccagtcaggatgtgggt
acttctgtagcctggtaccagcagaagccaggtaaggctccaaagctgct
gatctactggacatccacccggcacactggtgtgccaagcagattcagcg
gtagcggtagcggtaccgacttcaccttcaccatcagcagcctccagcca
gaggacatcgccacctactactgccagcaatatagcctctatcggtcgtt
cggccaagggaccaaggtggaaatcaaacgtggaggtggccaattcatgg
aggtccaactggtggagagcggtggaggtgttgtgcaacctggccggtcc
ctgcgcctgtcctgctccgcatctggcttcgatttcaccacatattggat
gagttgggtgagacaggcacctggaaaaggtcttgagtggattggagaaa
ttcatccagatagcagtacgattaactatgcgccgtcgctaaaagataga
tttacaatatcgcgagacaacgccaagaacacattgttcctgcaaatgga
cagcctgagacccgaagacaccggggtctattttgtgcaagcctttact
tcggcttccctggtttgcttattggggccaagggaccccggtcaccgtc
tccggaggcggtggatccgacattgtgatgacacaatctccatcctccct
ggctgtgtcacccggggagagggtcactctgacctgcaaatccagtcaga
gtctgttcaacagtagaacccgaaagaactacttgggttggtaccagcag
aaaccagggcagtctcctaaacttctgatctactgggcatctactcggga
atctggggtccctgatcgcttctcaggcagtggatccggaacagatttca
ctctcaccatcaacagtctgcaggctgaagacgtggcagtttattactgc
actcaagtttattatctgtgcacgttcggtgctgggaccaagctggagct
gaaacggctcgaccatcatcatcatcatcattga.

Nucleic Acid Sequence of hBS14-pDHL2 Plasmid Construct:

(SEQ ID NO: 15)
ttccataggctccgccccctgacgagcatcacaaaaatcgacgctcaag
tcagaggtggcgaaacccgacaggactataaagataccaggcgtttcccc
ctggaagctccctcgtgcgctctcctgttccgaccctgccgcttaccgga
tacctgtccgcctttctcccttcgggaagcgtggcgctttctcatagctc
acgctgtaggtatctcagttcggtgtaggtcgttcgctccaagctgggct
gtgtgcacgaaccccccgttcagcccgaccgctgcgccttatccggtaac
tatcgtcttgagtccaacccggtaagacacgacttatcgccactggcagc
agccactggtaacaggattagcagagcgaggtatgtaggcggtgctacag
agttcttgaagtggtggcctaactacggctacactagaaggacagtattt
ggtatctgcgctctgctgaagccagttaccttcggaaaaagagttggtag
ctcttgatccggcaaacaaaccaccgctggtagcggtggtttttttgttt
gcaagcagcagattacgcgcagaaaaaaaggatctcaagaagatcctttg
atctttctacggggtctgacgctcagtggaacgaaaactcacgttaagg -continued

```
gattttggtcatgagattatcaaaaaggatcttcacctagatccttttaa
attaaaaatgaagttttaaatcaatctaaagtatatatgagtaaacttgg
tctgacagttaccaatgcttaatcagtgaggcacctatctcagcgatctg
tctatttcgttcatccatagttgcctgactccccgtcgtgtagataacta
cgatacgggagggcttaccatctggccccagtgctgcaatgataccgcga
gacccacgctcaccggctccagatttatcagcaataaaccagccagccgg
aagggccgagcgcagaagtggtcctgcaactttatccgcctccatccagt
ctattaattgttgccgggaagctagagtaagtagttcgccagttaatagt
ttgcgcaacgttgttgccattgctgcaggcatcgtggtgtcacgctcgtc
gtttggtatggcttcattcagctccggttcccaacgatcaaggcgagtta
catgatcccccatgttgtgcaaaaaagcggttagctccttcggtcctccg
atcgttgtcagaagtaagttggccgcagtgttatcactcatggttatggc
agcactgcataattctcttactgtcatgccatccgtaagatgcttttctg
tgactggtgagtactcaaccaagtcattctgagaatagtgtatgcggcga
ccgagttgctcttgcccggcgtcaacacgggataataccgcgccacatag
cagaactttaaaagtgctcatcattggaaaacgttcttcggggcgaaaac
tctcaaggatcttaccgctgttgagatccagttcgatgtaacccactcgt
gcacccaactgatcttcagcatcttttactttcaccagcgtttctgggtg
agcaaaaacaggaaggcaaaatgccgcaaaaaagggaataagggcgacac
ggaaatgttgaatactcatactcttcctttttcaatattattgaagcatt
tatcagggttattgtctcatgagcggatacatatttgaatgtatttagaa
aaataaacaaatagggtccgcgcacatttccccgaaaaggccacctga
cgtctaagaaaccattattatcatgacattaacctataaaaataggcgta
tcacgaggccctttcgtcttcaagaattccgatccagacatgataagata
cattgatgagtttggacaaaccacaactagaatgcagtgaaaaaaatgct
ttatttgtgaaatttgtgatgctattgctttatttgtaaccattataagc
tgcaataaacaagttaacaacaacaattgcattcattttatgtttcaggt
tcagggggaggtgtgggaggttttttaaagcaagtaaaacctctacaaat
gtggtatggctgattatgatctaaagccagcaaaagtcccatggtcttat
aaaaatgcatagctttaggaggggagcagagaacttgaaagcatcttcct
gttagtctttcttctcgtagacttcaaacttatacttgatgccttttcc
tcctggacctcagagaggacgcctgggtattctgggagaagtttatattt
ccccaaatcaatttctgggaaaaacgtgtcactttcaaattcctgcatga
tccttgtcacaaagagtctgaggtggcctggttgattcatggcttcctgg
taaacgaactgcctccgactatccaaaccatgtctactttacttgccaa
ttccggttgttcaataagtcttaaggcatcatccaaacttttggcaagaa
aatgagctcctcgtggtggttctttgagttctctactgagaactatatta
attctgtccttttaaaggtcgattcttctcaggaatggagaaccaggtttt
cctacccataatcaccagattctgtttaccttccactgaagaggttgtgg
tcattctttggaagtacttgaactcgttcctgagcggaggccagggtcgg
tctccgttcttgccaatccccatattttgggacacggcgacgatgcagtt
```

-continued

```
caatggtcgaaccatgagggcaccaagctagcttttgcaaaagcctagg
cctccaaaaaagcctcctcactacttctggaatagctcagaggccgaggc
ggcctcggcctctgcataaataaaaaaaattagtcagccatggggcggag
aatgggcggaactgggcggagttaggggcggatgggcggagttagggc
gggactatggttgctgactaattgagatgcatgctttgcatacttctgcc
tgctggggagcctggggacttccacacctggttgctgactaattgagat
gcatgctttgcatacttctgcctgctggggagcctggggacttccacac
cctaactgacacacattccacagtcgactagaatatggatagtgggtgtt
tatgactctggataagcctgaacaattgatgattaatgcccctgagctct
gttcttagtaacatgtgaacatttacttgtgtcagtgtagtagatttcac
atgacatcttataataaacctgtaaatgaaagtaatttgcattactagcc
cagcccagcccatactaagagttatattatgtctgtctcacagcctgctg
ctgaccaatattgaaaagaatagaccttcgactggcaggaagcaggtcat
gtggcaaggctatttggggaagggaaaataaaaccactaggtaaacttgt
agctgtggtttgaagaagtggttttgaaacactctgtccagccccaccaa
accgaaagtccaggctgagcaaaacaccacctgggtaatttgcatttcta
aaataagttgaggattcagccgaaactggagaggtcctcttttaacttat
tgagttcaaccttttaattttagcttgagtagttctagtttccccaaact
taagtttatcgacttctaaaatgtatttagaatttcgaccaattctcatg
tttgacagcttatcatcgctgcactccgcccgaaaagtgcgctcggctct
gccaaggacgcggggcgcgtgactatgcgtgggctggagcaaccgcctgc
tgggtgcaaacccttgcgcccggactcgtccaacgactataaagagggc
aggctgtcctctaagcgtcaccacgacttcaacgtcctgagtaccttctc
ctcacttactccgtagctccagcttcaccagatccctcgactctagacac
aggccgccaccatgggatggagctgtatcatcctcttcttggtagcaaca
gctacaggtgtccactccatggaagtgcagctggtggagtcaggggaga
cttagtgaagcctggagggtccctgaaactctcctgtgcagcctctggat
tcactttcagtatttacaccatgtcttggcttcgccagactccgggaaag
gggctggagtgggtcgcaacccctgagtggtgatggtgatgacatctacta
tccagacagtgtgaagggtcgattcaccatctccagagacaatgccaaga
acagcctatatctgcagatgaacagtctaagggctgaggacacggccttg
tattactgtgcaagggtgcgacttggggactgggacttcgatgtctgggg
ccaaggaccacggtctccgtctcctcaggaggtggcggatccgacatcc
agctgacccagagcccaagcagcctgagcgccagcgtgggtgacagagtg
accatcacctgtaaggccagtcaggatgtgggtacttctgtagcttggta
ccagcagaagccaggtaaggctccaaagctgctgatctactggacatcca
cccggcacactggtgtgccaagcagattcagcggtagcggtagcggtacc
gacttcaccttcaccatcagcagcctccagccagaggacatcgccaccta
ctactgccagcaatatagcctctatcggtcgttcggccaagggaccaagg
tggaaatcaaacgtctcgagggcggaggtagcgaggtccaactggtggag
```

-continued

```
agcggtggaggtgttgtgcaacctggccggtccctgcgcctgtcctgctc
cgcatctggcttcgatttcaccacatattggatgagttgggtgagacagg
cacctggaaaaggtcttgagtggattggagaaattcatccagatagcagt
acgattaactatgcgccgtctctaaaggatagatttacaatatcgcgaga
caacgccaagaacacattgttcctgcaaatggacagcctgagacccgaag
acaccggggtctattttttgtgcaagcctttacttcggcttcccctggttt
gcttattggggccaagggaccccggtcaccgtctcagtcgaccatcatca
tcatcatcattgataagatcccgcaattctaaactctgagggggtcggat
gacgtggccattctttgcctaaagcattgagtttactgcaaggtcagaaa
agcatgcaaagccctcagaatggctgcaaagagctccaacaaaacaattt
agaactttattaaggaatagggggaagctaggaagaaactcaaaacatca
agattttaaatacgcttcttggtctccttgctataattatctgggataag
catgctgttttctgtctgtcccaacatgccctgtgattatccgcaaaca
acacacccaagggcagaactttgttacttaaacaccatcctgtttgcttc
tttcctcaggaactgtggctgcaccatctgtcttcatcttcccgccatct
gatgagcagttgaaatctggaactgcctctgttgtgtgcctgctgaataa
cttctatcccagagaggccaaagtacagtggaaggtggataacgccctcc
aatcgggtaactcccaggagagtgtcacagagcaggacagcaaggacagc
acctacagcctcagcagcaccctgacgctgagcaaagcagactacgagaa
acacaaagtctacgcctgcgaagtcacccatcagggcctgagctcgcccg
tcacaaagagcttcaacaggggagagtgttagaggggagaagtgccccac
ctgctcctcagttccagcctgaccccctccatcctttggcctctgaccc
tttttccacaggggacctacccctattgcggtcctccagctcatctttca
cctcacccccctcctcctccttggctttaattatgctaatgttggaggag
aatgaataaataaagtgaatctttgcacctgtggtttctctcttttcctca
tttaataattattatctgttgttttaccaactactcaatttctcttataa
gggactaaatatgtagtcatcctaaggcgcataaccatttataaaaatca
tccttcattctatttaccctatcatcctctgcaagacagtcctccctca
aacccacaagccttctgtcctcacagtcccctgggccatggtaggagaga
cttgcttccttgttttcccctcctcagcaagccctcatagtccttttaa
gggtgacaggtcttacagtcatatatcctttgattcaattccctgagaat
caaccaaagcaaattttcaaaagaagaaacctgctataaagagaatcat
tcattgcaacatgatataaaataacaacacaataaaagcaattaaataaa
caaacaataggaaatgtttaagttcatcatggtacttagacttaatgga
atgtcatgccttatttacattttaaacaggtactgagggactcctgtct
gccaaggccgtattgagtactttccacaacctaatttaatccacactat
actgtgagattaaaaacattcattaaaatgttgcaaaggttctataaagc
tgagagacaaatatattctataactcagcaattcccacttctaggggttc
gactggcaggaagcaggtcatgtggcaaggctatttggggaagggaaaat
aaaaccactaggtaaacttgtagctgtggtttgaagaagtggttttgaaa
cactctgtccagccccaccaaaccgaaagtccaggctgagcaaaacacca
cctgggtaatttgcatttctaaaataagttgaggattcagccgaaactgg
agaggtcctcttttaacttattgagttcaacctttaatttagcttgag
tagttctagtttccccaaacttaagtttatcgacttctaaaatgtattta
gaatttcgaccaattctcatgtttgacagcttatcatcgctgcactccgc
ccgaaaagtgcgctcggctctgccaaggacgcggggcgcgtgactatgcg
tgggctggagcaaccgcctgctgggtgcaaacccttgcgcccggactcg
tccaacgactataaagagggcaggctgtcctctaagcgtcaccacgactt
caacgtcctgagtaccttctcctcacttactccgtagctccagcttcacc
agatccctcgagtctagacacaggccgccaccatgggatggagctgtatc
atcctcttcttggtagcaacagctacaggtgtccactccatggacatcca
gctgacccagagcccaagcagcctgagcgccagcgtgggtgacagagtga
ccatcacctgtaaggccagtcaggatgtgggtacttctgtagcttggtac
cagcagaagccaggtaaggctccaaagctgctgatctactggacatccac
ccggcacactggtgtgccaagcagattcagcggtagcggtagcggtaccg
acttcaccttcaccatcagcagcctccagccagaggacatcgccacctac
tactgccagcaatatagcctctatcggtcgttcggccaagggaccaaggt
ggaaatcaaacgtggaggtggccaattcatggaggtccaactggtggaga
gcggtggaggtgttgtgcaacctggccggtccctgcgcctgtcctgctcc
gcatctggcttcgatttcaccacatattggatgagttgggtgagacaggc
acctggaaaaggtcttgagtggattggagaaattcatccagatagcagta
cgattaactatgcgccgtctctaaaggatagatttacaatatcgcgagac
aacgccaagaacacattgttcctgcaaatggacagcctgagacccgaaga
caccggggtctattttttgtgcaagcctttacttcggcttcccctggtttg
cttattggggccaagggaccccggtcaccgtctccggaggcggtggatcc
gacattgtgatgacacaatctccatcctccctggctgtgtcacccgggga
gagggtcactctgacctgcaaatccagtcagagtctgttcaacagtagaa
cccgaaagaactacttgggttggtaccagcagaaaccagggcagtctcct
aaacttctgatctactgggcatctactcgggaatctggggtccctgatcg
cttctcaggcagtggatccggaacagatttcactctcaccatcaacagtc
tgcaggctgaagacgtggcagtttattactgcactcaagtttattatctg
tgcacgttcggtgctgggaccaagctggagctgaaacggctcgaccatca
tcatcatcattgataagatctcggccggcaagcccccgctccccggg
ctctcgcggtcgcacgaggatgcttggcacgtacccccgtctacatacttc
ccaggcacccagcatggaaataaagcacccaccactgccctgggcccctg
cgagactgtgatggttctttccacgggtcaggccgagtctgaggcctgag
tggcatgagggaggcagagcgggtcccactgtccccacactggcccaggc
tgtgcaggtgtgcctgggccgcctagggtggggctcagccaggggctgcc
ctcggcagggtgggggatttgccagcgtggccctccctccagcagcagct
gcctcgcgcgtttcggtgatgacggtgaaaacctctgacacatgcagctc
ccggagacggtcacagcttgtctgtaagcggatgccgggagcagacaagc
```

-continued

```
ccgtcagggcgcgtcagcgggtgttggcgggtgtcggggcgcagccatga cccagtcacgtagcgatagcggagtgtatactggcttaactatgcggcat cagagcagattgtactgagagtgcaccatatgcggtgtgaaataccgcac agatgcgtaaggagaaaataccgcatcaggcgctcttccgcttcctcgct cactgactcgctgcgctcggtcgttcggctgcggcgagcggtatcagctc actcaaaggcggtaatacggttatccacagaatcaggggataacgcagga aagaacatgtgagcaaaaggccagcaaaaggccaggaaccgtaaaaaggc cgcgttgctggcgttt
```

Example 3

Affinity Purification of hBS14 hBS14 was purified to homogeneity using a novel affinity resin that was prepared and used as described below.

Activation and Coupling of IMP291-Affigel

IMP291 peptide (see structure in FIG. 18) was coupled to Affigel 102 (BIO-RAD Laboratories, Hercules Calif.) using chloroacetic anhydride (CAA). CCA (1.5 g, 8.8 mmol) was dissolved in acetonitrile and added to 30 ml of Affigel 102 slurry. The pH was adjusted to 9.0 with triethylamine and reacted for 1 hour at room temperature to allow coupling of CAA to amine groups on the Affigel. The CAA-Affigel was washed and exchanged into 0.2M NaBorate, pH 8.0. A total of 166 mg of IMP291 was dissolved in 10 ml of 0.2M NaBorate, pH 8.0 and then added to the slurry, which was then rocked overnight at room temperature to allow coupling of the peptide to the CAA-Affigel via thioether bond formation. The resin was quenched by adding cysteine in 0.2M NaBorate, pH 8.0 to a final concentration of 20 mM and incubated for 1 hour at room temperature.

Qualification of the Affinity Resin

The IMP291-affigel resin was qualified as follows: A column was packed with 0.5 ml of the resin and equilibrated with PBS. A total of 23.5 mg of BS1.5HP in 10 ml of PBS was passed over the column. A total of 14 mg of BS1.5HP was detected in the unbound fraction indicating 9.5 mg had bound. A total of 9.2 mg was recovered in 7 ml of elution with 1 M Imidazole, 150 mM sucrose, 10 mM NaAc, pH 4.5. The binding capacity of the resin was determined to be 330 pmol/ml. For hBS14, this is equivalent to a capacity of 26.7 mg/ml.

Single-Step Purification of hBS14 with IMP291-Affigel

A total of 22 liters of hBS14 YB2/0 clone #8 roller bottle culture containing 144 mg of hBS14 (as estimated by BIAcore) was centrifuged and brought to 2 mM EDTA, 0.02% Triton-X-100; and 10 mM $Na_2HPO_4$. The supernatant fluid was sterile-filtered through a 0.2 μM Millipak-200 filter unit into an autoclaved 10-L bottle closed system. The filtered media was loaded over a 10 ml IMP291-affigel column (2.5 cm diameter) at flow rates ranging from 2 to 4 ml/min. The column was washed to baseline with PBS and then eluted with 107 ml of elution buffer (1M imidazole, 150 mM sucrose, 50 mM citrate, pH 4.5). A total of 93 mg of hBS14 was eluted. Size exclusion HPLC, SDS-PAGE, IEF, and MALDI-TOF mass spectrometry all indicated a highly purified homogeneous product from the single step IMP291-affigel affinity chromatography. BIAcore and in vivo analysis demonstrated that the product was fully active.

Example 4

Use of hBS14 for Pre-Targeting of Human Colorectal Tumor Xenografts in Nude Mice This example demonstrates the ability of the trivalent, bispecific hBS 14 molecule (hMN-14×hMN-14×679) to pre-target IMP-245, a $^{99m}$Tc-labeled peptide, to a human colonic tumor (GW-39) xenograft. The structure of IMP 245 is shown in FIG. 19. IMP-245 was prepared and labeled using standard techniques known in the art. See, for example, published application US20030198595 (now issued U.S. Pat. No. 7,138,103), which is hereby incorporated by reference in its entirety.

The experiment used 3 groups of 15 mice, each of which was necropsied, and 1 group of 5 mice that was imaged. Three groups of mice were administered 6 μCi $^{125}$I-hBS14 (40 μg, $5.0 \times 10^{-10}$ moles). In the last group (imaging group), 3 mice received unlabeled hBS14. The amount of $^{99m}$Tc-IMP-245 administered to all the mice was ~40 μCi (92 ng, $5.0 \times 10^{-11}$ moles) for a bispecific:peptide ratio of 10:1. Mice were necropsied at 1, 4, and 24 hours post-peptide administration, and were divided into the following groups:

Group I: $^{125}$I-hBS14 with 4-hr clearance followed by $^{99m}$Tc-IMP-245 [15 mice; sac 5/time-point at 1-, 4-, and 24-hrs post-DCS injection]

Group II: $^{125}$I-hBS14 with 24-hr clearance followed by $^{99m}$Tc-IMP-245 [15 mice; sac 5/time-point at 1-, 4-, and 24-hrs post-DCS injection]

Group III: $^{125}$-I-hBS14 with 48-hr clearance followed by $^{99m}$Tc-IMP-245 [15 mice; sac 5/time-point at 1-, 4-, and 24-hrs post-DCS injection]

Group IV: hBS14 with 48-hr clearance (3 mice) followed by $^{99m}$Tc-IMP-245 (all 5 mice) [5 mice; image mice at 1-, 3-, 6-, and 24-hrs post-DCS injection]

Due to differences in tumor growth rates, only 20 mice were initially available for administration of hBS14. Fifteen mice were used to fill out Group II while 5 mice were used for Group I. The remaining mice (including the imaged mice) were injected one week later. Not all the mice implanted with GW-39 tumors developed usable tumors and, therefore, Group I only had 10 mice and were sacrificed at 1 hr post-peptide injection and 24 hrs post-injection.

The graph in FIG. 20 (top panel) shows the tumor uptake of the $^{125}$I-hBS14 and $^{99m}$Tc-IMP-245 in mice when the hBS14 was given 4 hrs to clear prior to administration of peptide (Group I). At 1 hr post-peptide administration there was 13.5±5.94% ID/g hBS14 in the tumor versus 2.9±0.46% ID/g of IMP-245 (4.7-fold less peptide than hBS14). After 24 hrs this ratio reversed with 2.4-fold more IMP-245 in the tumor versus the hBS14 (9.08±4.94% ID/g vs. 3.79±4.15% ID/g, respectively). Blood levels for the hBS14 and peptide were high at 1 hr post-injection (16.85±2.95% ID/g and 36.87±6.42% ID/g for hBS14 and IMP-245, respectively).

Data for the mice in Group II are shown in FIG. 20 (bottom panel) Approximately 2-fold more IMP-245 than hBS14 was observed in the tumors. The greatest amount of variation occurred in the 4 hr post-IMP245 administration group (15.9±16.3% ID/g IMP-245 in the tumor). These differences do not appear to be due to hBS14 uptake since one mouse had 4.6% ID/g hBS14 in its tumor and only 3.6% ID/g IMP-245 while another mouse in this group also had 4.4% ID/g hBS14 but 18.1% ID/g IMP-245. There appears, however, to be a correlation between tumor size. These data suggest that larger tumors have better targeting in mice.

The graph in FIG. 21 (top panel) shows the tumor uptake of $^{125}$I-hBS14 and $^{99m}$Tc-IMP-245 in mice given 48 hrs to clear the hBS14 prior the administration of the peptide (Group III). Like the Group II mice (24 hr hBS14 clearance), consistent targeting of the hBS14 to the tumor at all three time-points was observed. At 1 hr post-peptide injection (49 hrs post-hBS14 administration) there was 3.50±0.86% ID/g hBS14 in the tumor. This level was maintained throughout two later time-points (52 hrs and 72 hrs post-hBS14 administration) at 3.62±1.59% ID/g and 6.97±3.10% ID/g, respectively. These data suggest that the bivalent hMN-14 portion of the hBS14 molecule increased its ability to stay on the tumor without being shed or otherwise lost. This stabilized binding of hBS14 to the tumor also resulted in a relatively constant $^{99m}$Tc-IMP-245 signal at the tumor. At 1 hr post-peptide injection there was 21.03±2.47% ID/g at the tumor. After 4 hrs there was 14.53±4.90% ID/g and 15.47±9.31% ID/g at 24 hrs post-injection. The differences between any of these three time-points are not significant but, since $^{99m}$Tc has such a short half-life (6.02 hrs) the relative amount of actual signal in the tumors at 24 hrs was 13-fold less.

The table shown in FIG. 22 summarizes the % ID/g of the $^{99m}$Tc-IMP-245 and the tumor to non-tumor ratios (T:NT) in the various tissues at 1 hr post-peptide administration for all three groups of mice (4, 24, and 48 hr hBS14 clearance). One hour post-peptide injection was used since early time-points for imaging are clinically desirable.

The data from the imaged mice are shown in FIG. 23. The first pair of images shows the location of the tumors in the mice. hBS14 (5×10$^{-11}$ moles) was administered, followed after 48 hours by $^{99m}$Tc-IMP-245 (40 µCi; 5×10$^{-11}$ moles). Animals 1 & 2 were given peptide only, while animals 3, 4, & 5 were administered hBS14 followed by peptide. The animals had the following tumor sizes:

Animal 1: 1.68 cm$^3$ tumor
Animal 2: 0.62 cm$^3$ tumor
Animal 3: 1.22 cm$^3$ tumor
Animal 4: 0.62 cm$^3$ tumor
Animal 5: 0.56 cm$^3$ tumor The second pair of images shows the image at 1 hr post-peptide administration. After only 1 hour the tumors in the mice pre-targeted with the hBS14 were clearly visible. The majority of the signal was located in the bladder at this early time-point, as expected, and the kidneys also were evident in the images. External radioactivity was found on the foot of Animal 4 (circled) and was removed by washing the foot.

The third pair of images show imaging data at 3 hrs post-peptide administration. At the 3 hr time-point, Animal 3 was removed. This mouse had very high tumor uptake and adjusting the image for this mouse decreased the sensitivity in the remaining four mice. The outline of the tumors was visible in the mice that received only peptide, but this was due to the blood pool and not direct targeting as can be seen with Animals 4 & 5. The mice were still under the effects of the anesthesia from the first time-point and were unable to void their bladders, resulting in the high signal observed in the bladded.

The final pair of images shows the image at 24 hrs post-peptide administration. Little signal remained in the mice at this time-point, which therefore were imaged for 20 minutes rather than the 10 minutes used at earlier time-points. The only signal detected was located in the tumors of the mice pre-targeted with hBS14 prior to the administration of the $^{99m}$Tc-IMP-245.

All three pre-targeted mice and both mice that received peptide alone were necropsied after the 24-hr imaging and the results are shown in FIG. 21 (bottom panel). Tumor and kidney uptake was the highest in the pre-targeted mice (19.01±2.80% ID/g and 3.81±0.80% ID/g, respectively). There was very little peptide in the tumor of the control mice (0.30±0.08% ID/g), but the same amount in the kidney as the pre-targeted mice (3.71±0.43% ID/g).

What is claimed is:

1. An episome comprising:
(a) a first promoter operationally connected to a first nucleic acid encoding a first polypeptide comprising a polypeptide chain represented by the formula α-factor-$a_1$-$l_1$-$a_2$-$l_2$-$a_3$, wherein $a_1$, $a_2$, and $a_3$ are immunoglobulin variable domains and $l_1$ and $l_2$ are peptide linkers, and wherein the first polypeptide comprises the amino acid sequence of h679VH (residues 8 to 126 of SEQ ID NO:1),
(b) a second promoter operationally connected to a second nucleic acid encoding a polypeptide comprising a second polypeptide chain represented by the formula α-factor-$b_1$-$l_3$-$b_2$-$l_4$-$b_3$, wherein $b_1$, $b_2$ and $b_3$ are immunoglobulin variable domains and $l_3$ and $l_4$ are peptide linkers and the second polypeptide comprises the amino acid sequence of h679VK (residues 243 to 357 of SEQ ID NO:2),
wherein said first and second polypeptide bind together form a complex comprising at least three antigen binding sites,
wherein each of said antigen binding sites comprises a variable domain from said first polypeptide chain and a variable domain from said second polypeptide chain,
wherein each of said polypeptides does not bind to itself to form an antigen binding site,
wherein said first nucleic acid and said second nucleic acid are coexpressed when the episome is transformed into a host cell.

2. The episome of claim 1 which is a plasmid.

3. A host cell comprising an episome according to claim 2.

4. A method of preparing a polyvalent protein complex, comprising culturing a host cell according to claim 3 in culture medium, wherein the α-factor results in secretion of the first and second polypeptides into the culture medium.

5. The host cell of claim 3, wherein said cell is a murine myeloma cell line.

6. The method according to claim 4, wherein at least one polypeptide chain further comprises an amino acid sequence selected from the group consisting of a toxin, a cytokine, a lymphokine, a enzyme, growth factor, and an affinity purification tag.

7. The episome according to claim 1, wherein two of the antigen binding sites bind to CEA (carcinoembryonic antigen) and one of the antigen binding sites binds to HSG (histamine succinyl glycyl).

8. The episome according to claim 1, wherein two of the antigen binding sites bind to tumor-associated antigens.

9. The episome according to claim 1, wherein the first polypeptide comprises the amino acid sequence of SEQ ID NO:1 and the second polypeptide comprises the amino acid sequence of SEQ ID NO:2.

10. The episome according to claim 1, wherein the first polypeptide comprises the amino acid sequence of SEQ ID NO:11 and the second polypeptide comprises the amino acid sequence of SEQ ID NO:12.

11. An episome comprising:
(a) a first promoter operationally connected to a first nucleic acid encoding a first polypeptide comprising a polypeptide chain represented by the formula α-factor-$a_1$-$l_1$-$a_2$-$l_2$-$a_3$, wherein $a_1$ is a heavy chain variable domain from a first antibody, $a_2$ is a light chain variable domain from a second antibody, and $a_3$ is a heavy chain variable domain from a third antibody and $l_1$ and $l_2$ are peptide linkers, and wherein the first polypeptide comprises the amino acid sequence of h679VH (residues 8 to 126 of SEQ ID NO:1),
(b) a second promoter operationally connected to a second nucleic acid encoding a polypeptide comprising a second polypeptide chain represented by the formula α-factor-$b_1$-$l_3$-$b_2$-$l_4$-$b_3$, wherein $b_1$ is a light chain variable domain from the first antibody, $b_2$ is a heavy chain variable domain from the second antibody and $b_3$ is a light chain variable domain from the third antibody and $l_3$ and $l_4$ are peptide linkers and the second polypeptide comprises the amino acid sequence of h679VK (residues 243 to 357 of SEQ ID NO:2),
wherein said first and second polypeptide bind together form a complex comprising at least three antigen binding sites,
wherein each of said antigen binding sites comprises a variable domain from said first polypeptide chain and a variable domain from said second polypeptide chain,
wherein each of said polypeptides does not bind to itself to form an antigen binding site,
wherein said first nucleic acid and said second nucleic acid are coexpressed when the episome is transformed into a host cell.

12. The episome of claim 11, wherein two of the antigen binding sites have the same binding specificity and the third antigen binding site has a different specificity.

13. The episome of claim 11, wherein two of the antigen binding sites bind to tumor-associated antigens.

14. The episome of claim 11, wherein the first polypeptide comprises the amino acid sequence of SEQ ID NO:1 and the second polypeptide comprises the amino acid sequence of SEQ ID NO:2.

15. The episome of claim 11, wherein the first nucleic acid comprises the sequence of SEQ ID NO:13 and the second nucleic acid comprises the sequence of SEQ ID NO:14.

16. The episome of claim 11, wherein the first polypeptide comprises the amino acid sequence of SEQ ID NO:11 and the second polypeptide comprises the amino acid sequence of SEQ ID NO:12.

17. The episome of claim 11, wherein at least one polypeptide chain further comprises an amino acid sequence selected from the group consisting of a toxin, a cytokine, a lymphokine, a enzyme, growth factor, and an affinity purification tag.

18. The episome of claim 13, wherein the TAA is CEA.

19. The episome of claim 18, wherein administration of the complex and the targetable construct to a subject with a tumor provides three-fold more binding of the construct to the tumor, compared with a bispecific anti-CEA×anti-HSG antibody.

* * * * *

SEQUENCE LISTING

```
<160> NUMBER OF SEQ ID NOS: 20

<210> SEQ ID NO 1
<211> LENGTH: 370
<212> TYPE: PRT
<213> ORGANISM: Artificial Sequence
<220> FEATURE:
<223> OTHER INFORMATION: Description of Artificial Sequence: Synthetic
      chimeric sequence from multiple species

<400> SEQUENCE: 1

Glu Ala Glu Ala Glu Phe Met Glu Val Gln Leu Val Glu Ser Gly Gly
1               5                   10                  15

Asp Leu Val Lys Pro Gly Gly Ser Leu Lys Leu Ser Cys Ala Ala Ser
            20                  25                  30

Gly Phe Thr Phe Ser Ile Tyr Thr Met Ser Trp Leu Arg Gln Thr Pro
        35                  40                  45

Gly Lys Gly Leu Glu Trp Val Ala Thr Leu Ser Gly Asp Gly Asp Asp
    50                  55                  60

Ile Tyr Tyr Pro Asp Ser Val Lys Gly Arg Phe Thr Ile Ser Arg Asp
65                  70                  75                  80

Asn Ala Lys Asn Ser Leu Tyr Leu Gln Met Asn Ser Leu Arg Ala Glu
                85                  90                  95
```

Asp Thr Ala Leu Tyr Tyr Cys Ala Arg Val Arg Leu Gly Asp Trp Asp
            100                 105                 110

Phe Asp Val Trp Gly Gln Gly Thr Val Ser Val Ser Ser Gly Gly
            115                 120                 125

Gly Gly Ser Asp Ile Gln Leu Thr Gln Ser Pro Ser Ser Leu Ser Ala
130                 135                 140

Ser Val Gly Asp Arg Val Thr Ile Thr Cys Lys Ala Ser Gln Asp Val
145                 150                 155                 160

Gly Thr Ser Val Ala Trp Tyr Gln Gln Lys Pro Gly Lys Ala Pro Lys
                165                 170                 175

Leu Leu Ile Tyr Trp Thr Ser Thr Arg His Thr Gly Val Pro Ser Arg
            180                 185                 190

Phe Ser Gly Ser Gly Ser Gly Thr Asp Phe Thr Phe Thr Ile Ser Ser
            195                 200                 205

Leu Gln Pro Glu Asp Ile Ala Thr Tyr Tyr Cys Gln Gln Tyr Ser Leu
    210                 215                 220

Tyr Arg Ser Phe Gly Gln Gly Thr Lys Val Glu Ile Lys Arg Leu Glu
225                 230                 235                 240

Gly Gly Gly Ser Glu Val Gln Leu Val Glu Ser Gly Gly Gly Val Val
                245                 250                 255

Gln Pro Gly Arg Ser Leu Arg Leu Ser Cys Ser Ala Ser Gly Phe Asp
            260                 265                 270

Phe Thr Thr Tyr Trp Met Ser Trp Val Arg Gln Ala Pro Gly Lys Gly
            275                 280                 285

Leu Glu Trp Ile Gly Glu Ile His Pro Asp Ser Ser Thr Ile Asn Tyr
            290                 295                 300

Ala Pro Ser Leu Lys Asp Arg Phe Thr Ile Ser Arg Asp Asn Ala Lys
305                 310                 315                 320

Asn Thr Leu Phe Leu Gln Met Asp Ser Leu Arg Pro Glu Asp Thr Gly
            325                 330                 335

Val Tyr Phe Cys Ala Ser Leu Tyr Phe Gly Phe Pro Trp Phe Ala Tyr
            340                 345                 350

Trp Gly Gln Gly Thr Pro Val Thr Val Ser Val Asp His His His
            355                 360                 365

His His
    370

<210> SEQ ID NO 2
<211> LENGTH: 363
<212> TYPE: PRT
<213> ORGANISM: Artificial Sequence
<220> FEATURE:
<223> OTHER INFORMATION: Description of Artificial Sequence: Synthetic
      chimeric sequence from multiple species

<400> SEQUENCE: 2

Glu Ala Glu Ala Glu Phe Asp Ile Gln Leu Thr Gln Ser Pro Ser Ser
1               5                   10                  15

Leu Ser Ala Ser Val Gly Asp Arg Val Thr Ile Thr Cys Lys Ala Ser
            20                  25                  30

Gln Asp Val Gly Thr Ser Val Ala Trp Tyr Gln Gln Lys Pro Gly Lys
        35                  40                  45

Ala Pro Lys Leu Leu Ile Tyr Trp Thr Ser Thr Arg His Thr Gly Val
    50                  55                  60

Pro Ser Arg Phe Ser Gly Ser Gly Ser Gly Thr Asp Phe Thr Phe Thr

```
                65                  70                  75                  80
        Ile Ser Ser Leu Gln Pro Glu Asp Ile Ala Thr Tyr Tyr Cys Gln Gln
                        85                  90                  95

Tyr Ser Leu Tyr Arg Ser Phe Gly Gln Gly Thr Lys Val Glu Ile Lys
                        100                 105                 110

Arg Gly Gly Gly Gln Phe Met Glu Val Gln Leu Val Glu Ser Gly Gly
                        115                 120                 125

Gly Val Val Gln Pro Gly Arg Ser Leu Arg Leu Ser Cys Ser Ala Ser
                130                 135                 140

Gly Phe Asp Phe Thr Thr Tyr Trp Met Ser Trp Val Arg Gln Ala Pro
        145                 150                 155                 160

Gly Lys Gly Leu Glu Trp Ile Gly Glu Ile His Pro Asp Ser Ser Thr
                        165                 170                 175

Ile Asn Tyr Ala Pro Ser Leu Lys Asp Arg Phe Thr Ile Ser Arg Asp
                        180                 185                 190

Asn Ala Lys Asn Thr Leu Phe Leu Gln Met Asp Ser Leu Arg Pro Glu
                        195                 200                 205

Asp Thr Gly Val Tyr Phe Cys Ala Ser Leu Tyr Phe Gly Phe Pro Trp
                210                 215                 220

Phe Ala Tyr Trp Gly Gln Gly Thr Pro Val Thr Val Ser Gly Gly Gly
        225                 230                 235                 240

Gly Ser Asp Ile Val Met Thr Gln Ser Pro Ser Ser Leu Ala Val Ser
                        245                 250                 255

Pro Gly Glu Arg Val Thr Leu Thr Cys Lys Ser Ser Gln Ser Leu Phe
                        260                 265                 270

Asn Ser Arg Thr Arg Lys Asn Tyr Leu Gly Trp Tyr Gln Gln Lys Pro
                        275                 280                 285

Gly Gln Ser Pro Lys Leu Leu Ile Tyr Trp Ala Ser Thr Arg Glu Ser
                290                 295                 300

Gly Val Pro Asp Arg Phe Ser Gly Ser Gly Ser Gly Thr Asp Phe Thr
        305                 310                 315                 320

Leu Thr Ile Asn Ser Leu Gln Ala Glu Asp Val Ala Val Tyr Tyr Cys
                        325                 330                 335

Thr Gln Val Tyr Tyr Leu Cys Thr Phe Gly Ala Gly Thr Lys Leu Glu
                        340                 345                 350

Leu Lys Arg Leu Asp His His His His His His
                        355                 360

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatcccctgc agggagctca ctagta                                            26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
```

```
gatctactag tgagctccct gcaggg                                          26
```

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
catactcgag ggcggaggta gcgaggtcca actggtggag agc                       43
```

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
cttagtcgac ggagacggtg accggggtc                                       29
```

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ctaggaattc gacatccagc tgacccagag                                      30
```

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
cgtacaattg gccacctcca cgtttgattt ccaccttgg                            39
```

<210> SEQ ID NO 9
<211> LENGTH: 1110
<212> TYPE: DNA
<213> ORGANISM: Artificial Sequence
<220> FEATURE:
<223> OTHER INFORMATION: Description of Artificial Sequence: Synthetic
      chimeric sequence from multiple species

<400> SEQUENCE: 9

```
gaggctgaag ctgaattcat ggaagtgcag ctggtggagt cagggggaga cttagtgaag      60
cctggagggt ccctgaaact ctcctgtgca gcctctggat tcactttcag tatttacacc     120
atgtcttggc ttcgccagac tccgggaaag gggctgagtg ggtcgcaac cctgagtggt      180 gatggtgatg acatctacta tccagacagt gtgaagggtc gattcaccat ctccagagac     240
aatgccaaga acagcctata tctgcagatg aacagtctaa gggctgagga cacggccttg     300
tattactgtg caagggtgcg acttggggac tgggacttcg atgtctgggg ccaagggacc     360
acggtctccg tctcctcagg aggtggcgga tccgacatcc agctgaccca gagcccaagc     420
```

```
agcctgagcg ccagcgtggg tgacagagtg accatcacct gtaaggccag tcaggatgtg    480
ggtacttctg tagcttggta ccagcagaag ccaggtaagg ctccaaagct gctgatctac    540
tggacatcca cccggcacac tggtgtgcca agcagattca gcggtagcgg tagcggtacc    600 gacttcaccct tcaccatcag cagcctccag ccagaggaca tcgccaccta ctactgccag    660
caatatagcc tctatcggtc gttcggccaa gggaccaagg tggaaatcaa acgtctcgag    720
ggcggaggta gcgaggtcca actggtggag agcgtggga gtgttgtgca acctggccgg    780
tccctgcgcc tgtcctgctc cgcatctggc ttcgatttca ccacatattg gatgagttgg    840
gtgagacagg cacctggaaa aggtcttgag tggattggag aaattcatcc agatagcagt    900
acgattaact atgcgccgtc tctaaaggat agatttacaa tatcgcgaga caacgccaag    960
aacacattgt tcctgcaaat ggacagcctg agacccgaag acaccggggt ctattttgt    1020 gcaagccttt acttcggctt cccctggttt gcttattggg gccaagggac cccggtcacc    1080
gtctccgtcg accatcatca tcatcatcat                                    1110

<210> SEQ ID NO 10
<211> LENGTH: 1089
<212> TYPE: DNA
<213> ORGANISM: Artificial Sequence
<220> FEATURE:
<223> OTHER INFORMATION: Description of Artificial Sequence: Synthetic
      chimeric sequence from multiple species

<400> SEQUENCE: 10
gaggctgaag ctgaattcga catccagctg acccagagcc caagcagcct gagcgccagc     60
gtgggtgaca gagtgaccat cacctgtaag gccagtcagg atgtgggtac ttctgtagct    120
tggtaccagc agaagccagg taaggctcca aagctgctga tctactggac atccacccgg    180
cacactggtg tgccaagcag attcagcggt agcggtagcg gtaccgactt caccttcacc    240
atcagcagcc tccagccaga ggacatcgcc acctactact gccagcaata tagcctctat    300
cggtcgttcg gccaagggac caaggtggaa atcaaacgtg aggtggcca attcatggag    360 gtccaactgg tggagagcgg tggaggtgtt gtgcaacctg gccggtccct gcgcctgtcc    420
tgctccgcat ctggcttcga tttcaccaca tattggatga gttgggtgag acaggcacct    480
ggaaaaggtc ttgagtggat tggagaaatt catccagata gcagtacgat taactatgcg    540
ccgtctctaa aggatagatt tacaatatcg cgagacaacg ccaagaacac attgttcctg    600
caaatggaca gcctgagacc cgaagacacc ggggtctatt tttgtgcaag cctttacttc    660
ggcttcccct ggtttgctta ttggggccaa gggaccccgg tcaccgtctc cggaggcggt    720
ggatccgaca ttgtgatgac acaatctcca tcctccctgg ctgtgtcacc cggggagagg    780
gtcactctga cctgcaaatc cagtcagagt ctgttcaaca gtagaacccg aaagaactac    840
ttgggttggt accagcagaa accagggcag tctcctaaac ttctgatcta ctgggcatct    900
actcgggaat ctggggtccc tgatcgcttc tcaggcagtg gatccggaac agatttcact    960
ctcaccatca acagtctgca ggctgaagac gtggcagttt attactgcac tcaagtttat   1020
tatctgtgca cgttcggtgc tgggaccaag ctggagctga acggctcga ccatcatcat   1080 catcatcat                                                          1089

<210> SEQ ID NO 11
<211> LENGTH: 364
<212> TYPE: PRT
<213> ORGANISM: Artificial Sequence
```

<220> FEATURE:
<223> OTHER INFORMATION: Description of Artificial Sequence: Synthetic chimeric sequence from multiple species

<400> SEQUENCE: 11

```
Met Glu Val Gln Leu Val Glu Ser Gly Gly Asp Leu Val Lys Pro Gly
1               5                   10                  15
Gly Ser Leu Lys Leu Ser Cys Ala Ala Ser Gly Phe Thr Phe Ser Ile
            20                  25                  30
Tyr Thr Met Ser Trp Leu Arg Gln Thr Pro Gly Lys Gly Leu Glu Trp
        35                  40                  45
Val Ala Thr Leu Ser Gly Asp Gly Asp Asp Ile Tyr Tyr Pro Asp Ser
50                  55                  60
Val Lys Gly Arg Phe Thr Ile Ser Arg Asp Asn Ala Lys Asn Ser Leu
65                  70                  75                  80
Tyr Leu Gln Met Asn Ser Leu Arg Ala Glu Asp Thr Ala Leu Tyr Tyr
                85                  90                  95
Cys Ala Arg Val Arg Leu Gly Asp Trp Asp Phe Asp Val Trp Gly Gln
            100                 105                 110
Gly Thr Thr Val Ser Val Ser Ser Gly Gly Gly Gly Ser Asp Ile Gln
        115                 120                 125
Leu Thr Gln Ser Pro Ser Ser Leu Ser Ala Ser Val Gly Asp Arg Val
130                 135                 140
Thr Ile Thr Cys Lys Ala Ser Gln Asp Val Gly Thr Ser Val Ala Trp
145                 150                 155                 160
Tyr Gln Gln Lys Pro Gly Lys Ala Pro Lys Leu Leu Ile Tyr Trp Thr
                165                 170                 175
Ser Thr Arg His Thr Gly Val Pro Ser Arg Phe Ser Gly Ser Gly Ser
            180                 185                 190
Gly Thr Asp Phe Thr Phe Thr Ile Ser Ser Leu Gln Pro Glu Asp Ile
        195                 200                 205
Ala Thr Tyr Tyr Cys Gln Gln Tyr Ser Leu Tyr Arg Ser Phe Gly Gln
210                 215                 220
Gly Thr Lys Val Glu Ile Lys Arg Leu Glu Gly Gly Gly Ser Glu Val
225                 230                 235                 240
Gln Leu Val Glu Ser Gly Gly Val Val Gln Pro Gly Arg Ser Leu
                245                 250                 255
Arg Leu Ser Cys Ser Ala Ser Gly Phe Asp Phe Thr Thr Tyr Trp Met
            260                 265                 270
Ser Trp Val Arg Gln Ala Pro Gly Lys Gly Leu Glu Trp Ile Gly Glu
        275                 280                 285
Ile His Pro Asp Ser Ser Thr Ile Asn Tyr Ala Pro Ser Leu Lys Asp
290                 295                 300
Arg Phe Thr Ile Ser Arg Asp Asn Ala Lys Asn Thr Leu Phe Leu Gln
305                 310                 315                 320
Met Asp Ser Leu Arg Pro Glu Asp Thr Gly Val Tyr Phe Cys Ala Ser
                325                 330                 335
Leu Tyr Phe Gly Phe Pro Trp Phe Ala Tyr Trp Gly Gln Gly Thr Pro
            340                 345                 350
Val Thr Val Ser Val Asp His His His His His
        355                 360
```

<210> SEQ ID NO 12
<211> LENGTH: 358
<212> TYPE: PRT

<213> ORGANISM: Artificial Sequence
<220> FEATURE:
<223> OTHER INFORMATION: Description of Artificial Sequence: Synthetic chimeric sequence from multiple species

<400> SEQUENCE: 12

```
Met Asp Ile Gln Leu Thr Gln Ser Pro Ser Ser Leu Ser Ala Ser Val
1               5                   10                  15

Gly Asp Arg Val Thr Ile Thr Cys Lys Ala Ser Gln Asp Val Gly Thr
            20                  25                  30

Ser Val Ala Trp Tyr Gln Gln Lys Pro Gly Lys Ala Pro Lys Leu Leu
        35                  40                  45

Ile Tyr Trp Thr Ser Thr Arg His Thr Gly Val Pro Ser Arg Phe Ser
50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Tyr Ser Leu Tyr Arg
                85                  90                  95

Ser Phe Gly Gln Gly Thr Lys Val Glu Ile Lys Arg Gly Gly Gly Gln
            100                 105                 110

Phe Met Glu Val Gln Leu Val Glu Ser Gly Gly Val Val Gln Pro
        115                 120                 125

Gly Arg Ser Leu Arg Leu Ser Cys Ser Ala Ser Gly Phe Asp Phe Thr
130                 135                 140

Thr Tyr Trp Met Ser Trp Val Arg Gln Ala Pro Gly Lys Gly Leu Glu
145                 150                 155                 160

Trp Ile Gly Glu Ile His Pro Asp Ser Ser Thr Ile Asn Tyr Ala Pro
                165                 170                 175

Ser Leu Lys Asp Arg Phe Thr Ile Ser Arg Asp Asn Ala Lys Asn Thr
            180                 185                 190

Leu Phe Leu Gln Met Asp Ser Leu Arg Pro Glu Asp Thr Gly Val Tyr
        195                 200                 205

Phe Cys Ala Ser Leu Tyr Phe Gly Phe Pro Trp Phe Ala Tyr Trp Gly
210                 215                 220

Gln Gly Thr Pro Val Thr Val Ser Gly Gly Gly Ser Asp Ile Val
225                 230                 235                 240

Met Thr Gln Ser Pro Ser Ser Leu Ala Val Ser Pro Gly Glu Arg Val
                245                 250                 255

Thr Leu Thr Cys Lys Ser Ser Gln Ser Leu Phe Asn Ser Arg Thr Arg
            260                 265                 270

Lys Asn Tyr Leu Gly Trp Tyr Gln Gln Lys Pro Gly Gln Ser Pro Lys
        275                 280                 285

Leu Leu Ile Tyr Trp Ala Ser Thr Arg Glu Ser Gly Val Pro Asp Arg
290                 295                 300

Phe Ser Gly Ser Gly Ser Gly Thr Asp Phe Thr Leu Thr Ile Asn Ser
305                 310                 315                 320

Leu Gln Ala Glu Asp Val Ala Val Tyr Tyr Cys Thr Gln Val Tyr Tyr
                325                 330                 335

Leu Cys Thr Phe Gly Ala Gly Thr Lys Leu Glu Leu Lys Arg Leu Asp
            340                 345                 350

His His His His His His
        355
```

<210> SEQ ID NO 13
<211> LENGTH: 1152

<212> TYPE: DNA
<213> ORGANISM: Artificial Sequence
<220> FEATURE:
<223> OTHER INFORMATION: Description of Artificial Sequence: Synthetic chimeric sequence from multiple species

<400> SEQUENCE: 13

```
atgggatgga gctgtatcat cctcttcttg gtagcaacag ctacaggtgt ccactccatg      60
gaagtgcagc tggtggagtc agggggagac ttagtgaagc ctggagggtc cctgaaactc     120
tcctgtgcag cctctggatt cactttcagt atttacacca tgtcttggct tcgccagact     180
ccgggaaagg ggctggagtg gtcgcaacc ctgagtggtg atggtgatga catctactat      240
ccagacagtg tgaagggtcg attcaccatc tccagagaca atgccaagaa cagcctatat     300
ctgcagatga acagtctaag ggctgaggac acggccttgt attactgtgc aagggtgcga     360
cttggggact gggacttcga tgtctggggc caagggacca cggtctccgt ctcctcagga     420
ggtggcggat ccgacatcca gctgacccag agcccaagca gcctgagcgc cagcgtgggt     480
gacagagtga ccatcacctg taaggccagt caggatgtgg gtacttctgt agcttggtac     540
cagcagaagc caggtaaggc tccaaagctg ctgatctact ggacatccac ccggcacact     600
ggtgtgccaa gcagattcag cggtagcggt agcggtaccg acttcacctt caccatcagc     660
agcctccagc cagaggacat cgccacctac tactgccagc aatatagcct ctatcggtcg     720
ttcggccaag gaccaaggt ggaaatcaaa cgtctcgagg cggaggtag cgaggtccaa       780
ctggtggaga gcggtggagg tgttgtgcaa cctggccggt ccctgcgcct gtcctgctcc     840
gcatctggct tcgatttcac acatattgg atgagttggg tgagacaggc acctggaaaa      900
ggtcttgagt ggattggaga aattcatcca gatagcagta cgattaacta tgcgccgtct     960
ctaaaggata gatttacaat atcgcgagac aacgccaaga acacattgtt cctgcaaatg    1020
gacagcctga ccccgaaga caccggggtc tattttgtg caagccttta cttcggcttc      1080
ccctggtttg cttattgggg ccaagggacc ccggtcaccg tctcagtcga ccatcatcat    1140
catcatcatt ga                                                       1152
```

<210> SEQ ID NO 14
<211> LENGTH: 1134
<212> TYPE: DNA
<213> ORGANISM: Artificial Sequence
<220> FEATURE:
<223> OTHER INFORMATION: Description of Artificial Sequence: Synthetic chimeric sequence from multiple species

<400> SEQUENCE: 14

```
atgggatgga gctgtatcat cctcttcttg gtagcaacag ctacaggtgt ccactccatg      60
gacatccagc tgacccagag cccaagcagc ctgagcgcca gcgtgggtga cagagtgacc     120
atcacctgta aggccagtca ggatgtgggt acttctgtag cctggtacca gcagaagcca     180
ggtaaggctc caaagctgct gatctactgg acatccaccc ggcacactgg tgtgccaagc     240
agattcagcg gtagcggtag cggtaccgac ttcaccttca ccatcagcag cctccagcca    300
gaggacatcg ccacctacta ctgccagcaa tatagcctct atcggtcgtt cggccaaggg    360
accaaggtgg aaatcaaacg tggaggtggc aattcatgg aggtccaact ggtggagagc      420
ggtggaggtg ttgtgcaacc tggccggtcc ctgcgcctgt cctgctccgc atctggcttc    480
gatttcacca catattggat gagttgggtg agacaggcac tggaaaagg tcttgagtgg      540
attggagaaa ttcatccaga tagcagtacg attaactatg cgccgtcgct aaaagataga    600
```

| | | |
|---|---|---|
| tttacaatat cgcgagacaa cgccaagaac acattgttcc tgcaaatgga cagcctgaga | 660 |
| cccgaagaca ccggggtcta tttttgtgca agcctttact tcggcttccc ctggtttgct | 720 |
| tattggggcc aagggacccc ggtcaccgtc tccggaggcg gtggatccga cattgtgatg | 780 |
| acacaatctc catcctccct ggctgtgtca cccggggaga gggtcactct gacctgcaaa | 840 |
| tccagtcaga gtctgttcaa cagtagaacc cgaaagaact acttgggttg gtaccagcag | 900 |
| aaaccgggc agtctcctaa acttctgatc tactgggcat ctactcggga atctggggtc | 960 |
| cctgatcgct tctcaggcag tggatccgga acagatttca ctctcaccat caacagtctg | 1020 |
| caggctgaag acgtggcagt ttattactgc actcaagttt attatctgtg cacgttcggt | 1080 |
| gctgggacca agctggagct gaaacggctc gaccatcatc atcatcatca ttga | 1134 |

<210> SEQ ID NO 15
<211> LENGTH: 9116
<212> TYPE: DNA
<213> ORGANISM: Artificial Sequence
<220> FEATURE:
<223> OTHER INFORMATION: Description of Artificial Sequence: Synthetic
chimeric sequence from multiple species

<400> SEQUENCE: 15

| | |
|---|---|
| ttccataggc tccgcccccc tgacgagcat cacaaaaatc gacgctcaag tcagaggtgg | 60 |
| cgaaacccga caggactata aagataccag gcgtttcccc ctggaagctc cctcgtgcgc | 120 |
| tctcctgttc cgaccctgcc gcttaccgga tacctgtccg cctttctccc ttcgggaagc | 180 |
| gtggcgcttt ctcatagctc acgctgtagg tatctcagtt cggtgtaggt cgttcgctcc | 240 |
| aagctgggct gtgtgcacga accccccgtt cagcccgacc gctgcgcctt atccggtaac | 300 |
| tatcgtcttg agtccaaccc ggtaagacac gacttatcgc cactggcagc agccactggt | 360 |
| aacaggatta gcagagcgag gtatgtaggc ggtgctacag agttcttgaa gtggtggcct | 420 |
| aactacggct acactagaag gacagtattt ggtatctgcg ctctgctgaa gccagttacc | 480 |
| ttcggaaaaa gagttggtag ctcttgatcc ggcaaacaaa ccaccgctgg tagcggtggt | 540 |
| tttttttgttt gcaagcagca gattacgcgc agaaaaaaag gatctcaaga agatcctttg | 600 |
| atctttccta cggggtctga cgctcagtgg aacgaaaact cacgttaagg gattttggtc | 660 |
| atgagattat caaaaaggat cttcacctag atccttttaa attaaaaatg aagttttaaa | 720 |
| tcaatctaaa gtatatatga gtaaacttgg tctgacagtt accaatgctt aatcagtgag | 780 |
| gcacctatct cagcgatctg tctatttcgt tcatccatag ttgcctgact ccccgtcgtg | 840 |
| tagataacta cgatacggga gggcttacca tctggcccca gtgctgcaat gataccgcga | 900 |
| gacccacgct caccggctcc agatttatca gcaataaacc agccagccgg aagggccgag | 960 |
| cgcagaagtg gtcctgcaac tttatccgcc tccatccagt ctattaattg ttgccgggaa | 1020 |
| gctagagtaa gtagttcgcc agttaatagt ttgcgcaacg ttgttgccat tgctgcaggc | 1080 |
| atcgtggtgt cacgctcgtc gtttggtatg gcttcattca gctccggttc ccaacgatca | 1140 |
| aggcgagtta catgatcccc catgttgtgc aaaaaagcgg ttagctcctt cggtcctccg | 1200 |
| atcgttgtca gaagtaagtt ggccgcagtg ttatcactca tggttatggc agcactgcat | 1260 |
| aattctctta ctgtcatgcc atccgtaaga tgcttttctg tgactggtga gtactcaacc | 1320 |
| aagtcattct gagaatagtg tatgcggcga ccgagttgct cttgcccggc gtcaacacgg | 1380 |
| gataataccg cgccacatag cagaacttta aaagtgctca tcattggaaa acgttcttcg | 1440 |
| gggcgaaaac tctcaaggat cttaccgctg ttgagatcca gttcgatgta acccactcgt | 1500 |

```
gcacccaact gatcttcagc atcttttact ttcaccagcg tttctgggtg agcaaaaaca   1560
ggaaggcaaa atgccgcaaa aagggaata agggcgacac ggaaatgttg aatactcata   1620
ctcttccttt tcaatatta ttgaagcatt tatcagggtt attgtctcat gagcggatac   1680
atatttgaat gtatttagaa aaataaacaa atagggttc cgcgcacatt tccccgaaaa   1740
ggccacctga cgtctaagaa accattatta tcatgacatt aacctataaa aataggcgta   1800
tcacgaggcc ctttcgtctt caagaattcc gatccagaca tgataagata cattgatgag   1860
tttggacaaa ccacaactag aatgcagtga aaaaaatgct ttatttgtga aatttgtgat   1920
gctattgctt tatttgtaac cattataagc tgcaataaac aagttaacaa caacaattgc   1980
attcatttta tgtttcaggt tcaggggag gtgtgggagg tttttaaag caagtaaaac   2040
ctctacaaat gtggtatggc tgattatgat ctaaagccag caaaagtccc atggtcttat   2100
aaaaatgcat agctttagga ggggagcaga gaacttgaaa gcatcttcct gttagtcttt   2160
cttctcgtag acttcaaact tatacttgat gccttttcc tcctggacct cagagaggac   2220
gcctgggtat tctgggagaa gtttatattt ccccaaatca atttctggga aaaacgtgtc   2280
actttcaaat tcctgcatga tccttgtcac aaagagtctg aggtggcctg gttgattcat   2340
ggcttcctgg taaacagaac tgcctccgac tatccaaacc atgtctactt tacttgccaa   2400
ttccggttgt tcaataagtc ttaaggcatc atccaaactt ttggcaagaa aatgagctcc   2460
tcgtggtggt tctttgagtt ctctactgag aactatatta attctgtcct ttaaaggtcg   2520
attcttctca ggaatggaga accaggtttt cctacccata atcaccagat tctgtttacc   2580
ttccactgaa gaggttgtgg tcattctttg gaagtacttg aactcgttcc tgagcggagg   2640
ccagggtcgg tctccgttct tgccaatccc catattttgg gacacggcga cgatgcagtt   2700
caatggtcga accatgaggg caccaagcta gcttttttgca aaagcctagg cctccaaaaa   2760
agcctcctca ctacttctgg aatagctcag aggccgaggc ggcctcggcc tctgcataaa   2820
taaaaaaaat tagtcagcca tggggcgag aatgggcgga actgggcgga gttaggggcg   2880
ggatgggcgg agttaggggc gggactatgg ttgctgacta attgagatgc atgctttgca   2940
tacttctgcc tgctggggag cctggggact ttccacacct ggttgctgac taattgagat   3000
gcatgctttg catacttctg cctgctgggg agcctgggga ctttccacac cctaactgac   3060
acacattcca cagtcgacta gaatatggat agtgggtgtt tatgactctg ataagcctg   3120
aacaattgat gattaatgcc cctgagctct gttcttagta acatgtgaac atttacttgt   3180
gtcagtgtag tagatttcac atgacatctt ataataaacc tgtaaatgaa agtaatttgc   3240
attactagcc cagcccagcc catactaaga gttatattat gtctgtctca cagcctgctg   3300
ctgaccaata ttgaaaagaa tagaccttcg actggcagga agcaggtcat gtggcaaggc   3360
tatttgggga agggaaaata aaaccactag gtaaacttgt agctgtggtt tgaagaagtg   3420
gttttgaaac actctgtcca gccccaccaa accgaaagtc caggctgagc aaaacaccac   3480
ctgggtaatt tgcatttcta aaataagttg aggattcagc cgaaactgga gaggtcctct   3540
tttaacttat tgagttcaac cttttaattt tagcttgagt agttctagtt tccccaaact   3600
taagtttatc gacttctaaa atgtatttag aatttcgacc aattctcatg tttgacagct   3660
tatcatcgct gcactccgcc cgaaaagtgc gctcggctct gccaaggacg cggggcgcgt   3720
gactatgcgt gggctggagc aaccgcctgc tgggtgcaaa ccctttgcgc ccggactcgt   3780
ccaacgacta taaagagggc aggctgtcct ctaagcgtca ccacgacttc aacgtcctga   3840
gtaccttctc ctcacttact ccgtagctcc agcttcacca gatccctcga ctctagacac   3900
```

```
aggccgccac catgggatgg agctgtatca tcctcttctt ggtagcaaca gctacaggtg    3960
tccactccat ggaagtgcag ctggtggagt caggggagga cttagtgaag cctggagggt    4020
ccctgaaact ctcctgtgca gcctctggat tcactttcag tatttacacc atgtcttggc    4080
ttcgccagac tccgggaaag gggctggagt gggtcgcaac cctgagtggt gatggtgatg    4140
acatctacta tccagacagt gtgaagggtc gattcaccat ctccagagac aatgccaaga    4200
acagcctata tctgcagatg aacagtctaa gggctgagga cacggccttg tattactgtg    4260
caagggtgcg acttggggac tgggacttcg atgtctgggg ccaagggacc acggtctccg    4320
tctcctcagg aggtggcgga tccgacatcc agctgaccca gagcccaagc agcctgagcg    4380
ccagcgtggg tgacagagtg accatcacct gtaaggccag tcaggatgtg gtacttctg     4440 tagcttggta ccagcagaag ccaggtaagg ctccaaagct gctgatctac tggacatcca    4500
cccggcacac tggtgtgcca agcagattca gcggtagcgg tagcggtacc gacttcacct    4560
tcaccatcag cagcctccag ccagaggaca tcgccaccta ctactgccag caatatagcc    4620
tctatcggtc gttcggccaa gggaccaagg tggaaatcaa acgtctcgag ggcggaggta    4680
gcgaggtcca actggtggag agcggtggag gtgttgtgca acctggccgg tcccgcgcc    4740 tgtcctgctc cgcatctggc ttcgatttca ccacatattg gatgagttgg gtgagacagg    4800
cacctggaaa aggtcttgag tggattggag aaattcatcc agatagcagt acgattaact    4860
atgcgccgtc tctaaaggat agatttacaa tatcgcgaga caacgccaag aacacattgt    4920
tcctgcaaat ggacagcctg agacccgaag acaccggggt ctattttgt gcaagccttt     4980 acttcggctt ccctggtttt gcttattggg gccaagggac cccggtcacc gtctcagtcg    5040
accatcatca tcatcatcat tgataagatc ccgcaattct aaactctgag ggggtcggat    5100
gacgtggcca ttctttgcct aaagcattga gtttactgca aggtcagaaa agcatgcaaa    5160
gccctcagaa tggctgcaaa gagctccaac aaaacaattt agaactttat aaggaatag     5220 ggggaagcta ggaagaaact caaaacatca agattttaaa tacgcttctt ggtctccttg    5280
ctataattat ctgggataag catgctgttt tctgtctgtc cctaacatgc cctgtgatta    5340
tccgcaaaca acacacccaa gggcagaact ttgttactta aacaccatcc tgtttgcttc    5400
tttcctcagg aactgtggct gcaccatctg tcttcatctt cccgccatct gatgagcagt    5460
tgaaatctgg aactgcctct gttgtgtgcc tgctgaataa cttctatccc agagaggcca    5520
aagtacagtg gaaggtggat aacgccctcc aatcgggtaa ctcccaggag agtgtcacag    5580
agcaggacag caaggacagc acctacagcc tcagcagcac cctgacgctg agcaaagcag    5640
actacgagaa acacaaagtc tacgcctgcg aagtcaccca tcagggcctg agctcgcccg    5700
tcacaaagag cttcaacagg ggagagtgtt agagggagaa gtgcccccac ctgctcctca    5760
gttccagcct gaccccctcc catcctttgg cctctgaccc ttttttccaca ggggacctac    5820 ccctattgcg gtcctccagc tcatctttca cctcacccc ctcctcctcc ttggctttaa     5880
ttatgctaat gttggaggag aatgaataaa taaagtgaat ctttgcacct gtggtttctc    5940
tctttcctca tttaataatt attatctgtt gttttaccaa ctactcaatt tctcttataa    6000
gggactaaat atgtagtcat cctaaggcgc ataaccattt ataaaaatca tccttcattc    6060
tattttaccc tatcatcctc tgcaagacag tcctccctca aacccacaag ccttctgtcc    6120
tcacagtccc ctgggccatg gtaggagaga cttgcttcct tgttttcccc tcctcagcaa    6180
gccctcatag tccttttaa gggtgacagg tcttacagtc atatatcctt tgattcaatt     6240
```

```
ccctgagaat caaccaaagc aaattttca aaagaagaaa cctgctataa agagaatcat    6300
tcattgcaac atgatataaa ataacaacac aataaaagca attaaataaa caaacaatag    6360
ggaaatgttt aagttcatca tggtacttag acttaatgga atgtcatgcc ttatttacat    6420
ttttaaacag gtactgaggg actcctgtct gccaagggcc gtattgagta ctttccacaa    6480
cctaatttaa tccacactat actgtgagat taaaaacatt cattaaaatg ttgcaaaggt    6540
tctataaagc tgagagacaa atatattcta taactcagca attcccactt ctaggggttc    6600
gactggcagg aagcaggtca tgtggcaagg ctatttgggg aagggaaaat aaaaccacta    6660
ggtaaacttg tagctgtggt ttgaagaagt ggttttgaaa cactctgtcc agccccacca    6720
aaccgaaagt ccaggctgag caaaacacca cctgggtaat ttgcatttct aaaataagtt    6780
gaggattcag ccgaaactgg agaggtcctc ttttaactta ttgagttcaa ccttttaatt    6840
ttagcttgag tagttctagt ttccccaaac ttaagtttat cgacttctaa aatgtattta    6900
gaatttcgac caattctcat gtttgacagc ttatcatcgc tgcactccgc ccgaaaagtg    6960
cgctcggctc tgccaaggac gcgggggcgcg tgactatgcg tgggctggag caaccgcctg    7020
ctgggtgcaa acccttttgcg cccggactcg tccaacgact ataaagaggg caggctgtcc    7080
tctaagcgtc accacgactt caacgtcctg agtaccttct cctcacttac tccgtagctc    7140
cagcttcacc agatccctcg agtctagaca caggccgcca ccatgggatg gagctgtatc    7200
atcctcttct tggtagcaac agctacaggt gtccactcca tggacatcca gctgacccag    7260
agcccaagca gcctgagcgc cagcgtgggt gacagagtga ccatcacctg taaggccagt    7320
caggatgtgg gtacttctgt agcttggtac cagcagaagc caggtaaggc tccaaagctg    7380
ctgatctact ggacatccac ccggcacact ggtgtgccaa gcagattcag cggtagcggt    7440
agcggtaccg acttcacctt caccatcagc agcctccagc cagaggacat cgccacctac    7500
tactgccagc aatatagcct ctatcggtcg ttcggccaag gaccaaggt ggaaatcaaa    7560 cgtggaggtg gccaattcat ggaggtccaa ctggtggaga gcgtggagg tgttgtgcaa    7620 cctggccggt ccctgcgcct gtcctgctcc gcatctggct tcgatttcac cacatattgg    7680
atgagttggg tgagacaggc acctggaaaa ggtcttgagt ggattggaga aattcatcca    7740
gatagcagta cgattaacta tgcgccgtct ctaaaggata gatttacaat atcgcgagac    7800
aacgccaaga acacattgtt cctgcaaatg gacagcctga cccgaagaa caccggggtc    7860 tattttgtg caagccttta cttcggcttc cctggtttg cttattgggg ccaagggacc    7920
ccggtcaccg tctccggagg cggtggatcc gacattgtga tgacacaatc tccatcctcc    7980
ctggctgtgt cacccgggga gagggtcact ctgacctgca aatccagtca gagtctgttc    8040
aacagtagaa cccgaaagaa ctacttgggt tggtaccagc agaaaccagg gcagtctcct    8100
aaacttctga tctactgggc atctactcgg gaatctgggg tccctgatcg cttctcaggc    8160
agtggatccg gaacagattt cactctcacc atcaacagtc tgcaggctga agacgtggca    8220
gtttattact gcactcaagt ttattatctg tgcacgttcg gtgctgggac caagctggag    8280
ctgaaacggc tcgaccatca tcatcatcat cattgataag atctcggccg gcaagccccc    8340 gctcccggg ctctcgcggt cgcacgagga tgcttggcac gtaccccgtc tacatacttc    8400
ccaggcaccc agcatggaaa taaagcaccc accactgccc tgggcccctg cgagactgtg    8460
atggttcttt ccacgggtca ggccgagtct gaggcctgag tggcatgagg gaggcagagc    8520
gggtcccact gtcccacac tggcccaggc tgtgcaggtg tgcctgggcc gcctagggtg    8580
gggctcagcc aggggctgcc ctcggcaggg tgggggattt gccagcgtgg ccctccctcc    8640
```

```
agcagcagct gcctcgcgcg tttcggtgat gacggtgaaa acctctgaca catgcagctc    8700
ccggagacgg tcacagcttg tctgtaagcg gatgccggga gcagacaagc ccgtcagggc    8760
gcgtcagcgg gtgttggcgg gtgtcggggc gcagccatga cccagtcacg tagcgatagc    8820
ggagtgtata ctggcttaac tatgcggcat cagagcagat tgtactgaga gtgcaccata    8880
tgcggtgtga ataccgcac agatgcgtaa ggagaaaata ccgcatcagg cgctcttccg     8940
cttcctcgct cactgactcg ctgcgctcgg tcgttcggct gcggcgagcg gtatcagctc    9000
actcaaaggc ggtaatacgg ttatccacag aatcagggga taacgcagga aagaacatgt    9060
gagcaaaagg ccagcaaaag gccaggaacc gtaaaaaggc cgcgttgctg gcgttt        9116
```

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 16

Gly Gly Gly Gly Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 17

Leu Glu Gly Gly Gly Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 18

Gly Gly Gly Gln Phe Met
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 19

Gly Gly Gly Gly Ser
1               5

<210> SEQ ID NO 20
<211> LENGTH: 6
<212> TYPE: PRT
<213> ORGANISM: Artificial Sequence
<220> FEATURE:

-continued

<223> OTHER INFORMATION: Description of Artificial Sequence: Synthetic 6xHis tag

<400> SEQUENCE: 20

His His His His His His
1               5